United States Patent
Chung et al.

(10) Patent No.: US 12,258,616 B2
(45) Date of Patent: *Mar. 25, 2025

(54) METHODS AND KITS USEFUL FOR DIAGNOSIS OF HUMAN PAPILLOMAVIRUS (HPV)

(71) Applicant: Phase Scientific International, Ltd., Hong Kong (CN)

(72) Inventors: Cheuk Yiu Tenny Chung, Hong Kong (CN); Vasu Saini, Hong Kong (CN); Daniel William Bradbury, Hong Kong (CN); Harsha Madan Kittur, Singapore (SG); Masae Kobayashi Wen, Buena Park, CA (US); Cheuk Yin Lam, Hong Kong (CN); Kar Kee Tse, Hong Kong (CN); Kit Cheung, Hong Kong (CN); Wing Yee Ng, Hong Kong (CN); Yin To Chiu, Hong Kong (CN); Garrett Lee Mosley, Hong Kong (CN)

(73) Assignee: PHASE SCIENTIFIC INTERNATIONAL, LTD., Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/889,398

(22) Filed: Sep. 19, 2024

(65) Prior Publication Data

US 2025/0027137 A1 Jan. 23, 2025

Related U.S. Application Data

(62) Division of application No. 18/463,313, filed on Sep. 8, 2023, now Pat. No. 12,129,511.

(60) Provisional application No. 63/381,932, filed on Nov. 2, 2022, provisional application No. 63/381,933, filed on Nov. 2, 2022.

(51) Int. Cl.
*C12Q 1/6806* (2018.01)
*C12Q 1/70* (2006.01)

(52) U.S. Cl.
CPC ............. *C12Q 1/6806* (2013.01); *C12Q 1/70* (2013.01)

(58) Field of Classification Search
None
See application file for complete search history.

(56) References Cited

U.S. PATENT DOCUMENTS

| | | | |
|---|---|---|---|
| 6,863,828 B2 | 3/2005 | Nagaraj et al. | |
| 7,335,492 B2 | 2/2008 | Penttila et al. | |
| 7,553,658 B2 | 6/2009 | Kepka et al. | |
| 7,626,017 B2 | 12/2009 | Laugharn, Jr. et al. | |
| 8,158,007 B2 | 4/2012 | Franzreb et al. | |
| 11,287,426 B2 | 3/2022 | Kamei et al. | |
| 11,327,075 B2 | 5/2022 | Kamei et al. | |
| 2014/0121357 A1 | 5/2014 | Segura Ruiz et al. | |
| 2015/0253320 A1 | 9/2015 | Kamei et al. | |
| 2018/0100854 A1 | 4/2018 | Kamei et al. | |
| 2018/0259521 A1 | 9/2018 | Kamei et al. | |
| 2019/0033308 A1 | 1/2019 | Kamei et al. | |
| 2019/0250156 A1 | 8/2019 | Kamei et al. | |
| 2019/0391143 A1 | 12/2019 | Kamei et al. | |
| 2020/0284791 A1 | 9/2020 | Kamei et al. | |
| 2022/0252598 A1 | 8/2022 | Kamei et al. | |

FOREIGN PATENT DOCUMENTS

| | | |
|---|---|---|
| CN | 101835790 A | 9/2010 |
| CN | 103476786 A | 12/2013 |
| CN | 103797023 A | 5/2014 |
| CN | 104707358 A | 6/2015 |
| CN | 108342383 A | 7/2018 |
| CN | 110003323 A | 7/2019 |
| CN | 111304291 A | 6/2020 |
| WO | 2007140417 A2 | 12/2007 |
| WO | 2015099550 A1 | 7/2015 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A1 | 3/2019 |
| WO | 2019118705 A1 | 6/2019 |
| WO | 2019118712 A1 | 6/2019 |
| WO | 2019143895 A1 | 7/2019 |
| WO | 2019143943 A1 | 7/2019 |
| WO | 2019144016 A1 | 7/2019 |

(Continued)

OTHER PUBLICATIONS

Gu, Yulan, et al. "Circulating HPV cDNA in the blood as a reliable biomarker for cervical cancer: a meta-analysis." PLoS One 15.2 (2020): e0224001.*
Luechau, Frank; et al. (2009) Primary capture of high molecular weight nucleic acids using aqueous two-phase systems. Separation and purification technology, 66.1: 202-207.
Nazer, Behzad; et al. (2017) Plasmid DNA affinity partitioning using polyethylene glycol-sodium sulfate aqueous two-phase systems. Journal of Chromatography B, 1044: 112-119.
Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.
Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

(Continued)

*Primary Examiner* — Patrick T Lewis
(74) *Attorney, Agent, or Firm* — EAGLE IP LIMITED

(57) ABSTRACT

The present disclosure relates to methods, compositions, and kits for concentrating and purifying at least one target analyte from a clinical biological sample. In some embodiments, the methods involve one or more aqueous two-phase system (ATPS) compositions and at least one solid phase medium. Some embodiments provide a kit comprising one or more ATPS compositions, a binding buffer; and a solid phase medium. Other embodiments provide methods of treating cancers or infectious diseases in a patient in need thereof.

19 Claims, 10 Drawing Sheets

(56) References Cited

FOREIGN PATENT DOCUMENTS

| WO | 2019144030 A1 | 7/2019 |
|---|---|---|
| WO | 2020037214 A1 | 2/2020 |
| WO | 2021037075 A1 | 3/2021 |
| WO | 2021148393 A1 | 7/2021 |
| WO | 2021185336 A1 | 9/2021 |
| WO | 2022008591 A1 | 1/2022 |

OTHER PUBLICATIONS

T.Matos, et. al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil—Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Wu et al., "Factors Affecting Aqueous Two-Phase Extraction", Biopharmaceutical Technology (Fourth Edition), Aug. 2015, p. 122-126, China medicine science and technology press.

Filip Janku; et al., "A novel method for liquid-phase extraction of cell-free DNA for detection of circulating tumor DNA", Scientific reports, 2021, 11(1): 19653.

Daiki Nagata; et al., "Aqueous Two-phase Extraction System Using an Assembled Dextran-conjugated Magnetite Prepared by the Dextransucrase Reaction", Jun. 16, 2014, The Japanese Society of Applied Glycoscience, J. Appl. Glycosci., 61, 89-92 (2014).

Shin Hyunwoo et al., "Aqueous two-phase system to isolate extracellular vesicles from urine for prostate cancer diagnosis", PLoS One, vol. 13, No. 3, Mar. 27, 2018 (Mar. 27, 2018), p. 0194818.

Pereira Matheus M. et al., "Pre-treatment strategies based on aqueous two-phase systems comprising ionic liquids to improve the adrenal cancer diagnosis", Journal of Molecular Liquids, vol. 367, Sep. 22, 2022, p. 120409, XP093103949.

Mendes Maria S. M. et al., "Aqueous two-phase systems as multipurpose tools to improve biomarker analysis", Separation and Purification Technology, vol. 317, Apr. 17, 2023 (Apr. 17, 2023), p. 123875, XP093103947.

Lee, Hoyoon, et al., "Precision cell-free DNA extraction for liquid biopsy by integrated microfluidics." NPJ precision oncology 4.1 (2020): 3.

Ahmed et al., "Aqueous Two-Phase Systems and Microfluidics for Microscale Assays and Analytical Measurements", Annual Review of Analytical Chemistry, 2021 14:1, 231-255.

Fei Yu, et al., "Comparative Evaluation of Three Preprocessing Methods for Extraction and Detection of Influenza A Virus Nucleic Acids from Sputum", Front Med (Lausanne), 2018 year, vol. 5:56.

Piotr Chomczynski, et al., "The single-step method of RNA isolation by acid guanidinium thiocyanate-phenol-chloroform extraction: twenty-something years on", Nature Protocols, 2006, 1(2), 581-585.

\* cited by examiner

METHODS AND KITS USEFUL FOR DIAGNOSIS OF HUMAN PAPILLOMAVIRUS (HPV)

CROSS-REFERENCE TO RELATED APPLICATION

The present application is a Divisional application of U.S. patent application Ser. No. 18/463,313 filed on 8 Sep. 2023, which claims priority to U.S. Provisional Application Ser. No. 63/381,932 filed on Nov. 2, 2022, and U.S. Provisional Application Ser. No. 63/381,933 filed on Nov. 2, 2022. The entire contents of all the foregoing applications are hereby incorporated by reference in their entirety for all purposes.

FIELD OF INVENTION

This application relates to compositions, methods and kits for concentrating and purifying target analyte(s) using Aqueous Two-Phase System (ATPS) and a solid phase medium. More specifically, the present application relates to ATPS compositions, methods, and kits for concentrating and purifying at least one target analyte from a clinical biological sample.

BACKGROUND OF INVENTION

It is a challenging task to efficiently concentrate and isolate target analytes such as nucleic acids from clinical biological samples for downstream applications, such as for diagnostic tests. For example, some target analytes in clinical biological samples are found at extremely low concentrations, and oftentimes the yield of purified target analytes using conventional extraction methods are so low that subsequent analysis may not have sufficient diagnostic sensitivity and specificity. In some circumstances, the amount of binding buffer required for unprocessed sample lysates would be extremely large and unreasonable to incorporate into a conventional extraction workflow. Accordingly, there is a need for improved methods that are simple, stable, robust, and efficient in concentrating and purifying target analyte from clinical biological samples.

SUMMARY OF INVENTION

Disclosed herein are novel compositions, kits, methods and uses that are useful for the isolation, concentration and/or purification of target analytes, such as nucleic acids, employing at least one Aqueous Two-Phase System (ATPS) and solid phase media such as beads or columns.

In some embodiments, provided is a method for concentrating and purifying at least one target analyte from a clinical biological sample, including the steps of (a) combining the clinical biological sample with a first aqueous two-phase system (ATPS) composition including a polymer, a salt component including at least one salt, a surfactant, or any combination thereof dissolved in an aqueous solution to form a target-rich phase solution and a target-poor phase solution; (b) collecting the target-rich phase; (c) optionally adding the target-rich phase to a second ATPS composition including a polymer, a salt component including at least one salt, a surfactant, or any combination thereof dissolved in an aqueous solution to form a second target-rich phase solution and a second target-poor phase solution, and collecting the second target-rich phase; (d) optionally mixing the target-rich phase from step (b) or the second target-rich phase from step (c) with a binding buffer to form a mixed solution; (e) contacting the target rich phase from step (b), the second target-rich phase from step (c) or the mixed solution from step (d) with a solid phase medium configured to selectively bind the target analyte such that the solid phase medium binds to the target analyte; and (f) eluting and collecting the target analyte from the solid phase medium with an eluting solution, resulting in a final solution containing the concentrated and purified target analyte.

In some embodiments, provided is a method of treating cancer or infectious disease in a patient in need thereof, including the steps of (i) obtaining a clinical biological sample from the patient; (ii) concentrating and purifying at least one target analyte from the clinical biological sample according to the preceding embodiments; (iii) analyzing the final solution; and (iv) treating the patient if the information obtained from the target analyte indicates that the patient has cancer or is at risk of developing cancer.

In some embodiments, provided is a kit including a first ATPS composition, a second ATPS composition, a binding buffer, and a solid phase medium.

Advantages

There are many advantages to the various embodiments of the present disclosure.

In some embodiments, the methods, compositions and kits of the present disclosure provide simple, less expensive, and efficient means to purify target analytes from different clinical/biological samples of different volumes. The methods and kits disclosed herein involve Aqueous Two-Phase Systems (ATPS) in the upstream process, which effectively removes interfering salts and proteins in the sample matrix that may prevent optimal binding of target analyte such as DNA and cell-free DNA (cfDNA) to a solid phase medium during purification. The method and kits in the present disclosure also surprisingly and effectively minimizes reagents use without requiring specialized laboratory equipment.

In some embodiments, the methods described herein surprisingly and effectively reduce the amount of binding buffer required for unprocessed sample lysates, allowing the methods to be incorporated into conventional extraction workflows.

In some embodiments, it is surprisingly found that although the disclosed methods include additional ATPS steps in the upstream process, which are potential sources for loss of target analyte (e.g. due to imperfect target partitioning in ATPS), the recovery efficiency of target analytes using the disclosed methods is surprisingly higher when compared to the recovery efficiency using methods without ATPS to purify the target analyte from the clinical biological sample.

One of the factors affecting the efficiency of extraction of targets is the composition of ATPS, as various components interact differently with the targets. In some embodiments, the composition of ATPS in the present disclosure is highly tunable depending on the desired target analyte to be recovered as various components interact differently with the target analyte. The methods, compositions and kits of the present disclosure can accommodate a wide range of target analytes and clinical/biological samples.

Using the methods and kits disclosed in the present invention, target analytes that exist at very small concentrations in the biological sample, such as cell-free DNA (cfDNA), can be concentrated and purified efficiently, removing unwanted proteins and ions that might interfere with downstream detection.

In some embodiments, a large clinical/biological sample volume results in a large first ATPS bottom phase. In some embodiments, a second ATPS is used to concentrate the large bottom phase of the first ATPS into a more concentrated smaller top phase volume for more user-friendly downstream processing. In some embodiments, the 2-step ATPS process is used on DNA, resulting in a further concentrated sample for detection.

In some embodiments, the methods and kits of the present invention are used for diagnostic tests for cancers such as bladder cancer and for infectious diseases such as Human papillomavirus (HPV).

These and other features and characteristics, as well as the methods of use, and functions of the related components, will become more apparent upon consideration of the following detailed description and the appended claims with reference to the accompanying figures, all of which form a part of this specification, wherein like reference numerals designate corresponding parts in the various figures. It is to be expressly understood, however, that the drawings are for the purpose of illustration and description only and are not intended as a definition of the limits of the claims.

BRIEF DESCRIPTION OF FIGURES

FIG. 1A shows an example workflow of bead purification according to an example embodiment described in Example 1a.

FIG. 2A is a graph showing the average CT values of 145 bp DNA recovered from plasma using magnetic beads with and without prior ATPS steps, according to example methods as described in Example 2a.

FIG. 2B is a graph showing the average CT values of 2000 bp DNA recovered from plasma using magnetic beads with and without prior ATPS steps, according to example methods as described in Example 2a.

FIG. 3A is a graph showing the average CT values of 145 bp DNA recovered from plasma using spin column with and without prior ATPS steps, according to example methods as described in Example 3a.

FIG. 3B is a graph showing the average CT values of 2000 bp DNA recovered from plasma using spin column with and without prior ATPS steps, according to example methods as described in Example 3a.

FIG. 4A is a graph showing the average CT values of 145 bp DNA recovered from urine using magnetic beads with and without prior ATPS steps, according to example methods as described in Example 4a.

FIG. 4B is a graph showing the average CT values of 2000 bp DNA recovered from urine using magnetic beads with and without prior ATPS steps, according to example methods as described in Example 4a.

FIG. 5A is a graph showing the average CT values of 145 bp DNA recovered from urine using spin column with and without prior ATPS steps, according to example methods as described in Example 5a.

FIG. 5B is a graph showing the average CT values of 2000 bp DNA recovered from urine using spin column with and without prior ATPS steps, according to example methods as described in Example 5a.

DETAILED DESCRIPTION

Figure 1A:
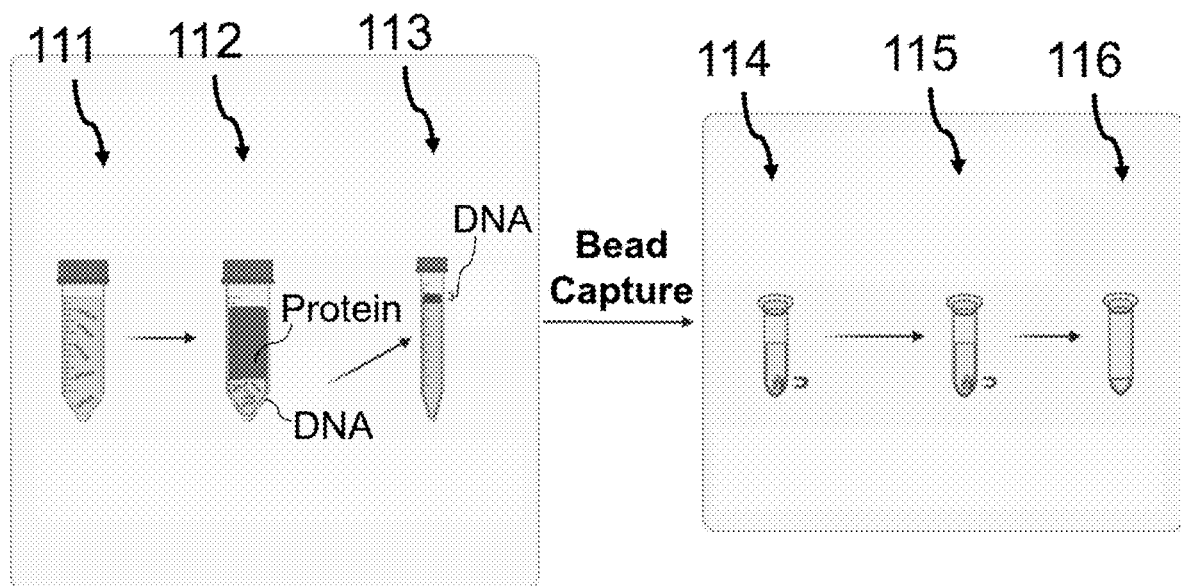

Unless indicated otherwise, the terms used herein, including technical and scientific terms, have the same meaning as usually understood by those skilled in the art to which the present invention pertains and detailed descriptions of well-known functions and constitutions that may obscure the gist of the present invention are omitted.

As used herein and in the claims, "comprising" and "including" mean including the following elements but not excluding others.

As used herein and in the claims, the terms "comprising" (or any related form such as "comprise" and "comprises"), "including" (or any related forms such as "include" or "includes"), "containing" (or any related forms such as "contain" or "contains"), or "having" (or any related forms such as "have" or "has") means including the following elements but not excluding others. It shall be understood that for every embodiment in which the term "comprising" (or any related form such as "comprise" and "comprises"), "including" (or any related forms such as "include" or "includes"), or "containing" (or any related forms such as "contain" or "contains") is used, this disclosure/application also includes alternate embodiments where the term "comprising", "including," "containing," or "having" is replaced with "consisting essentially of" or "consisting of". These alternate embodiments that use "consisting of" or "consisting essentially of" are understood to be narrower embodiments of the "comprising", "including," or "containing," embodiments.

For example, alternate embodiments of "a solution comprising A, B, and C" would be "a solution consisting of A, B, and C" and "a solution consisting essentially of A, B, and C." Even if the latter two embodiments are not explicitly written out, this disclosure/application includes those embodiments. Furthermore, it shall be understood that the scopes of the three embodiments listed above are different.

For the sake of clarity, "comprising", including, and "containing", and any related forms are open-ended terms which allows for additional elements or features beyond the named essential elements, whereas "consisting of" is a closed end term that is limited to the elements recited in the claim and excludes any element, step, or ingredient not specified in the claim.

"Consisting essentially of" limits the scope of a claim to the specified materials, components, or steps ("essential elements") that do not materially affect the essential characteristic(s) of the claimed invention. In some embodiments, the essential characteristics are the basic and novel characteristic(s) of the claimed invention.

As used herein, the singular forms "a", "an" and "the" are intended to include the plural forms as well, unless the context clearly indicates otherwise.

Where a range is referred to in the specification, the range is understood to include at least each discrete point within the range. For example, 1-7 in some embodiments means 1, 2, 3, 4, 5, 6, and 7. Unless otherwise indicated, a range is meant to include all values that fall within the range, including whole numbers, fractions, portions, and the like. For example, a range of 1-7 when described in a claim refers to a scope that includes values and sub-ranges such as 1, 1.5, 2-3, 6, and 7, by way of example. Unless otherwise indicated, a range is meant to include all values that fall within the range, including whole numbers, fractions, portions, and the like.

As used herein, the term "about" is understood as within a range of normal tolerance in the art and not more than ±10% of a stated value. By way of example only, about 50 means from 45 to 55 including all values in between. As used herein, the phrase "about" a specific value also includes the specific value, for example, about 50 includes 50.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent. The polymer and/or surfactant components whose use is described in the embodiments are "aqueous" in the sense that they form aqueous phases when combined with a solvent such as water. Further, as understood by the skilled person, in the present context the term liquid "mixture" refers merely to a combination of the herein-defined components.

As used herein, an aqueous two-phase system (ATPS) means a liquid-liquid separation system that can accomplish isolation or concentration of an analyte by partitioning, where two phases, sections, areas, components, or the like, interact differently with at least one analyte to which they are exposed and optionally dissolved. An ATPS is formed when two immiscible phase forming components, such as a salt and polymer, or two incompatible polymers (e.g., PEG and dextran) with certain concentrations are mixed in an aqueous solution. ATPS methods are relatively inexpensive and scalable because they employ two-phase partitioning to separate analytes (e.g., nucleic acids) from contaminants.

The term "isolated" as used herein refers to an analyte being removed from its original environment and thus is altered from its original environment. For example, an isolated nucleic acid generally is provided with fewer non-nucleic acid components (e.g., protein, lipid) than the amount of components present in a source sample. A composition comprising an isolated analyte, (e.g., sample nucleic acid) can be substantially isolated (e.g., about 90%, 91%, 92%, 93%, 94%, 95%, 96%, 97%, 98%, 99% or greater than 99% free of non-analyte components (such as non-nucleic acid components)).

As used herein, "concentrated" means that the mass ratio of analyte in question to the solution in which the analyte is suspended is higher than the mass ratio of said analyte in its pre-concentration solution. It can, for example, be slightly higher, or more preferably at least twice, ten times or one hundred times as high.

As used herein, the term "polymer" refers to any polymer including at least one substituted or non-substituted monomer. Examples of polymer includes, but are not limited to, homopolymer, copolymer, terpolymer, random copolymer, and block copolymer. Block copolymers include, but are not limited to, block, graft, dendrimer, and star polymers. As used herein, copolymer refers to a polymer derived from two monomeric species; similarly, a terpolymer refers to a polymer derived from three monomeric species. The two or three monomeric species can be the same or different species. The polymer also includes various morphologies, including, but not limited to, linear polymer, branched polymer, random polymer, crosslinked polymer, and dendrimer systems. In some embodiments, a polymer also includes its chemically modified equivalent, such as hydrophobically-modified, or silicone-modified. As an example, polyacrylamide polymer refers to any polymer including at least one substituted or non-substituted acrylamide unit, e.g., a homopolymer, copolymer, terpolymer, random copolymer, block copolymer or terpolymer of polyacrylamide; polyacrylamide can be a linear polymer, branched polymer, random polymer, crosslinked polymer, or a dendrimer of polyacrylamide; polyacrylamide can be hydrophobically-modified polyacrylamide, or silicone-modified polyacrylamide.

In some embodiments, examples of polymer include, but are not limited to, polyethers, polyimines, polyacrylates, polyalkylene glycols, vinyl polymers, alkoxylated surfactants, polysaccharides, polyether-modified silicones, polyacrylamide, polyacrylic acids and copolymers thereof. In some embodiments, the polymer is hydrophobically-modified, or silicone-modified. In some embodiments, the polymer is polyvinyl methylether, hydroxypropyl cellulose, or polyethyleneimine. In some embodiments, the polymer is PEG-PPG, polyvinyl pyrrolidone, or methyl cellulose. In some embodiments, the polymer is polyethylene glycol, polypropylene glycol, or dextran. In some embodiments, the polymer is alkylbenzenesulphonates, polyacrylamide, or isopropylacrylamide. In some embodiments, the polymer is acrylamide. In some embodiments, the polymer is dextran. In some embodiments, the polymer is polyalkylene glycols.

Examples of polyalkylene glycols (also referred as 'PAG' or 'poly(oxyalkylene)' or 'poly(alkylene oxide)') include, but are not limited to, hydrophobically modified polyalkylene glycols, poly(oxyalkylene) polymer, poly(oxyalkylene) copolymer, hydrophobically modified poly(oxyalkylene) copolymers, dipropylene glycol, tripropylene glycol, polyethylene glycol (also referred as 'PEG'), polypropylene glycol (also referred as 'PPG'). In some embodiments, examples of copolymers of PAGs include, but are not limited to, poly(ethylene glycol-propylene glycol) (also referred as 'PEG-PPG' or 'UCON'), and poly(ethylene glycol-ran-propylene glycol) (also referred as 'PEG-ran-PPG'). In some embodiments, PEG-PPG comprises random copolymers, block copolymers, or combination thereof. In some embodiments, PEG-PPG comprise both random copolymers and block copolymers. In some embodiments, PEG-PPG is PEG-ran-PPG.

As used herein, "vinyl polymer" refers to a group of polymers derived from substituted vinyl ($H_2C$=CHR) monomers. Examples of vinyl polymer include, but are not limited to, polyvinyl pyrrolidone, polyvinyl alcohol, polyvinyl caprolactam, and polyvinyl methylether.

Examples of polysaccharides include, but are not limited to, dextran, carboxymethyl dextran, dextran sulfate, hydroxypropyl dextran, starch, carboxymethyl cellulose, hydroxypropyl cellulose, methyl cellulose, ethylhydroxyethylcellulose, and maltodextrin. In some embodiments, polysaccharides are alkoxylated starches, alkoxylated cellulose, or alkyl hydroxyalkyl cellulose.

Examples of polyacrylamide include, but are not limited to, poly N-isopropylacrylamide.

Examples of polyimines include, but are not limited to, polyethyleneimine.

Examples of alkoxylated surfactants include, but are not limited to, carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, sodium N-lauroyl sarcosinate (NLS), ethoxylated aliphatic alcohol, ester, glycol esters of fatty acids, carboxylic amides, monoalkanolamine condensates, and polyoxyethylene fatty acid amides.

In some embodiments, the polymer has an average molecular weight of about 200-1,000 Da, 200-35,000 Da, 300-35,000 Da, 400-2,000 Da, or 400-35,000 Da. Examples thereof include, but are not limited to, polyalkylene glycols (PAGs) with average molecular weight of about 400 Da, 500 Da, 600 Da, 700 Da, 800 Da, 900 Da, 1,000 Da, 2,000 Da, 3,000 Da, 4,000 Da, 5,000 Da, 6,000 Da, 7,000 Da, 8,000 Da, 9,000 Da, 10,000 Da, 15,000 Da, 20,000 Da, 25,000 Da, 30000 Da, and 35000 Da. In some embodiments, the PAG has an average molecular weight at a range of between any of the two molecular weights listed above.

Examples of PAG include, but are not limited to PEG 200, PEG 300, PEG 400, PEG 500, PEG 600, PEG 700, PEG 800, PEG 900, PEG 1000, PEG 2000, PEG 3000, PEG 4000, PEG 5000, PEG 6000, PEG 7000, PEG 8000, PEG 9000, PEG 10000, PEG 15000, PEG 20000, PEG 25000, PEG 30000, PEG 35000, PPG 425, PPG 725, PPG 900, PPG 1000, and PPG 2000. In some embodiments, the PEG has an average molecular weight at a range of between any of the two PEG molecular weights listed above. In some embodiments, the PPG has an average molecular weight at a range of between any of the two PPG molecular weights listed above.

In some embodiments, the polymer comprises ethylene oxide (EO) and propylene oxide (PO) units, and has an ethylene oxide:propylene oxide (EO:PO) ratio of 90:10 to 10:90. In some embodiments, the polymer has an EO:PO ratio of 10:90, 15:85, 20:80, 25:75, 30:70, 35:65, 40:60, 45:55, 50:50, 55:45, 60:40, 65:35, 70:30, 75:25, 80:20, 85:15, or 90:10. In some embodiments, the polymer has an EO:PO ratio at a range between any of the two ratios listed above.

In some embodiments, the polymer is a PAG having an average molecular weight of about 980-12,000 Da and an EO:PO ratio of 50:50 to 75:25. Examples thereof include, but are not limited to, PEG-PPGs with average molecular weight of about 980 Da, 1,230 Da, 1,590 Da, 2,470 Da, 2,660 Da, 3,380 Da, 3,930 Da, 6,950 Da, and 12,000 Da. In some embodiments, the PEG-PPGs has an average molecular weight at a range of between any of the two PEG-PPGs molecular weights listed above. In some embodiments, PEG-PPG comprises an EO:PO ratio of 50:50, or 75:25. In some embodiments, the polymer is PEG-ran-PPG with an average molecular weight of about 2,500 or 12,000 Da and having an EO:PO ratio of about 75:25.

In some embodiments, the polymer is a vinyl polymer having an average molecular weight of about 2,500-2,500,000 Da. Examples thereof include, but are not limited to polyvinyl pyrrolidone with an average molecular weight of about 2,500 Da, 10,000 Da, 40,000 Da, 100,000 Da, and 2,500,000 Da. In some embodiments, the vinyl polymer has an average molecular weight at a range of between any of the two molecular weights listed above.

In some embodiments, the polymer is a polysaccharide and has an average molecular weight from about 6,000-5,000,000 Da. Examples thereof include, but are not limited to dextrans with average molecular weight of about 6,000 Da, 12,000 Da, 25,000 Da, 60,000 Da, 70,000 Da, 80,000 Da, 150,000 Da, 270,000 Da, 410,000 Da, 450,000 Da, 550,000 Da, 650,000 Da, 670,000 Da, 1,500,000 Da, 2,000,000 Da, 2,800,000 Da, 4,000,000 Da and 5,000,000 Da. In some embodiments, the dextran has an average molecular weight at a range of between any of the two molecular weights listed above.

In some embodiments, the polymer is a polyether and has an average molecular weight of about 200-35,000 Da. Examples thereof include, but are not limited to silicon modified polyether (or 'polyether-modified silicones') with average molecular weight of about 200 Da-35,000 Da.

In some embodiments, the polymer is a polyacrylamide and has an average molecular weight of 1,000-5,000,000 Da. Examples thereof include, but are not limited to polyacrylamide or poly(N-isopropylacrylamide) with average molecular weight of 1,000 Da, 2,000 Da, 5,000 Da, 10,000 Da, 40,000 Da, 85,000 Da, 5,000,000 Da. In some embodiments, the polyacrylamide has an average molecular weight at a range of between any of the two molecular weights listed above.

In some embodiments, the polymer is a polyacrylic acid and has an average molecular weight of about 1,250-4,000,000 Da. Examples thereof include, but are not limited to, polyacrylic acids with average molecular weight of 1,200 Da, 2,100 Da, 5,100 Da, 8,000 Da, 8,600 Da, 8,700 Da, 16,000 Da, and 83,000 Da. In some embodiments, the polyacrylic acid has an average molecular weight at a range of between any of the two molecular weights listed above.

As used herein, the term "salt" refers to a substance having at least one cation and at least one anion. Examples of salts include, but are not limited to, salts wherein the cation is sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium or tetrabutyl ammonium, and/or wherein the anion is phosphate, hydrogen phosphate, dihydrogen phosphate, sulfate, sulfide, sulfite, hydrogen sulfate, carbonate, hydrogen carbonate, acetate, nitrate, nitrite, sulfite, chloride, fluoride, chlorate, perchlorate, chlorite, hypochlorite, bromide, bromate, hypobromite, iodide, iodate, cyanate, thiocyanate, isothiocyanate, oxalate, formate, chromate, dichromate, permanganate, polyacrylate, hydroxide, hydride, citrate, borate, or tris. In some embodiments, the salts are kosmotropic salts, chaotropic salts, or inorganic salts.

As used herein, a "surfactant" includes, but is not limited to, an anionic surfactant, nonionic surfactant, cationic surfactant, zwitterionic surfactant or amphoteric surfactant.

Examples of anionic surfactants include, but are not limited to, carboxylates, sulfonates (also referred as 'sulphonates'), petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, and sodium N-lauroyl sarcosinate (NLS).

Examples of nonionic surfactants include, but are not limited to, ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, and polyoxyethylene fatty acid amides.

Examples of cationic surfactants include, but are not limited to, quaternary ammonium salts, amines with amide linkages, polyoxyethylene alkyl amines, polyoxyethylene alicyclic amines, n,n,n',n' tetrakis substituted ethylenediamines, and 2-alkyl 1-hydroxethyl 2-imidazolines, Examples of amphoteric surfactants include, but are not limited to, n-coco 3-aminopropionic acid or sodium salt thereof, n-tallow 3-iminodipropionate or disodium salt thereof, n-carboxymethyl n dimethyl n-9 octadecenyl ammonium hydroxide, n-cocoamidethyl n hydroxyethylglycineor sodium salt thereof, and sodium N-lauroyl sarcosinate (NLS).

In some embodiments, the surfactant comprises a polymer such as PAG. In some embodiments, the surfactant has a structure of $EO_x$-$PO_y$-$EO_x$, wherein EO refers to an ethylene oxide unit and PO refers to a propylene oxide unit, and x and y are the respective number of monomers. In some embodiments, x=2-136. In some embodiments, y=16-62. In some embodiments, examples of surfactants include, but are not limited to, $(C_2H_4O)_nC_{14}H_{22}O$ wherein n=4-10 (such as Triton X-100, Triton X-114, Triton X-45, Tween 20, Igepal CA630), Brij 58, Brij O10, Brij L23, $EO_x$-$PO_y$-$EO_x$ wherein x=2-136 and y=16-62 (such as Pluronic L-61, Pluronic F-127), sodium dodecyl sulfate, sodium cholate, sodium deoxycholate, N-lauroyl sarcosine sodium salt (NLS), hexadecyltrimethylammonium bromide, or span 80.

As used herein, the terms "clinical biological sample", "clinical/biological sample", "clinical sample" or "biological sample" refer to any sample obtained directly or indirectly from a subject (e.g., a human). In some embodiments the subject is a human patient. Examples of clinical biological samples include but are not limited to blood, plasma, urine, saliva, stool, cerebrospinal fluid (CSF), lymph, serum, sputum, peritoneal fluid, sweat, tears, nasal swab, vaginal swab, endocervical swab, semen, breast milk, and other bodily fluids. In some embodiments, the clinical biological sample is obtained from a biological sample treated with a lysing composition.

In some embodiments, the target analyte is a nucleic acid, a protein, an antigen, a biomolecule, a sugar moiety, a lipid, a sterol, exosomes, or any combination thereof. In some embodiments, examples of target analyte include, but are not limited to, genomic DNA (gDNA), cDNA, plasmid DNA, mitochondrial DNA, cell-free DNA (cfDNA), circulating tumor DNA (ctDNA), circulating fetal DNA, cell-free microbial DNA, micro RNA (miRNA), messenger RNA (mRNA), transfer RNA (tRNA), ribosomal RNA (rRNA), circular RNA, long non-coding RNA (lncRNA) or combinations thereof.

As used herein, "cell-free DNA" (cfDNA) is DNA that is present outside a cell, e.g., DNA present in the sample (e.g. blood, plasma, serum, or urine) obtained from a subject.

The term "large volume", "large amount", "high volume", or "bulk fluid", "bulk fluid sample" when referring to liquid samples in the present disclosure means a biological sample that has a volume of at least 1 mL, 2 mL, 3 mL, 4 mL, 5 mL, 6 mL, 7 mL, 8 mL, 9 mL, 10 mL, 20 mL, 30 mL, 40 mL, 50 mL, 60 mL, 70 mL, 80 mL, 90 mL, 100 mL, 200 mL, 300 mL, 400 mL, 500 mL. In some embodiments, the sample has a volume of 1-5 mL, 1-10 mL, 15-20 mL, 10-20 mL, 20-30 mL, or 30-40 mL. In some embodiments, the sample has a volume of at least 40 mL. In some embodiments, the sample has a volume range of 10 mL-40 mL, 10 mL-50 mL, 10 mL-100 mL; 40 mL-50 mL, 40 mL-60 mL, 40 mL-100 mL, 40 mL-160 mL, 40 mL-200 mL, 50 mL-100 mL, 50 mL-200 mL, or 50 mL-300 mL. In some embodiments, the sample has a volume of at least 10 mL, 20 mL, 30 mL, 40 mL, 50 mL, 60 mL, 70 mL, 80 mL, 90 mL, or 100 mL; and at most 100 mL, 200 mL, 300 mL, 400 mL, or 500 mL.

As used herein, the term "chaotropic agent" refers to a substance that disrupts the hydrogen bonding network between water molecules in solution. In some embodiments, the chaotropic agent is thiocyanate, isothiocyanate, perchlorate, acetate, trichloroacetate, trifluoroacetate, chloride, or iodide. Examples of chaotropic agents include, but are not limited to, guanidinium hydrochloride (GHCl), guanidinium thiocyanate, guanidinium isothiocyanate (GITC)), sodium thiocyanate, sodium iodide, sodium perchlorate, sodium trichloroacetate, sodium trifluroacetate, lithium perchlorate, lithium acetate, magnesium chloride, phenol, 2-propanol, thiourea, urea and the like.

As used herein, the term "Ct", "CT", "Ct value" or "CT value" refers to a cycle threshold value and signifies the cycle of a PCR amplification assay in which signal from a reporter that is indicative of amplicon generation (e.g., fluorescence) first becomes detectable above a background level. In some embodiments, the CT value is an indirect indicator of the amount of target nucleic acid detected from a particular sample. In general, a lower CT value indicates a higher amount of the target nucleic acid in the sample, and a higher CT value indicates a lower amount of the target nucleic acid in the sample.

As used herein, the term "solid phase purification system" refers to a device, a product, a method or a process that is used to purify and/or selectively isolate a target analyte by chemical or physical means. In some embodiments, a solid phase purification system comprises a solid phase medium.

In some embodiments, a solid phase purification system refers to a magnetic beads workflow or a spin column workflow.

As used herein, the term "solid phase medium" refers to a material which selectively isolates a target analyte by chemical or physical means. In some embodiments, a solid phase medium is provided as a solid, or a solid supported in a vessel. In some embodiments, the solid phase medium is a solid phase extraction column, such as a spin column. In some embodiments, the solid phase medium is a plurality of beads, silica resins, silica membrane, silica gel, alumina gel, size exclusion resins, or ion-exchange resins.

As used herein, the terms "flow-through", "flow through" and "supernatant" all refer to the liquid or solution that passes through or separates from a solid phase medium, which can be removed or isolated from the solid phase medium. In some embodiments, supernatant refers to the flow-through that passes through a column.

As used herein, the terms "perturbing" or "perturbation" refers to the process of introducing physical force and disturbance into a provided system. In some embodiments, perturbing a solid phase extraction complex introduces centrifugation force, magnetic force, or combination thereof, which causes separation of target analyte(s) from or into the solid phase medium or supernatant. In some embodiments, examples of perturbing or perturbation are, but not limited to, centrifuging, vacuuming, magnetizing, vortexing, spinning, "spinned down", "spun down", swirling, rotating, shaking, stirring, rocking, and combination thereof. In some embodiments, centrifuging or vortexing is achieved by using a centrifuging machine (centrifuge) or a vortex. In some embodiments, vacuuming means contacting the solid phase extraction complex to a vacuum manifold to result in a flow-through or supernatant. In some embodiments, perturbation such as magnetizing, spinning, swirling, rotating, shaking, stirring, and rocking is achieved manually or by an appropriate instrument, such as a bench-top microcentrifuge. In some embodiments, centrifuging and magnetizing are performed simultaneously.

As used herein, the term "polymer-salt system" refers to any ATPS composition consisting essentially of a polymer and a salt component.

As used herein, the term "polymer-polymer system" refers to any ATPS composition consisting essentially of at least two polymers.

As used herein, the terms "micellar system" or "surfactant system" refer to any ATPS composition consisting essentially of at least two surfactants.

In some embodiments, the first ATPS composition or the second ATPS composition is a polymer-salt system consisting of a polymer, a salt component, and a surfactant.

As used herein, the term "salt component" refers to a mixture having at least one salt. In some embodiments, a salt component consists of a salt and an acid.

EMBODIMENTS OF THE PRESENT INVENTION

Embodiment 1

Example Methods, Compositions and Kits for Concentrating Target Analytes from a Bulk Fluid Sample One aspect provides a method for concentrating and purifying one or more target analytes from a bulk fluid sample, comprising the steps of:
(a) preparing a first aqueous two-phase system (ATPS) composition, wherein the first ATPS composition comprises polymers, salts, surfactants, or combinations thereof dissolved in an aqueous solution to form a first phase solution and a second phase solution;
(b) adding a sample solution prepared from the bulk fluid sample containing the target analyte(s) to the first ATPS composition, such that the target analyte(s) partition to the first phase solution;
(c) collecting the first phase solution and mixing the first phase solution with a second ATPS composition, wherein the second ATPS composition comprises polymers, salts, surfactants, or combinations thereof dissolved in an aqueous solution to form a third phase solution and a fourth phase solution, such that the target analyte(s) partition to and concentrate in the third phase solution;
(d) collecting the third phase solution and mixing the third phase solution with a binding buffer to form a mixed solution, wherein the binding buffer comprises at least one chaotropic agent;
(e) loading the mixed solution onto an extraction column configured to selectively extract and purify the target analyte(s);
(f) eluting and collecting the target analyte(s) from the extraction column, resulting in a final solution containing the concentrated and purified target analyte(s).

In some embodiments, the sample solution is prepared by dividing the bulk fluid sample containing the target analyte(s) into at least two aliquots of the sample solution, and the first ATPS composition is divided into at least two aliquots, wherein step (b) further includes the following steps:
(i) adding each aliquot of said sample solution prepared from the bulk fluid sample containing the target analyte(s) to each aliquot of the first ATPS composition, such that the target analyte(s) partition to the first phase solution;
(ii) collecting and combining the first phase solutions of the at least two aliquots of the first ATPS composition to form the first phase solution for step (c).

In some embodiments, the extraction column is a spin column, and wherein step (e) further comprise the following steps:
(i) loading a portion of the mixed solution onto the extraction column;
(ii) centrifuging the extraction column and discarding the flow-through (also referred as 'supernatant'); and
(iii) repeating steps (i) and (ii) above until all of the mixed solution has been passed through the extraction column.

In some embodiments, the method further comprises the step of:
(g) subjecting said final solution to a diagnostic assay for detection and quantification of said target analyte(s).

In another aspect, provided is a method for concentrating and purifying one or more target analytes from a bulk fluid sample, comprising the steps of:
(a) dividing the bulk fluid sample containing the target analyte(s) into at least two aliquots of a sample solution;
(b) preparing at least two aliquots of a first aqueous two-phase system (ATPS) composition, wherein the first ATPS composition comprises polymers, salts, surfactants, or combinations thereof dissolved in an aqueous solution to form a first phase solution and a second phase solution;

(c) adding each aliquot of said sample solution containing the target analyte(s) to each aliquot of the first ATPS composition, such that the target analyte(s) partition to the first phase solution;

(d) collecting the first phase solutions of the at least two aliquots of the first ATPS composition, and mixing the first phase solutions with a second ATPS composition, wherein the second ATPS composition comprises polymers, salts, surfactants, or combinations thereof dissolved in an aqueous solution to form a third phase solution and a fourth phase solution, such that the target analyte(s) partition to and concentrate in the third phase solution;

(e) collecting the third phase solution and mixing the third phase solution with a binding buffer to form a mixed solution, wherein the binding buffer comprises at least one chaotropic agent;

(f) loading the mixed solution onto an extraction column configured to selectively extract and purify the target analyte(s);

(g) eluting and collecting the target analyte(s) from the extraction column, resulting in a final solution containing the concentrated and purified target analyte(s).

In another aspect, provided is a method for concentrating and purifying one or more target analytes from a bulk fluid sample, comprising the steps of:

(a) dividing the bulk fluid sample containing the target analyte(s) into at least two aliquots of a sample solution;

(b) preparing at least two aliquots of a first aqueous two-phase system (ATPS) composition, wherein the first ATPS composition comprises polymers, salts, surfactants, or combinations thereof dissolved in an aqueous solution to form a first phase solution and a second phase solution;

(c) adding each aliquot of said sample solution containing the target analyte(s) to each aliquot of the first ATPS composition, such that the target analyte(s) partition to the first phase solution;

(d) collecting the first phase solutions of the at least two aliquots of the first ATPS composition, and mixing the first phase solutions with a second ATPS composition, wherein the second ATPS composition comprises polymers, salts, surfactants, or combinations thereof dissolved in an aqueous solution to form a third phase solution and a fourth phase solution, such that the target analyte(s) partition to and concentrate in the third phase solution;

(e) collecting the third phase solution and mixing the third phase solution with a binding buffer to form a mixed solution, wherein the binding buffer comprises at least one chaotropic agent;

(f) loading a portion of the mixed solution onto an extraction column configured to selectively extract and purify the target analyte(s);

(g) centrifuging the extraction column and discarding the flow-through;

(h) repeating steps (f) and (g) above until all of the mixed solution has been passed through the extraction column;

(i) eluting and collecting the target analyte(s) from the extraction column; resulting in a final solution containing the concentrated and purified target analyte(s); and (j) subjecting said final solution to a diagnostic assay for detection and quantification of said target analyte(s).

In some embodiments, the bulk fluid sample is selected from the group consisting of blood, plasma, serum, cerebrospinal fluid, urine, saliva, fecal matter, tear, sputum, nasopharyngeal mucus, vaginal discharge and penile discharge. In some embodiments, the bulk fluid sample is sample matrices that have been dissolved in a suitable preparation buffer, for example, fecal matter dissolved in a suitable volume (e.g. 500 mL) of water.

In some embodiments, the bulk fluid sample is urine.

In some embodiments, the bulk fluid sample has a volume of 40 mL or more, such as 50 mL, 60 mL, 70 mL, 80 mL, 90 mL, 100 mL, 200 mL, 300 mL, 400 mL, 500 mL or more.

In some embodiments, each aliquot of said sample solution has a volume of up to 25 ml, 26 mL, 27 mL, 28 mL, 29 mL, 30 mL, 31 mL, 32 mL, 33 mL, 34 mL, 35 mL, 36 mL, 37 mL, 38 mL, 39 mL, or 40 mL.

In some embodiments, the target analytes are selected from the group consisting of nucleic acids, a protein, an antigen, a biomolecule, a sugar moiety, a lipid, a sterol, and combinations thereof.

In some embodiments, the target analytes are DNA.

In some embodiments, the target analytes are cell-free DNA or circulating tumor DNA.

In some embodiments, the polymers are dissolve in the aqueous solution at a concentration of 4%-84% (w/w).

In some embodiments, the salts are dissolved in the aqueous solution at a concentration of 1%-55% (w/w). In some embodiments, the salts are dissolved in the aqueous solution at a concentration of 8%-55% (w/w).

In some embodiments, the surfactants are dissolved in the aqueous solution at a concentration of 0.05%-10% (w/w). In some embodiments, the surfactants are dissolved in the aqueous solution at a concentration of 0.05%-9.8% (w/w).

Another aspect provides an ATPS composition selected from the group consisting of A1, A2, A3, A4, AA1, AA2, AA3, and AA4 in Table I.

Another aspect provides a kit comprising a first ATPS composition selected from the group consisting of A1, A2, A3, and A4 in Table I; a second ATPS composition selected from the group consisting of AA1, AA2, AA3, and AA4 in Table I; and a binding buffer selected from the group consisting of B1, B2, and B3 in Table I.

In some embodiments, the kit further comprises an extraction column.

Various ATPS systems that can be used in various embodiments of the present invention include, but are not limited to, polymer-polymer, polymer-salt, polymer-surfactant, salt-surfactant, surfactant, surfactant-surfactant, or polymer-salt-surfactant.

In one embodiment, the first and/or second ATPS composition comprises a polymer. In some embodiments, polymers that may be employed include, but are not limited to, polyalkylene glycols, such as hydrophobically modified polyalkylene glycols, poly(oxyalkylene) polymers, poly(oxyalkylene) copolymers, such as hydrophobically modified poly(oxyalkylene) copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. In another embodiment, the first phase forming polymer comprises polyethylene glycol (PEG), polypropylene glycol (PPG), or dextran. In some embodiments, the polymer is selected from the group consisting of polyether, polyimine, polyalkylene glycol, vinyl polymer, alkoxylated surfactant, polysaccharides, alkoxylated starch, alkoxylated cellulose, alkyl hydroxyalkyl cellulose, polyether-modified silicones, polyacrylamide, polyacrylic acid and copolymer thereof. In some embodiments, the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether, dextran, carboxymethyl dextran, dextran sulfate, hydroxypropyl dextran, starch, carboxymethyl cellulose, polyacrylic acid, hydroxypropyl cellulose, methyl cellulose, ethylhydroxyethylcellulose, maltodextrin, polyethyleneimine, poly N-isopropylacrylamide and copolymers thereof. In some embodiments, the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether and poly N-isopropylacrylamide. In some embodiments, the polymer is selected from the group consisting of polyacrylamide, polyacrylic acid and copolymers thereof. In some embodiments, the polymer is selected from the group consisting of dextran, carboxymethyl dextran, dextran sulfate, hydroxypropyl dextran and starch. In some embodiments, the polymer has an average molecular weight in the range of 200-1,000 Da, 200-35,000 Da, 425-2,000 Da, 400-35,000 Da, 980-12,000 Da, or 3,400-5,000,000 Da. In some embodiments, the polymer comprises ethylene oxide and propylene oxide units, and the polymer has an EO:PO ratio of 90:10 to 10:90.

In one embodiment, the polymer concentration of the first and/or second ATPS composition is in the range of about 4% to about 84% by weight of the total weight of the aqueous solution (w/w). In various embodiments, the polymer solution is selected from a polymer solution that is about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, about 40% w/w, about 40.5% w/w, about 41% w/w, about 41.5% w/w, about 42% w/w, about 42.5% w/w, about 43% w/w, about 43.5% w/w, about 44% w/w, about 44.5% w/w, about 45% w/w, about 45.5% w/w, about 46% w/w, about 46.5% w/w, about 47% w/w, about 47.5% w/w, about 48% w/w, about 48.5% w/w, about 49% w/w, about 49.5% w/w, about 50% w/w, about 50.5% w/w, about 51% w/w, about 51.5% w/w, about 52% w/w, about 52.5% w/w, about 53% w/w, about 53.5% w/w, about 54% w/w, about 54.5% w/w, about 55% w/w, about 55.5% w/w, about 56% w/w, about 56.5% w/w, about 57% w/w, about 57.5% w/w, about 58% w/w, about 58.5% w/w, about 59% w/w, about 59.5% w/w, about 60% w/w, about 60.5% w/w, about 61% w/w, about 61.5% w/w, about 62% w/w, about 62.5% w/w, about 63% w/w, about 63.5% w/w, about 64% w/w, about 64.5% w/w, about 65% w/w, about 65.5% w/w, about 66% w/w, about 66.5% w/w, about 67% w/w, about 67.5% w/w, about 68% w/w, about 68.5% w/w, about 69% w/w, about 69.5% w/w, about 70% w/w, about 70.5% w/w, about 71% w/w, about 71.5% w/w, about 72% w/w, about 72.5% w/w, about 73% w/w, about 73.5% w/w, about 74% w/w, about 74.5% w/w, about 75% w/w, about 75.5% w/w, about 76% w/w, about 76.5% w/w, about 77% w/w, about 77.5% w/w, about 78% w/w, about 78.5% w/w, about 79% w/w, about 79.5% w/w, about 80% w/w, about 80.5% w/w, about 81% w/w, about 81.5% w/w, about 82% w/w, about 82.5% w/w, about 83% w/w, about 83.5% w/w, and about 84% w/w.

In one embodiment, the first and/or second ATPS composition comprises a salt and thereby forms a salt solution. In some embodiments, the salt includes, but is not limited to, kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. In another embodiment, the salt comprises NaCl, $Na_3PO_4$, $K_3PO_4$, $Na_2SO_4$, potassium citrate, $(NH_4)_2SO_4$, sodium citrate, sodium acetate or combinations thereof. Other salts, e.g. ammonium acetate, may also be used. In another embodiment, the salt may be selected from magnesium salt, a lithium salt, a sodium salt, a potassium salt, a cesium salt, a zinc salt and an aluminum salt. In some embodiments, the salt may be selected from a bromide salt, an iodide salt, a fluoride salt, a carbonate salt, a sulfate salt, a citrate salt, a carboxylate salt, a borate salt, and a phosphate salt. In some embodiments, the salt comprises potassium phosphate. In some embodiments, the salt comprises ammonium sulfate.

In one embodiment, the total salt concentration is in the range of about 0.01% to about 90%. A skilled person in the art will understand that the amount of salt needed to form an aqueous two-phase system will be influenced by molecular weight, concentration and physical status of the polymer.

In various embodiments, the salt concentration is about 1%-55% w/w. In various embodiments, the salt concentration is about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, about 40% w/w, about 40.5% w/w, about 41% w/w, about 41.5% w/w, about 42% w/w, about 42.5% w/w, about 43% w/w, about 43.5% w/w, about 44% w/w, about 44.5% w/w, about 45% w/w, about 45.5% w/w, about 46% w/w, about 46.5% w/w, about 47% w/w, about 47.5% w/w, about 48% w/w, about 48.5% w/w, about 49% w/w, about 49.5% w/w, about 50% w/w, about 50.5% w/w, about 51% w/w, about 51.5% w/w, about 52% w/w, about 52.5% w/w, about 53% w/w, about 53.5% w/w, about 54% w/w, about 54.5% w/w, about 55% w/w, about 55.5% w/w, about 56% w/w, about 56.5% w/w, about 57% w/w, about 57.5% w/w, about 58% w/w, about 58.5% w/w, about 59% w/w, about 59.5% w/w, about 60% w/w, about 60.5% w/w, about 61% w/w, about 61.5% w/w, about 62% w/w, about 62.5% w/w, about 63% w/w, about 63.5% w/w, about 64% w/w, about 64.5% w/w, about 65% w/w, about 65.5% w/w, about 66% w/w, about 66.5% w/w, about 67% w/w, about 67.5% w/w, about 68% w/w, about 68.5% w/w, about 69% w/w, about 69.5% w/w, about 70% w/w, about 70.5% w/w, about 71% w/w, about 71.5% w/w, about 72% w/w, about 72.5% w/w, about 73% w/w, about 73.5% w/w, about 74% w/w, about 74.5% w/w, about 75% w/w, about 75.5% w/w, about 76% w/w, about 76.5% w/w, about 77% w/w, about 77.5% w/w, about 78% w/w, about 78.5% w/w, about 79% w/w, about 79.5% w/w, or about 80% w/w.

In one embodiment, the first and/or second ATPS composition comprises a surfactant. In some embodiments, possible surfactants that may be employed include, but are not limited to, Triton-X, Triton-114, Igepal CA-630 and Nonidet P-40, anionic surfactants, such as carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, nonionic surfactants, such as ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, polyoxyethylene fatty acid amides, cationic surfactants, such as quaternary ammonium salts, amines with amide linkages, polyoxyethylene alkyl & alicyclic amines, n,n,n',n' tetrakis substituted ethylenediamines, 2-alkyl 1-hydroxethyl 2-imidazolines, and amphoteric surfactants, such as n-coco 3-aminopropionic acid and sodium salt thereof, n-tallow 3-iminodipropionate and disodium salt thereof, n-carboxymethyl n dimethyl n-9 octadecenyl ammonium hydroxide, n-cocoamidethyl n hydroxyethylglycine and sodium salt thereof.

In one embodiment, the surfactant concentration of the first ATPS composition is in the range of about 0.05% w/w to about 10% w/w. In various embodiments, the surfactant concentration is about 0.05% w/w, 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w.

In one embodiment, the binding buffer comprises a chaotropic agent. In some embodiments, possible chaotropic agents include, but are not limited to, n-butanol, ethanol, guanidinium chloride, guanidinium thiocyanate, lithium perchlorate, lithium acetate, magnesium chloride, phenol, 2-propanol, sodium dodecyl sulfate, thiourea, and urea.

In one embodiment, the concentration of the chaotropic agent in the binding buffer is in the range of about 0.1 M to 8 M. In various embodiments, the concentration of the chaotropic agent is about 0.1 M, about 0.2 M, about 0.3 M, about 0.4 M, about 0.5 M, about 0.6 M, about 0.7 M, about 0.8 M, about 0.9 M, about 1 M, about 1.1 M, about 1.2 M, about 1.3 M, about 1.4 M, about 1.5 M, about 1.6 M, about 1.7 M, about 1.8 M, about 1.9 M, about 2 M, about 2.1 M, about 2.2 M, about 2.3 M, about 2.4 M, about 2.5 M, about 2.6 M, about 2.7 M, about 2.8 M, about 2.9 M, about 3 M, about 3.1 M, about 3.2 M, about 3.3 M, about 3.4 M, about 3.5 M, about 3.6 M, about 3.7 M, about 3.8 M, about 3.9 M, about 4 M, about 4.1 M, about 4.2 M, about 4.3 M, about 4.4 M, about 4.5 M, about 4.6 M, about 4.7 M, about 4.8 M, about 4.9 M, about 5 M, about 5.1 M, about 5.2 M, about 5.3 M, about 5.4 M, about 5.5 M, about 5.6 M, about 5.7 M, about 5.8 M, about 5.9 M, about 6 M, about 6.1 M, about 6.2 M, about 6.3 M, about 6.4 M, about 6.5 M, about 6.6 M, about 6.7 M, about 6.8 M, about 6.9 M, about 7 M, about 7.1 M, about 7.2 M, about 7.3 M, about 7.4 M, about 7.5 M, about 7.6 M, about 7.7 M, about 7.8 M, about 7.9 M, or about 8 M.

In one embodiment, the possible extraction columns that may be employed include, but are not limited to, Epoch life science—EconoSpin Silica Membrane Mini Spin Column—1920-250, HiBinds RNA mini—RNACOL-02, Corbition silica spin column—PC0054, PuroSpin micro silica spin—Luna Nano USP003, Purospin nano silica spin—Lunonano USP002, Qiagen RNEasy minElute, Qiagen minElute—700384 Qiagen GMBH, and Qiagen mini.

Example Protocol for Processing 40 mL Samples

The following equipment are used for the methods in Examples 1 and 2 below:
  1. Centrifuge (e.g., for 15 and 50 ml conical tubes).
  2. Benchtop microcentrifuge (e.g., for 1 and 2 mL tubes).
  3. Pipettes and pipette tips (e.g., of 20 µL, 200 µL and 1000 µL capacity pipettes).
  4. Pipette aid and serological pipette tips (e.g., of 5 mL, 10 mL, and 50 mL).
  5. Water bath (e.g., set at 37° C.).

Specific examples of ATPS #1, ATPS #2, and binding buffers that can be used in the above protocol are shown in Table I below.

Below is an example method of how to concentrate and isolate a target analyte from a biological sample that has a volume of at least 40 mL. In this example, samples are prepared following the steps below:

40 mL of a biological sample is mixed with at least one lysing reagent (optional) using methods known to one of skill in the art to form one or more sample lysates.

A portion of the sample lysate (22.6 mL) is transferred into a first tube containing the first ATPS composition (ATPS #1) to form an ATPS #1 solution. The remaining sample lysate is poured into a second tube also containing ATPS #1 to form an ATPS #1 solution.

Both tubes containing the ATPS #1 solutions are vortexed thoroughly until homogenous and then each centrifuged for 6 minutes at 2300 RCF.

The bottom phases from the two ATPS #1 solution (e.g., around 3.5-5 mL of volume) are transferred (e.g., using a 10 mL serological pipette) into a tube containing a second ATPS composition (ATPS #2) to form an ATPS #2 solution. The ATPS #2 solution is vortexed thoroughly until homogenous, and then centrifuged for 6 minutes at 2300 RCF.

All of the top phases (around 400-600 uL) of the ATPS #2 solutions are transferred into a 5 mL microcentrifuge tube. ~2 mL of binding buffer is added to the microcentrifuge tube containing the ATPS #2 top phase, and the tube is vortexed briefly.

800 uL of the ATPS #2 top phase is transferred to a spin column and centrifuged for 30 sec at 12,000 rcf. The flow-through is discarded. This spin column step (step 6) is repeated until all samples have passed through the spin column.

Wash buffer is added (500 uL) to the spin column containing the mixture and the spin column containing the mixture is centrifuged for 30 sec at 12,000 rcf. The flow-through is discarded.

The spin column containing the mixture is centrifuged for 2 min at 16,000 rcf to remove any excess wash buffer.

The spin column containing the mixture is placed in a new 1.5 mL collection tube. 1× TE buffer (20-100 uL) is pipetted into the center of the spin column membrane. The spin column containing the mixture is incubated for 3 min and centrifuged at 1 min at 12,000 rcf to elute a sample solution containing the concentrated target analyte. The sample solution is stored in a freezer at −20° C. or below for optional further processing.

The above example procedure is just one example, and alternate methods and conditions may also be used.

For example, in step 2, the 40 mL sample after being subjected to the lysing agent is roughly split into two portions. However, bulk fluid samples can be divided up in a number of different permutations.

Specific examples of ATPS #1, ATPS #2, and binding buffers that can be used in the above protocol are shown in Table I below.

Example Protocol to Scale Up to 160 mL Sample Input

In this example, a larger bulk volume sample of around 160 mL is prepared following the steps below:

1. The 160 mL sample is divided into four separate 40 mL portions. For each 40 mL volume of sample input, steps (1) through (7) from the above Example 1 are performed.
2. The top phases of each ATPS #2 (about 400 uL-600 uL) is transferred into a 15 mL microcentrifuge tube. This extraction step may be done with a pipette, such a P200 pipette set to 200 uL for the first extraction.
3. For each 40 mL of starting sample, binding buffer (2 mL) is added to the tube containing the ATPS #2 top phases (ie. 160 mL sample scale up would require 4×ATPS #2 and 8 mL binding buffer). The tube is vortexed briefly.
4. 800 uL of the mixture (of starting sample and binding buffer) is transferred to the spin column.
5. The mixture is centrifuged for 30 sec at 12,000 rcf.
6. The flow-through is discarded. Steps 4-6 are repeated for the remaining sample until the entire mixture has passed through the spin columns. (For example, with a 800 uL spin column capacity, a 160 mL starting sample input volume required approximately 12 cycles)
7. Wash buffer is added to the spin column containing the mixture (500 uL).
8. The spin column containing the mixture is centrifuged for 30 sec at 12,000 rcf
9. The flow-through is discarded.
10. The spin column containing the mixture is centrifuged for 2 min at 16,000 rcf to remove any excess Wash buffer.
11. The spin column containing the mixture is placed in a new 1.5 mL collection tube.
12. 1×TE buffer (20-100 uL) is pipetted into the center of the spin column membrane.
13. The spin column containing the mixture is incubate for 3 min and centrifuged at 1 min at 12,000 rcf to elute a sample solution containing the concentrated target analyte.
14. The sample solution is stored in a freezer at −20° C. or below for optional further processing.

Evaluation of the Performance of the Example Extraction Kit

Performance of the presently disclosed methods and kits below can be evaluated following the steps below:

1. Several high-volume extraction kit components are prepared by varying the following components:
   a. ATPS #1
      i. Polymer
      ii. Salt
      iii. Surfactant
   b. ATPS #2
      i. Polymer
      ii. Salt
   c. Extraction column
   d. Binding Buffer
      i. Chaotropic agent
2. Sample solutions are made to evaluate and spike in known quantities of DNA target.
3. Extractions are made using variations of high-volume extraction kits prepared in Step 1 above as well as industry standard extraction kits using their specified procedures.
4. Target DNA are quantified using standard qPCR or ddPCR procedures The extracted samples from the methods of the present disclosure were found to contain higher concentrations of the target DNA compared to the industry standard kits.

Specific examples of ATPS #1, ATPS #2, and binding buffers are shown below.

TABLE I

Examples ATPS #1, ATPS #2, and binding buffers.

| Example | Reagent | Polymer | Salt | Surfactant | Chaotropic Agent |
|---|---|---|---|---|---|
| A1 | ATPS #1 | Polyvinyl alcohol 55-63% v/v | Sodium Sulfate 12-15% w/v | None | None |
| A2 | ATPS #1 | Polyethylene oxide (POE) 65-80% v/v | Phosphate Salt 18-24% w/v | Triton 0.05-0.4% v/v | None |
| A3 | ATPS #1 | PPG 78-84% v/v | Potassium citrate 19-23% w/v | Igepal 0.5-1.8% v/v | None |
| A4 | ATPS #1 | Dextran 42-57% w/v | Magnesium Salt 8-12% w/v | Anionic Surfactant 2-5% v/v | None |
| AA1 | ATPS #2 | Polyvinyl alcohol 12-19% v/v | Sodium Sulfate 32-55% w/v | None | None |
| AA2 | ATPS #2 | PPG 4-20% v/v | Potassium citrate 29-43% w/v | Igepal 4.5-9.8% v/v | None |

TABLE I-continued

Examples ATPS #1, ATPS #2, and binding buffers.

| Example | Reagent | Polymer | Salt | Surfactant | Chaotropic Agent |
|---|---|---|---|---|---|
| AA3 | ATPS #2 | Dextran 15-28% w/v | Magnesium Salt 20-31% w/v | Anionic Surfactant 2-5% v/v | None |
| AA4 | ATPS #2 | POE 8-14% v/v | Phosphate Salt 37-52% w/v | None | None |
| B1 | Binding Buffer | None | None | None | 2.5-6M Guanidinium Chloride |
| B2 | Binding Buffer | None | None | None | 3-8M Magnesium Chloride |
| B3 | Binding Buffer | None | None | None | 4-7M Guanidinium Thiocyanate |

Embodiment 2

Example Methods of Using ATPS with Magnetic Beads

Another aspect provides a method for concentrating and purifying one or more target analytes from a sample solution, comprising the steps of:
(a) adding a sample solution containing the target analyte(s) to a first aqueous two-phase system (ATPS) to form a mixture that partitions into a first phase and a second phase, wherein the target analyte(s) are concentrated in the first phase;
(b) isolating the first phase containing the concentrated target analyte(s), thereby resulting in a concentrated solution;
(c) applying magnetic beads to the concentrated solution, such that the magnetic beads bind the target analyte(s) to form a beads-analyte complex; and
(d) recovering the target analyte(s) from the beads-analyte complex, resulting in a final solution containing the target analyte(s) that is concentrated and purified.

In some embodiments, the step (b) further comprises the following steps:
(i) adding the isolated first phase that is concentrated with the target analyte(s) to a second ATPS to form a second mixture that partitions into a third phase and a fourth phase, wherein the target analyte(s) are concentrated in the third phase; and
(ii) isolating the third phase containing the concentrated target analyte(s) to form the concentrated solution in step (b) for step (c).

In some embodiments, the concentrated solution of step (b) is mixed with a binding buffer, wherein the binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea, thereby resulting in the concentration solution for step (c).

In some embodiments, the step (d) further comprises the steps of:
a. mixing the beads-analyte complex with a fractionation buffer comprising a polymer, a salt, a surfactant, a chaotropic agent or combinations thereof to form a fractionation solution, such that the target analyte(s) below a target size are released from the beads-analyte complex into the fractionation solution;
b. immobilizing the beads-analyte complex using a magnetic stand; and
c. isolating the target analyte(s) below the target size in the fractionation solution from the immobilized beads-analyte complex.

In some embodiments, the step (d) further comprises the steps of:
(iv) adding the isolated target analyte(s) below the target size to a second binding buffer, wherein the second binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea;
(v) applying magnetic beads to a mixture of the isolated target analyte(s) below the target size and the second binding buffer, wherein the magnetic beads bind the target analyte(s) below the target size to form a second beads-analyte complex; and
(vi) recovering the target analyte(s) from the second beads-analyte complex.

In some embodiments, the method further comprises the step of:
(e) subjecting said final solution to a diagnostic assay for detection and quantification of said target analyte(s).

In some embodiments, the target analyte(s) is selected from the group consisting of nucleic acids, a protein, an antigen, a biomolecule, a sugar moiety, a lipid, a sterol, and combinations thereof.

In some embodiments, the target analyte(s) is DNA.

In some embodiments, the target analyte(s) is cell-free DNA or circulating tumor DNA.

In some embodiments, the first ATPS comprises first ATPS components capable of forming the first phase and the second phase when the first ATPS components are dissolved in an aqueous solution, wherein the first ATPS components are selected from the group consisting of polymers, salts, surfactants, and combinations thereof.

In some embodiments, the second ATPS comprises second ATPS components capable of forming the third phase and the fourth phase when the second ATPS components are dissolved in an aqueous solution, wherein the second ATPS components are selected from the group consisting of polymers, salts, surfactants, and combinations thereof. In some embodiments, the polymers dissolve in the aqueous solution at a concentration of 4%-84% (w/w).

In some embodiments, the salts dissolve in the aqueous solution at a concentration of 1%-80% (w/w). In some embodiments, the salts dissolve in the aqueous solution at a concentration of 8%-80% (w/w).

In some embodiments, the surfactants dissolve in the aqueous solution at a concentration of 0.05%-10% (w/w). In some embodiments, the surfactants dissolve in the aqueous solution at a concentration of 0.05%-9.8% (w/w).

In some embodiments, the step (a) further comprises the steps of:
(i) embedding a porous material with components capable of forming the first ATPS; and
(ii) contacting the sample solution with the porous material embedded with the components, wherein said components form the first phase and the second phase when the sample solution travels through said porous material.

In one aspect, provided is a method for concentrating and purifying one or more target analytes from a sample solution, comprising the steps of:

(a) adding a sample solution containing the target analyte(s) to a first aqueous two-phase system (ATPS) to form a mixture that partitions into a first phase and a second phase, wherein the target analyte(s) are concentrated in the first phase;
(b) isolating the first phase containing the concentrated target analyte(s);
(c) adding the isolated first phase that is concentrated with the target analyte(s) to a second ATPS to form a second mixture that partitions into a third phase and a fourth phase, wherein the target analyte(s) are concentrated in the third phase;
(d) isolating the third phase containing the concentrated target analyte(s), thereby resulting in a concentrated solution;
(e) mixing the concentration solution with a binding buffer, wherein the binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea;
(f) applying magnetic beads to the mixture of the concentrated solution and the binding buffer, such that the magnetic beads bind the target analyte(s) to form a beads-analyte complex; and
(g) mixing the beads-analyte complex with a fractionation buffer comprising a polymer, a salt, a surfactant, a chaotropic agent or combinations thereof to form a fractionation solution, such that the target analyte(s) below a target size are released from the beads-analyte complex into the fractionation solution;
(h) immobilizing the beads-analyte complex using a magnetic stand;
(i) isolating the target analyte(s) below the target size in the fractionation solution from the immobilized beads-analyte complex;
(j) adding the isolated target analyte(s) below the target size to a second binding buffer, wherein the second binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea;
(k) applying magnetic beads to a mixture of the isolated target analyte(s) below the target size and the second binding buffer, wherein the magnetic beads bind the target analyte(s) below the target size to form a second beads-analyte complex;
(l) recovering the target analyte(s) below the target size from the second beads-analyte complex, resulting in a final solution containing the target analyte(s) below the target size that is concentrated and purified; and
(m) subjecting said final solution to a diagnostic assay for detection and quantification of said target analyte(s) below the target size.

Various ATPS systems that can be used in various embodiments of the present invention includes, but are not limited to, polymer-polymer, polymer-salt, polymer-surfactant, salt-surfactant, surfactant, surfactant-surfactant, or polymer-salt-surfactant. Examples of polymer, salts, and surfactants and their concentrations thereof that may be employed in the ATPS systems (first and/or second ATPS) include, but are not limited to, those that are described in Embodiment 1 above.

In some embodiments, the fractionation buffer comprises a polymer, a salt, a surfactant, a chaotropic agent or combinations thereof. In some embodiments, possible polymers, salts, surfactants and chaotropic agents that may be employed include, but are not limited to, those that are described in Embodiment 1 above.

In some embodiments, the possible magnetic beads that may be employed include, but are not limited to, those that are listed in Table II below.

TABLE II

Examples of magnetic beads

| Manufacturer | Bead Name | Specification |
| --- | --- | --- |
| MagQu | MF-SIL-5024 | Silica (SiO2) |
| MagQu | MF-SIL-5010 | Silica (SiO2) |
| Chemagen | M-PVA 011 | Unmodified |
| Chemagen | M-PVA 012 | Unmodified |
| Chemagen | M-PVA 021 | Highly carboxylated |
| Chemagen | M-PVA 022 | Highly carboxylated |
| Omega Biotek | Mag-Bind ® Particles CH | Silica (SiO2) |
| Thermofisher | Dynabeads™ MyOne™ SILANE | Silica-liked coated |
| Ocean Nanotech | PureBind T Bead | Silica (SiO2) |
| Ocean Nanotech | PureBind M Bead | Silica (SiO2) |
| Avanbio | FE10002-cf | COOH |
| Avanbio | FE10002 | COOH |

Example Protocol without Fractionation Buffer

Below is an example method of how to concentrate and isolate a target analyte according to the present disclosure. In this example, the target analyte is DNA.

Protocol steps are performed as follows:
1. A desired volume of treated biological sample (e.g., blood plasma) (e.g. 2-3 mL) is added to the first ATPS (Solution B) to form Solution B'. Treatment methods for the biological sample include, but are not limited to, lysing to form a sample lysate.
2. Solution B' is vortexed thoroughly (e.g., for about 10 seconds) until homogenous, and then centrifuged for 6 min at 2,300×g.
3. The bottom phase of Solution B' is transferred to the second ATPS (Solution C) to form Solution C'.
4. Solution C' is vortexed thoroughly until homogenous for 10 seconds, and then centrifuged for 1 min at 7,000×g.
5. 800 uL of a binding buffer (e.g., Binding Buffer BB1, BB2, or BB3) is added into a new 2 mL microcentrifuge tube.
6. The top phase of Solution C' containing the concentrated target analyte is transferred to the microcentrifuge tube from Step 5.
7. The provided magnetic beads (e.g. the magnetic beads selected from Table II, 12 µL) are vortexed before use, and then added into the microcentrifuge tube from Step 6, such that the magnetic beads bind the target analyte to form a beads-analyte complex.
8. The microcentrifuge tube is incubated with tilt rotation for 5 minutes, and then placed on a magnetic stand for 2 minute to immobilize the beads-analyte complex at the tube wall.
9. The supernatant from the microcentrifuge tube is pipetted and discarded without disturbing the beads-analyte complex. The microcentrifuge tube is then removed from the magnetic stand.
10. 800 uL of a binding buffer (e.g., Binding Buffer BB1, BB2, or BB3) is added into the microcentrifuge tube. The microcentrifuge tube is vortexed for 20 seconds, and then placed on the magnetic stand for 2 minute to immobilize the beads-analyte complex at tube wall.

11. The supernatant from the microcentrifuge tube is pipetted and discarded without disturbing the beads-analyte complex.
12. Suitable Washing Buffer (e.g. 800 uL) known to one skilled in the art is added into the microcentrifuge tube, which is then rotated on the magnetic stand, 120 degree each time, rotating a total of 720 degrees. After rotation, the supernatant from the microcentrifuge tube is pipetted and discarded without disturbing the beads-analyte complex.
13. Step 12 is repeated at least one time.
14. The microcentrifuge tube is then briefly spun with the hinge facing outwards to collect any remaining washing buffer in the tube.
15. The microcentrifuge tube is placed back on the magnetic stand for 1 minute to immobilize the beads-analyte complex at tube wall.
16. All supernatant is discarded carefully (e.g., using 10 µl pipette tips) without disturbing the beads-analyte complex.
17. The tube cap is opened and the beads-analyte complex is allowed to dry for 7 minutes on the magnetic rack.
18. The microcentrifuge tube is then removed from the magnetic stand after drying.
19. Suitable Elution Buffer (e.g. 40 uL) known to one skilled in the art is added directly to the beads-analyte complex (in the microcentrifuge tube).
20. The beads-analyte complex is resuspended by continuous stirring using a pipette and then pipetted up-and-down for 5 times.
21. The microcentrifuge tube is vortexed mildly (e.g., for 15 seconds).
22. The microcentrifuge tube is incubated at room temperature for 3 minutes.
23. The microcentrifuge tube is placed on the magnetic stand for 1 minute.
24. The supernatant containing the purified target analyte is collected into a clean Maximum Recovery tube carefully without disturbing the magnetic beads.
25. The purified target analyte is ready for immediate use or long-term storage at −20° C. or below.

Example Protocol with Fractionation Buffer

Below is another example method of how to concentrate and isolate a target analyte according to the present disclosure. In this example, the target analyte is DNA.

Protocol P steps are performed as follows:
1. A desired volume of treated biological sample (e.g., blood plasma) (e.g 2-3 mL) is added to the first ATPS (Solution B) to form Solution B'. Treatment methods for the biological sample include, but are not limited to, lysing to form a sample lysate.
2. Solution B' is vortexed thoroughly until homogenous for 10 seconds, and then centrifuged for 6 min at 2,300×g.
3. The bottom phase of Solution B' is transferred to the second ATPS (Solution C) to form Solution C'.
4. Solution C' is vortexed thoroughly until homogenous for 10 seconds, and then centrifuged for 1 min at 7,000×g.
5. 800 uL of binding buffer (e.g., Binding Buffer BB1, BB2, or BB3) is added into a new 2 mL microcentrifuge tube.
6. The top phase of Solution C' containing the concentrated target analyte is transferred to the tube filled with binding buffer from Step 5.
7. The provided magnetic beads (e.g. the magnetic beads selected from Table 1, 12 µL) are vortexed before use, and then added into the microcentrifuge tube from Step 6, such that the magnetic beads bind the target analyte to form a beads-analyte complex.
8. The microcentrifuge tube is incubated with tilt rotation for 5 minutes, and then placed on the magnetic stand for 2 minute to immobilize the beads-analyte complex at tube wall.
9. The supernatant from the microcentrifuge tube is pipetted and discarded without disturbing the beads-analyte complex. The microcentrifuge tube is then removed from the magnetic stand.
10. 300 uL Fractionation Buffer (e.g. Fractionation Buffer F1, F2 or F3) is added into the microcentrifuge tube. The microcentrifuge tube is vortexed for 20 seconds, incubated with tilt rotation for 5 minutes, and then placed on the magnetic stand for 2 minute to immobilize the beads-analyte complex at tube wall, such that the target analyte below a target size is released from the beads-analyte complex into the supernatant.
11. 600 uL of a second Binding Buffer (e.g., Binding Buffer BB1, BB2, or BB3) is added into a new 2 mL microcentrifuge tube.
12. The supernatant from Step 10 are transferred into the tube filled with the second Binding Buffer from Step 11.
13. The mixture is pipetted up and down to make sure all supernatant was transferred and mixed well with the second Binding Buffer.
14. The provided magnetic beads (e.g. the magnetic beads selected from Table 1, 6 uL) are vortexed before use, and then added into the microcentrifuge tube from Step 13, such that the magnetic beads bind the target analyte below the target size to form a second beads-analyte complex.
15. The microcentrifuge tube is incubated with tilt rotation for 5 minutes, and then placed on the magnetic stand for 4 minute to immobilize the second beads-analyte complex at tube wall.
16. The supernatant from the microcentrifuge tube is pipetted and discarded without disturbing the second beads-analyte complex.
17. Suitable Washing Buffer (e.g. 800 uL) known to one skilled in the art is added into the microcentrifuge tube, which is then rotated on magnetic stand, 120 degree each time, rotating a total of 720 degrees. After rotation, the supernatant from the microcentrifuge tube is pipetted and discarded without disturbing the second beads-analyte complex.
18. Step 17 is repeated.
19. The tube cap is opened and the beads are allowed to dry for 15 minutes on the magnetic rack.
20. The tube is removed from the magnetic stand after drying.
21. Suitable Elution Buffer (e.g. 40 uL) known to one skilled in the art is added directly to the second beads-analyte complex (in the microcentrifuge tube).
22. The second beads-analyte complex is resuspended by continuous stirring using pipette, then pipetted up-and-down for 5 times.
23. The microcentrifuge tubes are vortexed mildly for 10 seconds.
24. The microcentrifuge tube is incubated at room temperature for 3 minutes.
25. The microcentrifuge tube is placed on the magnetic stand for 1 minute.

26. The supernatant containing the purified target analyte below the target size is collected into a clean Maximum Recovery tube carefully without disturbing the magnetic bead.
27. The purified target analyte below the target size is ready for immediate use or long-term storage at −20° C. or below.

Evaluation of the Performance of the Example Methods

Performance of the presently disclosed methods and kits below can be evaluated following the steps below:

Several Magnetic Bead extraction kits components are prepared by varying the following components:
  Solution B (First ATPS)
    Polymer
    Salt
    Surfactant
  Solution C (Second ATPS)
    Polymer
    Salt
  Magnetic Beads
  Binding Buffer
    Chaotropic agent
    Polymer
  Fractionation Buffer
    Chaotropic agent
    Polymer Sample solutions are made to evaluate and spike in known quantities of DNA target.

Extraction are made using variations of Magnetic Bead extraction kits prepared in Step 1 above as well as industry standard extraction kits using their specified procedures.

Target DNA are quantified using standard qPCR or ddPCR procedures.

TABLE III

Examples ATPS #1, ATPS #2, and binding buffers.
In various example embodiments, Solution B, Solution C, the Binding Buffer, and Fractionation Buffer are selected from the Examples shown below in a variety of different combinations.

| Reagent | Example | Polymer | Salt | Surfactant | Chaotropic Agent |
|---|---|---|---|---|---|
| Solution B (first ATPS) | B1 | Polyvinyl alcohol 55-63% v/v | Sodium Sulfate 12-15% w/v | None | None |
| | B2 | Polyethylene oxide (POE) 55-65% v/v | Phosphate Salt 28-37% w/v | Triton 0.05-0.4% v/v | None |
| | B3 | PPG 78-84% v/v | Potassium citrate 19-23% w/v | Igepal 0.5-1.8% v/v | None |
| | B4 | Dextran 42-57% w/v | Magnesium Salt 8-12% w/v | Anionic Surfactant 2-5% v/v | None |
| Solution C (second ATPS) | C1 | Polyvinyl alcohol 12-19% v/v | Sodium Sulfate 32-55% w/v | None | None |
| | C2 | PPG 4-20% v/v | Potassium citrate 29-43% w/v | Igepal 4.5-9.8% v/v | None |
| | C3 | Dextran 15-28% w/v | Magnesium Salt 20-31% w/v | Anionic Surfactant 2-5% v/v | None |
| | C4 | POE 18-34% v/v | Phosphate Salt 67-80% w/v | None | None |
| Binding Buffer | BB1 | None | None | None | 2.5-6M Guanidinium Chloride |
| | BB2 | None | None | None | 3-8M Magnesium Chloride |
| | BB3 | None | None | None | 4-7M Guanidinium Thiocyanate |
| Fractionation Buffer | F1 | POE 1-5% v/v | None | None | 2-5M Guanidinium Thiocyanate |
| | F2 | PPG 78-84% v/v | None | None | 2.5-6M Guanidinium Chloride |
| | F3 | Dextran 42-57% w/v | Sodium Sulfate 12-15% w/v | Triton 0.05-0.4% v/v | 3-8M Magnesium Chloride |

Embodiment 3

In some embodiments, provided is a method for concentrating and purifying at least one target analyte from a clinical biological sample, including the steps of (a) combining the clinical biological sample with a first aqueous two-phase system (ATPS) composition including a polymer, a salt component including at least one salt, a surfactant, or any combination thereof dissolved in an aqueous solution to form a target-rich phase solution and a target-poor phase solution; (b) collecting the target-rich phase; (c) optionally adding the target-rich phase to a second ATPS composition including a polymer, a salt component including at least one salt, a surfactant, or any combination thereof dissolved in an aqueous solution to form a second target-rich phase solution and a second target-poor phase solution, and collecting the second target-rich phase; (d) optionally mixing the target-rich phase from step (b) or the second target-rich phase from step (c) with a binding buffer to form a mixed solution; (e) contacting the target rich phase from step (b), the second target-rich phase from step (c) or the mixed solution from step (d) with a solid phase medium configured to selectively bind the target analyte such that the solid phase medium binds to the target analyte; and (f) eluting and collecting the target analyte from the solid phase medium with an eluting solution, resulting in a final solution containing the concentrated and purified target analyte.

In some embodiments, the method further includes the step of washing the solid phase medium with one or more appropriate solvents to remove impurities after step (e) and before step (f).

In some embodiments, the appropriate solvent is the binding buffer.

In some embodiments, the method further includes the step of treating the clinical biological sample with a lysing composition before step (a).

In some embodiments, the binding buffer includes a chaotropic agent including an anion selected from the group consisting of thiocyanate, isothiocyanate, perchlorate, acetate, trichloroacetate, trifluoroacetate, chloride, and iodide.

In some embodiments, the binding buffer includes a chaotropic agent selected from the group consisting of guanidinium hydrochloride (GHCI), guanidinium thiocyanate, guanidinium isothiocyanate (GITC)), sodium thiocyanate, sodium iodide, sodium perchlorate, sodium trichloroacetate, sodium trifluoroacetate, lithium perchlorate, lithium acetate, magnesium chloride, phenol, 2-propanol, thiourea, and urea.

In some embodiments, the binding buffer includes a chaotropic agent at a concentration of 2M to 7M.

In some embodiments, the binding buffer further includes a polymer at a concentration of 5-20% (w/v).

In some embodiments, the clinical biological sample is blood, plasma, urine, saliva, stool, cerebrospinal fluid (CSF), lymph, serum, sputum, peritoneal fluid, sweat, tears, nasal swab, vaginal swab, endocervical swab, semen, or breast milk.

In some embodiments, the clinical biological sample is <500 mL.

In some embodiments, the target analyte is selected from the group consisting of a nucleic acid, a protein, an antigen, a biomolecule, a sugar moiety, a lipid, a sterol, exosomes, and any combination thereof.

In some embodiments, the target analyte is a nucleic acid, and the nucleic acid is gDNA, cDNA, plasmid DNA, mitochondrial DNA, cell-free DNA (cfDNA), circulating tumor DNA (ctDNA), circulating fetal DNA, cell-free microbial DNA, micro RNA (miRNA), messenger RNA (mRNA), transfer RNA (tRNA), ribosomal RNA (rRNA), circular RNA, long non-coding RNA (lncRNA) or combinations thereof.

In some embodiments, the nucleic acid is cfDNA, cell-free fetal DNA, mitochondrial DNA, cell-free microbial DNA, or ctDNA.

In some embodiments, the step (e) includes the following steps: (i) contacting a portion of the mixed solution with the solid phase medium such that the target analyte binds to the solid phase medium to form a solid phase extraction complex; (ii) perturbing the solid phase extraction complex and discarding the flow-through (also referred as 'supernatant'); and (iii) optionally repeating steps (i) and (ii).

In some embodiments, provided is a method or claim 16, wherein the solid phase medium is a plurality of beads.

In some embodiments, the beads are selected from the group consisting of magnetic beads, silica-based beads, carboxyl beads, hydroxyl beads, and amine-coated beads.

In some embodiments, the solid phase extraction complex is a beads-analyte complex; perturbing is spinning; and the flowthrough is the supernatant.

In some embodiments, the target analyte is a nucleic acid less than a target size; the plurality of beads binds to the target analyte and to other nucleic acids; the eluting solution is a fractionation buffer that, when contacted with the beads during the elution step (f), causes the target analyte to be released while not releasing the other nucleic acids, resulting in a final solution containing the concentrated and purified target analyte(s).

In some embodiments, the fractionation buffer includes a polymer, a chaotropic agent, or any combination thereof.

In some embodiments, the solid phase medium is an extraction column.

In some embodiments, the extraction column is a spin column.

In some embodiments, the step (e) includes the following steps: (i) loading a portion of the mixed solution from step (d) onto the extraction column; (ii) centrifuging the extraction column and discarding the flow-through; and (iii) optionally repeating steps (i) and (ii) above one or more times, until all of the mixed solution has been passed through the extraction column.

In some embodiments, the salt includes a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium.

In some embodiments, the salt includes an anion selected from the group consisting of phosphate, hydrogen phosphate, dihydrogen phosphate, sulfate, sulfide, sulfite, hydrogen sulfate, carbonate, hydrogen carbonate, acetate, nitrate, nitrite, sulfite, chloride, fluoride, chlorate, perchlorate, chlorite, hypochlorite, bromide, bromate, hypobromite, iodide, iodate, cyanate, thiocyanate, isothiocyanate, oxalate, formate, chromate, dichromate, permanganate, polyacrylate, hydroxide, hydride, citrate, borate, and tris.

In some embodiments, the polymer is selected from the group consisting of polyethers, polyimines, polyacrylates, polyalkylene glycols, vinyl polymers, alkoxylated surfactants, polysaccharides, alkoxylated starch, alkoxylated cellulose, alkyl hydroxyalkyl cellulose, polyether-modified silicones, polyacrylamide, polyacrylic acids and copolymers thereof. In some embodiments, the polymer is hydrophobically-modified, or silicone-modified.

In some embodiments, the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether, dextran, carboxymethyl dextran, dextran sulfate, hydroxypropyl dextran, starch, carboxymethyl cellulose, polyacrylic acid, hydroxypropyl cellulose, methyl cellulose, ethylhydroxyethylcellulose, maltodextrin, polyethyleneimine, poly N-isopropylacrylamide and copolymers thereof.

In some embodiments, the polymer is dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether and poly N-isopropylacrylamide.

In some embodiments, the polymer is a polyacrylamide, polyacrylic acid or copolymers thereof. In some embodiments, the polymer is dextran, carboxymethyl dextran, dextran sulfate, hydroxypropyl dextran or starch.

In some embodiments, the polymer has an average molecular weight in the range of 200-1,000 Da, 200-35,000 Da, 425-2,000 Da, 400-35,000 Da, 980-12,000 Da, or 3,400-5,000,000 Da. In some embodiments, the polymer comprises ethylene oxide and propylene oxide units. In some embodiments, the polymer has an EO:PO ratio of 90:10 to 10:90.

In some embodiments, the surfactant is selected from the group consisting of an anionic surfactant, a nonionic surfactant, a cationic surfactant, and an amphoteric surfactant; wherein the anionic surfactant is carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, or sodium N-lauroyl sarcosinate (NLS); the nonionic surfactant is ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, or polyoxyethylene fatty acid amides; the cationic surfactant is quaternary ammonium salts, amines with amide linkages, polyoxyethylene alkyl amines, polyoxyethylene alicyclic amines, n,n,n',n' tetrakis substituted ethylenediamines, or 2-alkyl 1-hydroxethyl 2-imidazolines; and the amphoteric surfactant is n-coco 3-aminopropionic acid or a sodium salt thereof, n-tallow 3-iminodipropionate or a disodium salt thereof, n-carboxymethyl n dimethyl n-9 octadecenyl ammonium hydroxide, or n-cocoamidethyl n hydroxyethylglycine or a sodium salt thereof.

In some embodiments, the surfactant is Triton X-100, Triton X-114, Triton X-45, Tween 20, Igepal CA630, Brij 58, Brij O10, Brij L23, Pluronic L-61, Pluronic F-127, sodium dodecyl sulfate, sodium cholate, sodium deoxycholate, sodium N-lauroyl sarcosinate (NLS), Hexadecyltrimethlammonium bromide, or span 80.

In some embodiments, the salt is selected from the group consisting of aluminum chloride, aluminum phosphate, aluminum carbonate, magnesium chloride, magnesium phophate, and magnesium carbonate.

In some embodiments, the salt component includes at least two salts, wherein at least one salt is selected from the group consisting of NaCl, KCl, $NH_4Cl$, $Na_3PO_4$, $K_3PO_4$, $Na_2SO_4$, $K_2HPO_4$, $KH_2PO_4$, $Na_2HPO_4$, $NaH_2PO_4$, $(NH_4)_3PO_4$, $(NH_4)_2HPO_4$, $NH_4H_2PO_4$, potassium citrate, $(NH_4)_2SO_4$, sodium citrate, sodium acetate, magnesium acetate, sodium oxalate, sodium borate, ammonium acetate, $(NH_4)_3PO_4$, sodium formate, ammounium formate, sodium polyacrylate, $K_2CO_3$, $KHCO_3$, $Na_2CO_3$, $NaHCO_3$, $MgSO_4$, $MgCO_3$, $CaCO_3$, CsOH, $Cs_2CO_3$, $Ba(OH)_2$, $BaCO_3$, $NH_4Cl$, $NH_4OH$, tetramethyl ammonium chloride, tetrabutyl ammonium chloride, tetramethyl ammonium hydroxide, and tetrabutyl ammonium hydroxide.

In some embodiments, the polymer of the first ATPS composition or the second ATPS composition is dissolved in an aqueous solution at a concentration of 0.5-80% (w/v).

In some embodiments, the polymer of the first ATPS composition or the second ATPS composition is dissolved in an aqueous solution at a concentration of 0.2-50% (w/v).

In some embodiments, the salt component of the first ATPS composition or the second ATPS composition is dissolved in an aqueous solution at a concentration of 0.1% to 80% (w/v).

In some embodiments, the surfactant of the first ATPS composition or the second ATPS compositions is dissolved in an aqueous solution at a concentration of 0.1%-50% (w/v).

In some embodiments, the first ATPS composition or the second ATPS composition is a polymer-salt system, polymer-polymer system, or a micellar system.

In some embodiments, the first ATPS composition or the second ATPS composition is a polymer-salt system; the polymer is dissolved in an aqueous solution at a concentration of 0.5-80% (w/v); and the salt component is dissolved in an aqueous solution at a concentration of 0.1%-80% (w/v).

In some embodiments, the polymer of the first ATPS composition is dissolved in an aqueous solution at a concentration of 5-80% (w/v) and the salt component of the first ATPS composition is dissolved in an aqueous solution at a concentration of 0.1%-80% (w/v); and the polymer of the second ATPS composition is dissolved in an aqueous solution at a concentration of 0.5-30% (w/v) and the salt component of the second ATPS composition is dissolved in an aqueous solution at a concentration of 5%-60% (w/v).

In some embodiments, the first ATPS composition or the second ATPS composition further includes at least one salt at a concentration of 0.01%-10% (w/v), or at least one surfactant at a concentration of 0.01%-10% (w/v).

In some embodiments, the polymer of the first ATPS composition is polyethers, polyimines, polyacrylates, polyalkylene glycols, vinyl polymers, alkoxylated surfactants, polysaccharides, alkoxylated starch, alkoxylated cellulose, alkyl hydroxyalkyl cellulose, polyether-modified silicones, polyacrylamide, or polyacrylic acids; the salt of the first ATPS composition is NaCl, KCl, $NH_4Cl$, $Na_3PO_4$, $K_3PO_4$, $Na_2SO_4$, $K_2HPO_4$, $KH_2PO_4$, $Na_2HPO_4$, $NaH_2PO_4$, $(NH_4)_3PO_4$, $(NH_4)_2HPO_4$, $NH_4H_2PO_4$, potassium citrate, $(NH_4)_2SO_4$, sodium citrate, sodium acetate, magnesium acetate, sodium oxalate, sodium borate, ammonium acetate, $(NH_4)_3PO_4$, sodium formate, ammounium formate, sodium polyacrylate, $K_2CO_3$, $KHCO_3$, $Na_2CO_3$, $NaHCO_3$, $MgSO_4$, $MgCO_3$, $CaCO_3$, CsOH, $Cs_2CO_3$, $Ba(OH)_2$, $BaCO_3$, $NH_4OH$, tetramethyl ammonium chloride, tetrabutyl ammonium chloride, tetramethyl ammonium hydroxide, or tetrabutyl ammonium hydroxide; the polymer of the second ATPS composition is polyethers, polyimines, polyacrylates, polyalkylene glycols, vinyl polymers, alkoxylated surfactants, polysaccharides, alkoxylated starch, alkoxylated cellulose, alkyl hydroxyalkyl cellulose, polyether-modified silicones, polyacrylamide, or polyacrylic acids; and the salt of the second ATPS composition is NaCl, KCl, $NH_4Cl$, $Na_3PO_4$, $K_3PO_4$, $Na_2SO_4$, $K_2HPO_4$, $KH_2PO_4$, $Na_2HPO_4$, $NaH_2PO_4$, $(NH_4)_3PO_4$, $(NH_4)_2HPO_4$, $NH_4H_2PO_4$, potassium citrate, $(NH_4)_2SO_4$, sodium citrate, sodium acetate, magnesium acetate, sodium oxalate, sodium borate, ammonium acetate, $(NH_4)_3PO_4$, sodium formate, ammounium formate, sodium polyacrylate, $K_2CO_3$, $KHCO_3$, $Na_2CO_3$, $NaHCO_3$, $MgSO_4$, $MgCO_3$, $CaCO_3$, CsOH, $Cs_2CO_3$, $Ba(OH)_2$, $BaCO_3$, $NH_4OH$, tetramethyl ammonium chloride, tetrabutyl ammonium chloride, tetramethyl ammonium hydroxide, or tetrabutyl ammonium hydroxide. In some embodiments, the first ATPS composition or the second ATPS composition is a polymer-polymer system including at least two polymers, and each polymer is dissolved in an aqueous solution at a concentration of 0.2-50% (w/v).

In some embodiments, the first ATPS composition or the second ATPS composition further includes at least one salt at a concentration of 0.01%-10% (w/v), or at least one surfactant at a concentration of 0.01%-10% (w/v).

In some embodiments, the at least one salt includes a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium and the at least one surfactant selected from the group consisting of an anionic surfactant, a nonionic surfactant, a cationic surfactant, and an amphoteric surfactant; wherein the anionic surfactant is carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, or sodium N-lauroyl sarcosinate (NLS); the nonionic surfactant is ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, or polyoxyethylene fatty acid amides; the cationic surfactant is quaternary ammonium salts, amines with amide linkages, polyoxyethylene alkyl amines, polyoxyethylene alicyclic amines, n,n,n',n' tetrakis substituted ethylenediamines, or 2-alkyl 1-hydroxethyl 2-imidazolines; and the amphoteric surfactant is n-coco 3-aminopropionic acid or a sodium salt thereof, n-tallow 3-iminodipropionate or a disodium salt thereof, n-carboxymethyl n dimethyl n-9 octadecenyl ammonium hydroxide, or n-cocoamidethyl n hydroxyethylglycine or a sodium salt thereof.

In some embodiments, the first ATPS composition or the second ATPS composition is a micellar system including at least two surfactants, and each surfactant is dissolved in an aqueous solution at a concentration of 0.1%-50% (w/v).

In some embodiments, the first ATPS composition or the second ATPS composition further includes at least one salt at a concentration of 0.01%-30% (w/v).

In some embodiments, the at least one salt includes a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium.

In some embodiments, the polymer of the first ATPS composition is 6-40% PEG 600 (w/v); and the salt component of the first ATPS composition is 0.1-12% $K_2HPO_4$ (w/v) and 0.1-20% $KH_2PO_4$ (w/v).

In some embodiments, the polymer of the second ATPS composition is 2-20% PEG (w/v), and the salt component of the second ATPS composition is 1-50% $K_2HPO_4$ (w/v), and 0.1-40% $KH_2PO_4$ (w/v).

In some embodiments, the polymer of the first ATPS composition is 6-36% PEG 600 (w/v), and the salt component of the first ATPS composition is 2-12% $Na_2SO_4$ (w/v), 0.01-0.1M $Na_2HPO_4$, and 0.01-0.1M $NaH_2PO_4$.

In some embodiments, the polymer of the second ATPS composition is 2-12% PEG (w/v), and the salt component of the second ATPS composition is 5-20% $Na_2SO_4$ (w/v), 0.01-0.1M $Na_2HPO_4$, and 0.01-0.1M $NaH_2PO_4$.

In some embodiments, the polymer of the first ATPS composition is 20-40% PEG 1000 (w/v), and the salt component of the first ATPS composition is 0.1-8% $K_2HPO_4$ (w/v), and 0.1-12% $KH_2PO_4$ (w/v).

In some embodiments, the polymer of the second ATPS composition is 3-13% PEG (w/v), and the salt component of the second ATPS composition is 1-5% $K_2HPO_4$ (w/v), and 0.1-20% $KH_2PO_4$ (w/v).

In some embodiments, the polymer of the first ATPS composition is 10-35% PEG 3000 (w/v), and the salt component of the first ATPS composition is 0.1-6% $K_2HPO_4$ (w/v), and 0.1-8% $KH_2PO_4$ (w/v).

In some embodiments, the polymer of the second ATPS composition is 5-17% PEG (w/v), and the salt component of the second ATPS composition is 0.1-12% $K_2HPO_4$ (w/v), and 0.1-16% $KH_2PO_4$ (w/v).

In some embodiments, the polymer of the first ATPS composition is 10-32% PEG 8000 (w/v), and the salt component of the first ATPS composition is 0.1-6% $K_2HPO_4$ (w/v), and 0.1-9% $KH_2PO_4$ (w/v).

In some embodiments, the polymer of the second ATPS composition is 2-9% PEG (w/v), and the salt component of the second ATPS composition is 1-30% $K_2HPO_4$ (w/v), and 1-40% $KH_2PO_4$ (w/v).

In some embodiments, the polymer of the first ATPS composition is 40-60% PPG 425 (w/v), and the salt component of the first ATPS composition is 0.1-5% $K_2HPO_4$ (w/v), and 0.1-5% $KH_2PO_4$ (w/v).

In some embodiments, the polymer of the second ATPS composition is 5-15% PEG (w/v), and the salt component of the second ATPS composition is 0.1-20% $K_2HPO_4$ (w/v), and 0.1-20% $KH_2PO_4$ (w/v).

In some embodiments, the polymer of the first ATPS composition is 10-50% PEG-ran-PPG having an average molecular weight of about 12,000 Da and an EO:PO ratio of about 75:25 (w/v), and the salt component of the first ATPS composition is 0.1-5% $K_2HPO_4$ (w/v), and 0.1-12% $KH_2PO_4$ (w/v).

In some embodiments, the polymer of the second ATPS composition is 2-12% PEG (w/v), and the salt component of the second ATPS composition is 0.1-30% $K_2HPO_4$ (w/v), and 1-40% $KH_2PO_4$ (w/v).

In some embodiments, the polymer of the first ATPS composition is 10-32% PEG-ran-PPG having an average molecular weight of about 2,500 Da and an EO:PO ratio of about 75:25 (w/v), and the salt component of the first ATPS composition is 0.1-5% sodium citrate (w/v) and 0.1-12% citric acid (w/v).

In some embodiments, the polymer of the second ATPS composition is 3-13% PEG (w/v), and the salt component of the second ATPS composition is 0.1-20% $K_2HPO_4$ (w/v), and 1-36% $KH_2PO_4$ (w/v).

In some embodiments, the first ATPS composition includes 8-18% PEG 600 (w/v), 7-20% $K_2HPO_4$ (w/v), and 0.1-5% $KH_2PO_4$; and the second ATPS composition includes 8-25% PEG 200 (w/v), 40-50% $K_2HPO_4$ (w/v), and 4-16% $KH_2PO_4$.

In some embodiments, the first or second ATPS composition is a polymer-salt based ATPS composition including 10-25% polyvinyl pyrrolidone 3,500 Da (w/v), and 15-20% potassium phosphate (w/v).

In some embodiments, the first or second ATPS composition is a polymer-salt based ATPS composition including 25-35% polyvinyl pyrrolidone 3,500 Da (w/v), and 10-15% potassium phosphate (w/v).

In some embodiments, the first or second ATPS composition is a polymer-salt based ATPS composition including 35-50% polyvinyl pyrrolidone 3,500 Da (w/v), and 5-10% potassium phosphate (w/v).

In some embodiments, the first or second ATPS composition is a polymer-salt based ATPS composition including 2-12% PEG 600 (w/v), and 35-50% sodium phosphate (w/v).

In some embodiments, the first or second ATPS composition is a polymer-salt based ATPS composition including 12-18% PEG 600 (w/v), and 20-35% sodium phosphate (w/v).

In some embodiments, the first or second ATPS composition is a polymer-salt based ATPS composition including 18-25% PEG 600 (w/v), and 10-20% sodium phosphate (w/v).

In some embodiments, the first or second ATPS composition is a polymer-salt based ATPS composition including 5-20% polyvinyl pyrrolidone 10,000 Da (w/v), and 30-40% sodium citrate (w/v).

In some embodiments, the first or second ATPS composition is a polymer-salt based ATPS composition including 20-35% polyvinyl pyrrolidone 10,000 Da (w/v), and 20-30% sodium citrate (w/v).

In some embodiments, the first or second ATPS composition is a polymer-salt based ATPS composition including 35-50% polyvinyl pyrrolidone 10,000 Da (w/v), and 10-20% sodium citrate (w/v).

In some embodiments, the first or second ATPS composition is a polymer-salt based ATPS composition including 2-10% PEG 300 (w/v), and 49-60% sodium citrate (w/v).

In some embodiments, the first or second ATPS composition is a polymer-salt based ATPS composition including 10-18% PEG 300 (w/v), and 37-49% sodium citrate (w/v).

In some embodiments, the first or second ATPS composition is a polymer-salt based ATPS composition including 18-25% PEG 300 (w/v), and 20-37% sodium citrate (w/v).

In some embodiments, the first or second ATPS composition is a polymer-salt based ATPS composition including 10-35% PPG 425 (w/v), and 14-20% sodium sulfate (w/v).

In some embodiments, the first or second ATPS composition is a polymer-salt based ATPS composition including 35-50% PPG 425 (w/v), and 8-14% sodium sulfate (w/v).

In some embodiments, the first or second ATPS composition is a polymer-salt based ATPS composition including 55-70% PPG 425 (w/v), and 3-8% sodium sulfate (w/v).

In some embodiments, the first or second ATPS composition is a polymer-salt based ATPS composition including 5-16% PPG 425 (w/v), and 11-15% sodium polyacrylate 240,000 (w/v).

In some embodiments, the first or second ATPS composition is a polymer-salt based ATPS composition including 16-24% PPG 425 (w/v), and 5-11% sodium polyacrylate 240,000 (w/v).

In some embodiments, the first or second ATPS composition is a polymer-salt based ATPS composition including 24-40% PPG 425 (w/v), and 0.5-5% sodium polyacrylate 240,000 (w/v).

In some embodiments, the first or second ATPS composition is a polymer-salt based ATPS composition including 4-12% PEG 8000 (w/v), and 21-30% sodium carbonate (w/v).

In some embodiments, the first or second ATPS composition is a polymer-salt based ATPS composition including 12-21% PEG 8000 (w/v), and 11-21% sodium carbonate (w/v).

In some embodiments, the first or second ATPS composition is a polymer-salt based ATPS composition including 21-30% PEG 8000 (w/v), and 3-11% sodium carbonate (w/v).

In some embodiments, the first or second ATPS composition is a polymer-salt based ATPS composition including 1-5% PEG 8000 (w/v), and 14-20% sodium polyacrylate 16,000 (w/v).

In some embodiments, the first or second ATPS composition is a polymer-salt based ATPS composition including 6-11% PEG 8000 (w/v), and 7-14% sodium polyacrylate 16,000 (w/v).

In some embodiments, the first or second ATPS composition is a polymer-salt based ATPS composition including 11-15% PEG 8000 (w/v), and 2-7% sodium polyacrylate 16,000 (w/v).

In some embodiments, the first or second ATPS composition is a polymer-salt based ATPS composition including 10-25% polyvinyl alcohol 3,500 Da (w/v), and 7-10% potassium phosphate (w/v).

In some embodiments, the first or second ATPS composition is a polymer-salt based ATPS composition including 25-35% polyvinyl alcohol 3,500 Da (w/v), and 4-7% potassium phosphate (w/v).

In some embodiments, the first or second ATPS composition is a polymer-salt based ATPS composition including 35-50% polyvinyl alcohol 3,500 Da (w/v), and 2-4% potassium phosphate (w/v).

In some embodiments, the first or second ATPS composition is a polymer-salt based ATPS composition including 2-5% PEG 400 (w/v), and 34-50% potassium phosphate (w/v).

In some embodiments, the first or second ATPS composition is a polymer-salt based ATPS composition including 6-11% PEG 400 (w/v), and 22-34% potassium phosphate (w/v).

In some embodiments, the first or second ATPS composition is a polymer-salt based ATPS composition including 11-15% PEG 400 (w/v), and 10-22% potassium phosphate (w/v).

In some embodiments, the first or second ATPS composition is a polymer-salt based ATPS composition including 4-12% polyvinyl alcohol 8,000 Da (w/v), and 21-30% sodium citrate (w/v).

In some embodiments, the first or second ATPS composition is a polymer-salt based ATPS composition including 12-21% polyvinyl alcohol 8,000 Da (w/v), and 11-21% sodium citrate (w/v).

In some embodiments, the first or second ATPS composition is a polymer-salt based ATPS composition including 21-30% polyvinyl alcohol 8,000 Da (w/v), and 3-11% sodium citrate (w/v).

In some embodiments, the first or second ATPS composition is a polymer-salt based ATPS composition including 1-5% PPG 425 (w/v), and 20-30% sodium citrate (w/v).

In some embodiments, the first or second ATPS composition is a polymer-salt based ATPS composition including 6-11% PPG 425 (w/v), and 9-20% sodium citrate (w/v).

In some embodiments, the first or second ATPS composition is a polymer-salt based ATPS composition including 11-15% PPG 425 (w/v), and 0.5-9% sodium citrate (w/v).

In some embodiments, the first or second ATPS composition is a polymer-salt based ATPS composition including 2-12% polyvinyl alcohol 20,000 Da (w/v), and 21-30% sodium sulfate (w/v).

In some embodiments, the first or second ATPS composition is a polymer-salt based ATPS composition including 12-21% polyvinyl alcohol 20,000 Da (w/v), and 11-21% sodium sulfate (w/v).

In some embodiments, the first or second ATPS composition is a polymer-salt based ATPS composition including 21-30% polyvinyl alcohol 20,000 Da (w/v), and 3-11% sodium sulfate (w/v).

In some embodiments, the first or second ATPS composition is a polymer-salt based ATPS composition including 0.5-18% PEG-ran-PPG 12,000 Da (w/v), and 14-20% sodium sulfate (w/v).

In some embodiments, the first or second ATPS composition is a polymer-salt based ATPS composition including 18-35% PEG-ran-PPG 12,000 Da (w/v), and 7-14% sodium sulfate (w/v).

In some embodiments, the first or second ATPS composition is a polymer-salt based ATPS composition including 35-50% PEG-ran-PPG 12,000 Da (w/v), and 2-7% sodium sulfate (w/v).

In some embodiments, the first or second ATPS composition is a polymer-polymer based ATPS composition including 3-18% PEG 6000 (w/v), 1-6% dextran 450-650 kDa (w/v), and 5-50 mM $Na_2HPO_4/NaH_2PO_4$.

In some embodiments, the first or second ATPS composition is a polymer-polymer based ATPS composition including 1-9% PEG 6000 (w/v), and 17-25% dextran 2,200,000 Da (w/v).

In some embodiments, the first or second ATPS composition is a polymer-polymer based ATPS composition including 9-18% PEG 6000 (w/v), and 9-17% dextran 2,200,000 Da (w/v).

In some embodiments, the first or second ATPS composition is a polymer-polymer based ATPS composition including 18-25% PEG 6000 (w/v), and 0.5-9% dextran 2,200,000 Da (w/v).

In some embodiments, the first or second ATPS composition is a polymer-polymer based ATPS composition including 1-9% PEG 6000 (w/v), and 20-30% dextran 460,000 Da (w/v).

In some embodiments, the first or second ATPS composition is a polymer-polymer based ATPS composition including 9-18% PEG 6000 (w/v), and 9-20% dextran 460,000 Da (w/v).

In some embodiments, the first or second ATPS composition is a polymer-polymer based ATPS composition including 18-25% PEG 6000 (w/v), and 0.5-9% dextran 460,000 Da (w/v).

In some embodiments, the first or second ATPS composition is a polymer-polymer based ATPS composition including 1-9% PEG 6000 (w/v), and 17-25% dextran 179,000 Da (w/v).

In some embodiments, the first or second ATPS composition is a polymer-polymer based ATPS composition including 9-18% PEG 6000 (w/v), and 9-17% dextran 179,000 Da (w/v).

In some embodiments, the first or second ATPS composition is a polymer-polymer based ATPS composition including 18-25% PEG 6000 (w/v), and 0.5-9% dextran 179,000 Da (w/v).

In some embodiments, the first or second ATPS composition is a polymer-polymer based ATPS composition including 1-9% PEG 8000 (w/v), and 17-25% dextran 70,000 Da (w/v).

In some embodiments, the first or second ATPS composition is a polymer-polymer based ATPS composition including 9-18% PEG 8000 (w/v), and 9-17% dextran 70,000 Da (w/v).

In some embodiments, the first or second ATPS composition is a polymer-polymer based ATPS composition including 18-25% PEG 8000 (w/v), and 0.5-9% dextran 70,000 Da (w/v).

In some embodiments, the first or second ATPS composition is a polymer-polymer based ATPS composition including 1-16% PEG 6000 (w/v), and 33-50% dextran 3,400 Da (w/v).

In some embodiments, the first or second ATPS composition is a polymer-polymer based ATPS composition including 16-33% PEG 6000 (w/v), and 16-33% dextran 3,400 Da (w/v).

In some embodiments, the first or second ATPS composition is a polymer-polymer based ATPS composition including 33-50% PEG 6000 (w/v), and 1-16% dextran 3,400 Da (w/v).

In some embodiments, the first or second ATPS composition is a polymer-polymer based ATPS composition including 1-16% PEG 4000 (w/v), and 33-50% dextran 3,400 Da (w/v).

In some embodiments, the first or second ATPS composition is a polymer-polymer based ATPS composition including 16-33% PEG 4000 (w/v), and 16-33% dextran 3,400 Da (w/v).

In some embodiments, the first or second ATPS composition is a polymer-polymer based ATPS composition including 33-50% PEG 4000 (w/v), and 1-16% dextran 3,400 Da (w/v).

In some embodiments, the first or second ATPS composition is a polymer-polymer based ATPS composition including 1-5% PEG 20000 (w/v), and 20-30% dextran 500,000 Da (w/v).

In some embodiments, the first or second ATPS composition is a polymer-polymer based ATPS composition including 6-11% PEG 20000 (w/v), and 9-20% dextran 500,000 Da (w/v).

In some embodiments, the first or second ATPS composition is a polymer-polymer based ATPS composition including 11-15% PEG 20000 (w/v), and 0.5-9% dextran 500,000 Da (w/v).

In some embodiments, the first or second ATPS composition is a polymer-polymer based ATPS composition including 1-7% PEG 8000 (w/v), and 20-30% dextran 500,000 Da (w/v).

In some embodiments, the first or second ATPS composition is a polymer-polymer based ATPS composition including 7-14% PEG 8000 (w/v), and 9-20% dextran 500,000 Da (w/v).

In some embodiments, the first or second ATPS composition is a polymer-polymer based ATPS composition including 14-20% PEG 8000 (w/v), and 0.5-9% dextran 500,000 Da (w/v).

In some embodiments, the first or second ATPS composition is a polymer-polymer based ATPS composition including 2-16% PEG 3400 (w/v), and 20-30% dextran 500,000 Da (w/v).

In some embodiments, the first or second ATPS composition is a polymer-polymer based ATPS composition including 16-33% PEG 3400 (w/v), and 9-20% dextran 500,000 Da (w/v).

In some embodiments, the first or second ATPS composition is a polymer-polymer based ATPS composition including 33-50% PEG 3400 (w/v), and 0.5-9% dextran 500,000 Da (w/v).

In some embodiments, the first or second ATPS composition is a polymer-polymer based ATPS composition including 0.1-7% methylcellulose (w/v), and 14-20% dextran 2,200,000 Da (w/v).

In some embodiments, the first or second ATPS composition is a polymer-polymer based ATPS composition including 7-14% methylcellulose (w/v), and 7-14% dextran 2,200,000 Da (w/v).

In some embodiments, the first or second ATPS composition is a polymer-polymer based ATPS composition including 14-20% methylcellulose (w/v), and 0.1-7% dextran 2,200,000 Da (w/v).

In some embodiments, the first or second ATPS composition is a polymer-polymer based ATPS composition including 0.5-16% PolyViol 28/20 (w/v), and 33-50% dextran 2,200,000 Da (w/v).

In some embodiments, the first or second ATPS composition is a polymer-polymer based ATPS composition including 16-33% PolyViol 28/20 (w/v), and 16-33% dextran 2,200,000 Da (w/v).

In some embodiments, the first or second ATPS composition is a polymer-polymer based ATPS composition including 33-50% PolyViol 28/20 (w/v), and 0.5-16% dextran 2,200,000 Da (w/v).

In some embodiments, the first or second ATPS composition is a polymer-polymer based ATPS composition including 4-21% PEG 600 (w/v), and 58-70% PPG 400 (w/v).

In some embodiments, the first or second ATPS composition is a polymer-polymer based ATPS composition including 21-42% PEG 600 (w/v), and 36-58% PPG 400 (w/v).

In some embodiments, the first or second ATPS composition is a polymer-polymer based ATPS composition including 42-60% PEG 600 (w/v), and 4-36% PPG 400 (w/v).

In some embodiments, the first or second ATPS composition is a polymer-polymer based ATPS composition including 0.5-7% hydroxypropyl dextran 70 (w/v), and 14-20% dextran 2,200,000 Da (w/v).

In some embodiments, the first or second ATPS composition is a polymer-polymer based ATPS composition including 7-14% hydroxypropyl dextran 70 (w/v), and 7-14% dextran 2,200,000 Da (w/v).

In some embodiments, the first or second ATPS composition is a polymer-polymer based ATPS composition including 14-20% hydroxypropyl dextran 70 (w/v), and 0.5-7% dextran 2,200,000 Da (w/v).

In some embodiments, the first or second ATPS composition is a polymer-polymer based ATPS composition including 0.5-7% PEG 8000 (w/v), and 20-30% hydroxypropyl starch 60-70 kDa (w/v).

In some embodiments, the first or second ATPS composition is a polymer-polymer based ATPS composition including 7-14% PEG 8000 (w/v), and 10-20% hydroxypropyl starch 60-70 kDa (w/v).

In some embodiments, the first or second ATPS composition is a polymer-polymer based ATPS composition including 14-20% PEG 8000 (w/v), and 1-10% hydroxypropyl starch 60-70 kDa (w/v).

In some embodiments, the first or second ATPS composition is a micellar based ATPS composition including 5-17% $(C_2H_4O)_{(4.5)}C_{14}H_{22}O$ (Triton X-45) and 60-90% $(C_2H_4O)_{(9-10)}C_{14}H_{22}O$ (Triton X-114).

In some embodiments, the first or second ATPS composition is a micellar based ATPS composition including 10-20% Triton X-100 (w/v).

In some embodiments, the first or second ATPS composition is a micellar based ATPS composition including 20-30% Triton X-100 (w/v).

In some embodiments, the first or second ATPS composition is a micellar based ATPS composition including 30-40% Triton X-100 (w/v).

In some embodiments, the first or second ATPS composition is a micellar based ATPS composition including 5-18% Triton X-114 (w/v).

In some embodiments, the first or second ATPS composition is a micellar based ATPS composition including 18-29% Triton X-114 (w/v).

In some embodiments, the first or second ATPS composition is a micellar based ATPS composition including 29-40% Triton X-114 (w/v).

In some embodiments, the first or second ATPS composition is a micellar based ATPS composition including 3-19% decy tetraethylene glycol ether (C10E4) (w/v).

In some embodiments, the first or second ATPS composition is a micellar based ATPS composition including 19-34% decy tetraethylene glycol ether (C10E4) (w/v).

In some embodiments, the first or second ATPS composition is a micellar based ATPS composition including 34-50% decy tetraethylene glycol ether (C10E4) (w/v).

In some embodiments, the first or second ATPS composition is a micellar based ATPS composition including 1-10% Pluronic F68 (MW 8,400 Da, $EO_{82}$-$PO_{31}$-$EO_{82}$) (w/v), and 14-20% potassium phosphate (w/v).

In some embodiments, the first or second ATPS composition is a micellar based ATPS composition including 10-20% Pluronic F68 (w/v), and 7-14% potassium phosphate (w/v).

In some embodiments, the first or second ATPS composition is a micellar based ATPS composition including 20-30% Pluronic F68 (w/v), and 1-7% potassium phosphate (w/v).

In some embodiments, the first or second ATPS composition is a micellar based ATPS composition including 5-21% Pluronic 17R4 (MW 2,650 Da, $PO_{14}$-$EO_{24}$-$PO_{14}$) (w/v), and 7-10% potassium phosphate (w/v).

In some embodiments, the first or second ATPS composition is a micellar based ATPS composition including 21-42% Pluronic 17R4 (w/v), and 3-7% potassium phosphate (w/v).

In some embodiments, the first or second ATPS composition is a micellar based ATPS composition including 42-60% Pluronic 17R4 (w/v), and 1-3% potassium phosphate (w/v).

In some embodiments, the first or second ATPS composition is a micellar based ATPS composition including 2-21% Pluronic L-35 (MW 1,900 Da, $EO_{10}$-$PO_{16}$-$EO_{10}$) (w/v), and 14-20% sodium sulfate (w/v).

In some embodiments, the first or second ATPS composition is a micellar based ATPS composition including 21-42% Pluronic L-35 (w/v), and 7-14% sodium sulfate (w/v).

In some embodiments, the first or second ATPS composition is a micellar based ATPS composition including 42-60% Pluronic L-35 (w/v), and 1-7% sodium sulfate (w/v).

In some embodiments, the first ATPS composition and/or the second ATPS composition are selected from Table 1.0.

In some embodiments, the first ATPS composition or the second ATPS composition further includes 0.5-2 mM ethylenediaminetetraacetic acid (EDTA).

In some embodiments, the method further includes the step of analyzing the final solution from step (f) using a method selected from the group consisting of qPCR, ddPCR, qubit, ELISA, NGS sequencer, bisulfide, RT-PCR, sanger sequencing, nanodrop, nanopore sequencing, nucleic acid sequencing, and PCR-based assays.

In some embodiments, the target analyte is a biomarker indicating the presence or risk of a medical condition or disease in a patient, wherein the medical condition or disease is an infectious disease, cancer, or a genetic disease.

In some embodiments, the clinical biological sample is a bulk fluid sample having a volume >10 mL and further includes the following step before step (a): dividing the bulk fluid sample into at least two aliquots of a sample solution; wherein each aliquot is separately combined with the first ATPS in steps (a) and optionally the collected target rich phase from step (b) is separately combined with the second ATPS in step (c) to form each aliquot's target rich phase.

In some embodiments, each aliquot's target-rich phase from step (b) or each aliquot's second target-rich phase from step (c) is combined together to form a final target rich phase for step (d).

In some embodiments, the bulk fluid sample is urine.

In some embodiments, provided is a method of treating cancer or infectious disease in a patient in need thereof, including the steps of: (i) obtaining a clinical biological sample from the patient; (ii) concentrating and purifying at least one target analyte from the clinical biological sample according to the preceding embodiments; (iii) analyzing the final solution; and (iv) treating the patient if the information obtained from the target analyte indicates that the patient has cancer or is at risk of developing cancer.

In some embodiments, the cancer is CNS cancer, breast cancer, bladder cancer, pancreatic cancer, lung cancer, melanomas, colon cancer, hematopoietic cancer or ovarian cancer and wherein the infectious disease is HPV.

In some embodiments, the target analyte is transrenal cFDNA or ctDNA, and wherein the cancer is systemic cancer.

In some embodiments, the target analyte is urogenital cFDNA or ctDNA, and wherein the cancer is urogenital cancer.

In some embodiments, the target analyte is bladder cancer DNA and the medical condition or disease is bladder cancer.

In some embodiments, the target analyte is HPV viral RNA or HPV viral DNA, and the medical condition or disease is HPV.

In some embodiments, provided is a kit including an ATPS composition which includes a polymer, a salt component including at least one salt, a binding buffer, and a solid phase medium from any one of the preceding embodiments.

In some embodiments, provided is a kit including a first ATPS composition, a second ATPS composition, a binding buffer, and a solid phase medium, according to any one of the preceding embodiments.

In some embodiments, the polymer is dissolved in an aqueous solution at a concentration of 0.5%-80% (w/v); and the salt is dissolved in an aqueous solution at a concentration of 0.1%-80% (w/v).

In some embodiments, the first ATPS composition includes said polymer dissolved in an aqueous solution at a concentration of 5%-80% (w/v) and said salt dissolved an aqueous solution at a concentration of 0.1%-80% (w/v); and wherein the second ATPS composition includes said polymer dissolved in an aqueous solution at a concentration of 0.5%-30% (w/v) and said salt dissolved in an aqueous solution at a concentration of 5%-60% (w/v).

In some embodiments, the polymer is at a concentration of 0.5-80% (w/v) of the first ATPS and/or the second ATPS. In some embodiments, the polymer is at a concentration of 0.5-30% (w/v) of the first ATPS and/or the second ATPS. In some embodiments, the polymer is at a concentration of 5-60% (w/v) of the first ATPS and/or the second ATPS. In some embodiments, the polymer is at a concentration of 12-50% (w/v) of the first ATPS and/or the second ATPS.

In some embodiments, the salt is at a concentration of 0.1%-80% (w/v) of the first ATPS and/or the second ATPS. In some embodiments, the salt is at a concentration of 5%-60% (w/v) of the first ATPS and/or the second ATPS. In some embodiments, the salt is at a concentration of 0.1%-50% (w/v) of the first ATPS and/or the second ATPS. In some embodiments, the salt is at a concentration of 0.1%-20% (w/v) of the first ATPS and/or the second ATPS. In some embodiments, the salt is at a concentration of 0.01%-30% (w/v). In some embodiments, the salt is at a concentration of 0.01%-10% (w/v) of the first ATPS and/or the second ATPS.

In some embodiments, the surfactant is at a concentration of 0.1-90% (w/v) or 0.1-50% (w/v) of the first ATPS and/or the second ATPS. In some embodiments, the surfactant is at a concentration of 0.01%-10% (w/v) of the first ATPS and/or the second ATPS.

In some embodiments, the first ATPS composition is polymer-salt based system, comprising at least one polymer at a concentration of 5-80% (w/v) and at least one salt at a concentration of 0.1-80% (w/v). In some embodiments, the first ATPS composition comprises at least one polymer at a concentration of 5-60% (w/v) and at least one salt at a concentration of 0.5-50% (w/v). In some embodiments, the first ATPS composition comprises at least one polymer at a concentration of 12-50% (w/v) and at least one salt a concentration of 0.1-20% (w/v). In some embodiments, the first ATPS composition further comprises at least one surfactant at a concentration of 0.01%-10% (w/v).

In some embodiments, the second ATPS composition comprises at least one polymer at a concentration of 0.5-30% (w/v) and at least one salt at a concentration of 5-60% (w/v). In some embodiments, the second ATPS composition comprises at least one polymer at a concentration of 1-6% (w/v) and at least one salt at a concentration of 10-50% (w/v). In some embodiments, the second ATPS composition further comprises at least one surfactant at a concentration of 0.01%-10% (w/v).

In some embodiments, the first ATPS composition is a polymer-salt system, comprising at least one polymer at a concentration of 0.5-30% (w/v) and at least one salt at a concentration of 5-60% (w/v). In some embodiments, the first ATPS composition comprises at least one polymer at a concentration of 1-6% (w/v) and at least one salt at a concentration of 10-50% (w/v). In some embodiments, the first ATPS composition further comprises at least one surfactant at a concentration of 0.01%-10% (w/v).

In some embodiments, the second ATPS composition comprises at least one polymer at a concentration of 5-80% (w/v) and at least one salt at a concentration of 0.1-80% (w/v). In some embodiments, the second ATPS composition comprises at least one polymer at a concentration of 5-60% (w/v) and at least one salt at a concentration of 0.5-50% (w/v). In some embodiments, the second ATPS composition comprises at least one polymer at a concentration of 12-50% (w/v) and at least one salt at a concentration of 0.1-20% (w/v). In some embodiments, the second ATPS composition further comprises at least one surfactant at a concentration of 0.01%-10% (w/v).

In some embodiments, the first ATPS composition is a polymer-polymer system, comprising at least two polymers, and each polymer is dissolved in an aqueous solution at a concentration of 0.2-50% (w/v). In some embodiments, the first ATPS composition further comprises at least one salt at a concentration of 0.01%-10% (w/v). In some embodiments, the first ATPS composition further comprises at least one surfactant at a concentration of 0.01%-10% (w/v).

In some embodiments, the first ATPS composition is a micellar system, comprising at least two surfactants, and each surfactant is dissolved in an aqueous solution at a concentration of 0.1-90% (w/v). In some embodiments, the first ATPS composition further comprises at least one salt at a concentration of 0.01%-30% (w/v).

In some embodiments, the polymer of the first ATPS composition or the second ATPS composition is dissolved in an aqueous solution at a concentration of 0.5-80% (w/v), 0.5-60% (w/v), 5-80% (w/v), 5-60% (w/v), 12-50% (w/v), or 0.5-30% (w/v)).

In some embodiments, the salt component of the first ATPS composition or the second ATPS composition is dissolved in an aqueous solution at a concentration of 0.1%-80% (w/v), 0.5-50% (w/v), 0.1-20% (w/v), 5-60% (w/v), or 10-50% (w/v).

In some embodiments, the binding buffer comprises a 2M-7M solution of guanidinium. In some embodiments, the binding buffer further comprises a polymer at a concentration of 5-20% (w/v).

In some embodiments, provided is a kit comprising an ATPS composition comprising a polymer, a salt component comprising at least one salt, a binding buffer, and a solid phase medium from any one of the preceding embodiments.

Although the description referred to particular embodiments, the disclosure should not be construed as limited to the embodiments set forth herein.

Other example embodiments are discussed herein.

EXAMPLES

Provided herein are examples that describe in more detail certain embodiments of the present disclosure. The examples provided herein are merely for illustrative purposes and are not meant to limit the scope of the invention in any way. All references given below and elsewhere in the present application are hereby included by reference.

Example Workflows for Concentrating and Purifying Target Analyte(s) from a Clinical Biological Sample Provided herein are example workflows for concentrating and purifying target analyte(s) (such as target nucleic acids) from a clinical biological sample using Aqueous Two-Phase System (ATPS) and solid phase medium. Examples ATPS compositions for use in the first ATPS and/or the second ATPS steps are summarized in Table 1.0. These examples are presented for illustrative purposes only and are not intended to be an exhaustive list of all possible embodiments of the invention.

TABLE 1.0

Example ATPS compositions. All concentrations are shown in w/v ratio unless otherwise noted.

| ATPS | Composition |
|---|---|
| 1 | 3-18% PEG 6000, 1-6% dextran 450-650 kDa, 5-50 mM $Na_2HPO_4/NaH_2PO_4$ |
| 2 | 1-9% PEG 6000, 17-25% dextran 2,200,000 Da |
| 3 | 9-18% PEG 6000, 9-17% dextran 2,200,000 Da |
| 4 | 18-25% PEG 6000, 0.5-9% dextran 2,200,000 Da |
| 5 | 1-9% PEG 6000, 20-30% dextran 460,000 Da |
| 6 | 9-18% PEG 6000, 9-20% dextran 460,000 Da |
| 7 | 18-25% PEG 6000, 0.5-9% dextran 460,000 Da |
| 8 | 1-9% PEG 6000, 17-25% dextran 179,000 Da |
| 9 | 9-18% PEG 6000, 9-17% dextran 179,000 Da |
| 10 | 18-25% PEG 6000, 0.5-9% dextran 179,000 Da |
| 11 | 1-9% PEG 8000, 17-25% dextran 70,000 Da |
| 12 | 9-18% PEG 8000, 9-17% dextran 70,000 Da |
| 13 | 18-25% PEG 8000, 0.5-9% dextran 70,000 Da |
| 14 | 1-16% PEG 6000, 33-50% dextran 3,400 Da |
| 15 | 16-33% PEG 6000, 16-33% dextran 3,400 Da |
| 16 | 33-50% PEG 6000, 1-16% dextran 3,400 Da |
| 17 | 1-16% PEG 4000, 33-50% dextran 3,400 Da |
| 18 | 16-33% PEG 4000, 16-33% dextran 3,400 Da |
| 19 | 33-50% PEG 4000, 1-16% dextran 3,400 Da |
| 20 | 1-5% PEG 20000, 20-30% dextran 500,000 Da |
| 21 | 6-11% PEG 20000, 9-20% dextran 500,000 Da |
| 22 | 11-15% PEG 20000, 0.5-9% dextran 500,000 Da |
| 23 | 1-7% PEG 8000, 20-30% dextran 500,000 Da |

TABLE 1.0-continued

Example ATPS compositions. All concentrations are shown in w/v ratio unless otherwise noted.

| ATPS | Composition |
|---|---|
| 24 | 7-14% PEG 8000, 9-20% dextran 500,000 Da |
| 25 | 14-20% PEG 8000, 0.5-9% dextran 500,000 Da |
| 26 | 2-16% PEG 3400, 20-30% dextran 500,000 Da |
| 27 | 16-33% PEG 3400, 9-20% dextran 500,000 Da |
| 28 | 33-50% PEG 3400, 0.5-9% dextran 500,000 Da |
| 29 | 0.1-7% methylcellulose[1], 14-20% dextran 2,200,000 Da |
| 30 | 7-14% methylcellulose[1], 7-14% dextran 2,200,000 Da |
| 31 | 14-20% methylcellulose[1], 0.1-7% dextran 2,200,000 Da |
| 32 | 0.5-16% PolyViol 28/20[2], 33-50% dextran 2,200,000 Da |
| 33 | 16-33% PolyViol 28/20[2], 16-33% dextran 2,200,000 Da |
| 34 | 33-50% PolyViol 28/20[2], 0.5-16% dextran 2,200,000 Da |
| 35 | 4-21% PEG 600, 58-70% PPG 400 |
| 36 | 21-42% PEG 600, 36-58% PPG 400 |
| 37 | 42-60% PEG 600, 4-36% PPG 400 |
| 38 | 0.5-7% hydroxypropyl dextran 70, 14-20% dextran 2,200,000 Da |
| 39 | 7-14% hydroxypropyl dextran 70, 7-14% dextran 2,200,000 Da |
| 40 | 14-20% hydroxypropyl dextran 70, 0.5-7% dextran 2,200,000 Da |
| 41 | 0.5-7% PEG 8000, 20-30% hydroxypropyl starch 60-70 kDa |
| 42 | 7-14% PEG 8000, 10-20% hydroxypropyl starch 60-70 kDa |
| 43 | 14-20% PEG 8000, 1-10% hydroxypropyl starch 60-70 kDa |
| 44 | 10-20% Triton X-100 |
| 45 | 20-30% Triton X-100 |
| 46 | 30-40% Triton X-100 |
| 47 | 5-18% Triton X-114 |
| 48 | 18-29% Triton X-114 |
| 49 | 29-40% Triton X-114 |
| 50 | 60-90% Triton X-114, 5-17% Triton X-45 |
| 51 | 3-19% C10E4 (decy tetraethylene glycol ether) |
| 52 | 19-34% C10E4 (decy tetraethylene glycol ether) |
| 53 | 34-50% C10E4 (decy tetraethylene glycol ether) |
| 54 | 1-10% Pluronic F68, 14-20% potassium phosphate |
| 55 | 10-20% Pluronic F68, 7-14% potassium phosphate |
| 56 | 20-30% Pluronic F68, 1-7% potassium phosphate |
| 57 | 5-21% Pluronic 17R4, 7-10% potassium phosphate |
| 58 | 21-42% Pluronic 17R4, 3-7% potassium phosphate |
| 59 | 42-60% Pluronic 17R4, 1-3% potassium phosphate |
| 60 | 2-21% Pluronic L-35, 14-20% sodium sulfate |
| 61 | 21-42% Pluronic L-35, 7-14% sodium sulfate |
| 62 | 42-60% Pluronic L-35, 1-7% sodium sulfate |
| 63 | 8-18% PEG 600, 7-20% $K_2HPO_4$, 0.1-5% $KH_2PO_4$ |
| 64 | 8-30% PEG 600, 1-6% $K_2HPO_4$, 12-20% $KH_2PO_4$ |
| 65 | 8-25% PEG 200, 40-50% $K_2HPO_4$, 4-16% $KH_2PO_4$ |
| 66 | 8-18% PEG 600, 7-20% $K_2HPO_4$, 0.1-5% $KH_2PO_4$ |
| 67 | 6-18% PEG 600, 2-12% $K_2HPO_4$, 0.1-5% $KH_2PO_4$, 0.01-10% (v/v) Triton X-114 |
| 68 | 6-18% PEG 600, 2-12% $K_2HPO_4$, 0.1-5% $KH_2PO_4$ |
| 69 | 5-20% PEG 600, 0.1-6% $K_2HPO_4$, 6-18% $KH_2PO_4$ |
| 70 | 5-20% PEG 600, 2-12% $K_2HPO_4$, 0.1-5% $KH_2PO_4$ |
| 71 | 5-17% PEG 200, 3-12% $K_2HPO_4$, 0.1-5% $KH_2PO_4$ |
| 72 | 5-17% PEG 200, 0.1-4% $K_2HPO_4$, 5-16% $KH_2PO_4$ |
| 73 | 5-15% PEG 200, 3-13% $K_2HPO_4$, 0.1-5% $KH_2PO_4$ |
| 74 | 5-15% PEG 200, 0.1-4% $K_2HPO_4$, 6-20% $KH_2PO_4$ |
| 75 | 36-60% PPG 425, 0.1-5% $K_2HPO_4$, 0.1-3% $KH_2PO_4$ |
| 76 | 40-60% PPG 425, 0.1-4% $K_2HPO_4$, 0.1-5% $KH_2PO_4$ |
| 77 | 40-50% PPG 425, 0.1-4% $K_2HPO_4$, 0.1-5% $KH_2PO_4$ |
| 78 | 36-60% PPG 425, 0.1-3% $K_2HPO_4$, 0.1-5% $KH_2PO_4$ |
| 79 | 3-20% PEG 200, 10-30% $K_2HPO_4$, 1-9% $KH_2PO_4$ |
| 80 | 3-13% PEG 200, 3-12% $K_2HPO_4$, 0.1-5% $KH_2PO_4$ |
| 81 | 3-13% PEG 200, 1-4% $K_2HPO_4$, 5-20% $KH_2PO_4$ |
| 82 | 3-13% PEG 200, 13-20% $K_2HPO_4$, 1-7% $KH_2PO_4$ |
| 83 | 3-13% PEG 200, 0.1-12% $K_2HPO_4$, 16-36% $KH_2PO_4$ |
| 84 | 3-12% PEG 200, 2-8% $K_2HPO_4$, 20-40% $KH_2PO_4$ |
| 85 | 3-12% PEG 200, 10-30% $K_2HPO_4$, 1-7% $KH_2PO_4$ |
| 86 | 30-50% PEG-ran-PPG[4], 0.1-5% $K_2HPO_4$, 0.1-3% $KH_2PO_4$ |
| 87 | 2-9% PEG 200, 8-20% $K_2HPO_4$, 1-7% $KH_2PO_4$ |
| 88 | 2-9% PEG 200, 5-20% $K_2HPO_4$, 0.1-4% $KH_2PO_4$ |
| 89 | 2-9% PEG 200, 2-8% $K_2HPO_4$, 20-40% $KH_2PO_4$ |
| 90 | 2-9% PEG 200, 2-8% $K_2HPO_4$, 16-36% $KH_2PO_4$ |
| 91 | 2-9% PEG 200, 1-8% $K_2HPO_4$, 20-40% $KH_2PO_4$ |
| 92 | 2-9% PEG 200, 1-7% $K_2HPO_4$, 8-32% $KH_2PO_4$ |
| 93 | 2-9% PEG 200, 10-30% $K_2HPO_4$, 1-7% $KH_2PO_4$ |
| 94 | 2-8% PEG 200, 4-13% $K_2HPO_4$, 0.1-5% $KH_2PO_4$ |
| 95 | 2-8% PEG 200, 1-5% $K_2HPO_4$, 6-20% $KH_2PO_4$ |
| 96 | 2-12% PEG 200, 5-20% $Na_2SO_4$, 0.01-0.1M $Na_2HPO_4$, 0.01-0.1M $NaH_2PO_4$ |

TABLE 1.0-continued

Example ATPS compositions. All concentrations are shown in w/v ratio unless otherwise noted.

| ATPS | Composition |
|---|---|
| 97 | 20-40% PEG 600, 2-12% $K_2HPO_4$, 0.1-5% $KH_2PO_4$ |
| 98 | 20-40% PEG 600, 0.1-4% $K_2HPO_4$, 2-9% $KH_2PO_4$ |
| 99 | 20-40% PEG 1000, 1-12% $K_2HPO_4$, 0.1-3% $KH_2PO_4$ |
| 100 | 20-40% PEG 1000, 0.1-4% $K_2HPO_4$, 3-12% $KH_2PO_4$ |
| 101 | 20-40% PEG 1000, 0.1-4% $K_2HPO_4$, 2-9% $KH_2PO_4$ |
| 102 | 16-36% PEG 600, 2-12% $Na_2SO_4$, 0.01-0.1M $Na_2HPO_4$, 0.01-0.1M $NaH_2PO_4$ |
| 103 | 1-6% PEG 200, 3-12% $K_2HPO_4$, 25-50% $KH_2PO_4$ |
| 104 | 1-6% PEG 200, 0.1-5% $K_2HPO_4$, 6-36% $KH_2PO_4$ |
| 105 | 1-6% PEG 200, 0.1-5% $K_2HPO_4$, 5-20% $KH_2PO_4$ |
| 106 | 11-33% PEG 3000, 0.1-6% $K_2HPO_4$, 0.1-3% $KH_2PO_4$ |
| 107 | 11-33% PEG 3000, 0.1-4% $K_2HPO_4$, 1-8% $KH_2PO_4$ |
| 108 | 10-32% PEG-ran-PPG[3], 0.1-4% citric acid, 3-12% sodium citrate |
| 109 | 10-32% PEG-ran-PPG[3], 0.1-4% citric acid, 2-9% sodium citrate |
| 110 | 10-32% PEG-ran-PPG[3], 0.1-3% citric acid, 1-6% sodium citrate |
| 111 | 10-32% PEG-ran-PPG[3], 0.1-3% citric acid, 0.1-4% sodium citrate |
| 112 | 10-32% PEG 8000, 0.1-6% $K_2HPO_4$, 0.1-3% $KH_2PO_4$ |
| 113 | 10-32% PEG 8000, 0.1-4% $K_2HPO_4$, 2-8% $KH_2PO_4$ |
| 114 | 10-32% PEG 8000, 0.1-4% $K_2HPO_4$, 0.1-9% $KH_2PO_4$ |
| 115 | 10-30% PEG-ran-PPG[4], 0.1-4% $K_2HPO_4$, 0.1-6% $KH_2PO_4$ |
| 116 | 10-30% PEG-ran-PPG[4], 0.1-3% $K_2HPO_4$, 2-8% $KH_2PO_4$ |
| 117 | 10-25% polyvinyl pyrrolidone 3,500 Da, 15-20% potassium phosphate |
| 118 | 25-35% polyvinyl pyrrolidone 3,500 Da, 10-15% potassium phosphate |
| 119 | 35-50% polyvinyl pyrrolidone 3,500 Da, 5-10% potassium phosphate |
| 120 | 2-12% PEG 600, 35-50% sodium phosphate |
| 121 | 12-18% PEG 600, 20-35% sodium phosphate |
| 122 | 18-25% PEG 600, 10-20% sodium phosphate |
| 123 | 5-20% polyvinyl pyrrolidone 10,000 Da, 30-40% sodium citrate |
| 124 | 20-35% polyvinyl pyrrolidone 10,000 Da, 20-30% sodium citrate |
| 125 | 35-50% polyvinyl pyrrolidone 10,000 Da, 10-20% sodium citrate |
| 126 | 2-10% PEG 300, 49-60% sodium citrate |
| 127 | 10-18% PEG 300, 37-49% sodium citrate |
| 128 | 18-25% PEG 300, 20-37% sodium citrate |
| 129 | 10-35% PPG 425, 14-20% sodium sulfate |
| 130 | 35-50% PPG 425, 8-14% sodium sulfate |
| 131 | 55-70% PPG 425, 3-8% sodium sulfate |
| 132 | 5-16% PPG 425, 11-15% sodium polyacrylate 240,000 |
| 133 | 16-24% PPG 425, 5-11% sodium polyacrylate 240,000 |
| 134 | 24-40% PPG 425, 0.5-5% sodium polyacrylate 240,000 |
| 135 | 4-12% PEG 8000, 21-30% sodium carbonate |
| 136 | 12-21% PEG 8000, 11-21% sodium carbonate |
| 137 | 21-30% PEG 8000, 3-11% sodium carbonate |
| 138 | 1-5% PEG 8000, 14-20% sodium polyacrylate 16,000 |
| 139 | 6-11% PEG 8000, 7-14% sodium polyacrylate 16,000 |
| 140 | 11-15% PEG 8000, 2-7% sodium polyacrylate 16,000 |
| 141 | 10-25% polyvinyl alcohol 3,500 Da, 7-10% potassium phosphate |
| 142 | 25-35% polyvinyl alcohol 3,500 Da, 4-7% potassium phosphate |
| 143 | 35-50% polyvinyl alcohol 3,500 Da, 2-4% potassium phosphate |
| 144 | 2-5% PEG 400, 34-50% potassium phosphate |
| 145 | 6-11% PEG 400, 22-34% potassium phosphate |
| 146 | 11-15% PEG 400, 10-22% potassium phosphate |
| 147 | 4-12% polyvinyl alcohol 8,000 Da, 21-30% sodium citrate |
| 148 | 12-21% polyvinyl alcohol 8,000 Da, 11-21% sodium citrate |
| 149 | 21-30% polyvinyl alcohol 8,000 Da, 3-11% sodium citrate |
| 150 | 1-5% PPG 425, 20-30% sodium citrate |
| 151 | 6-11% PPG 425, 9-20% sodium citrate |
| 152 | 11-15% PPG 425, 0.5-9% sodium citrate |
| 153 | 2-12% polyvinyl alcohol 20,000 Da, 21-30% sodium sulfate |
| 154 | 12-21% polyvinyl alcohol 20,000 Da, 11-21% sodium sulfate |
| 155 | 21-30% polyvinyl alcohol 20,000 Da, 3-11% sodium sulfate |
| 156 | 0.5-18% PEG-ran-PPG 12,000 Da, 14-20% sodium sulfate |
| 157 | 18-35% PEG-ran-PPG 12,000 Da, 7-14% sodium sulfate |
| 158 | 35-50% PEG-ran-PPG 12,000 Da, 2-7% sodium sulfate |

[1] provided as 4000 cP @, 2% solution
[2] polyvinyl alcohol characterized as 97-99% hydrolysis, viscosity cP (@, 4% solution @ 20° C.) = 20-30, and degree of polymerization = 1700-2000
[3] PEG-ran-PPG having an average molecular weight of about 2,500 Da and an EO:PO ratio of about 75:25
[4] PEG-ran-PPG having an average molecular weight of about 12,000 Da and an EO:PO ratio of about 75:25

Example 1a Bead Purification

Now referring to FIG. 1A, which shows an example workflow of bead purification (also referred as "beads purification", "magnetic beads workflow" or "magnetic beads purification" in some embodiments) integrated with prior ATPS steps. In this embodiment, in the first optional lysis step 111, suitable lysis buffer is added into the sample (e.g. blood, plasma, serum, cerebrospinal fluid, urine, saliva, fecal matter, tear, sputum, nasopharyngeal mucus, vaginal discharge or penile discharge) for lysing the cells in the sample and releasing the biomolecules into the lysis buffer solution. The lysed sample undergoes two sequential aqueous two-phase systems (ATPSs) to isolate and concentrate DNA.

In step 112, the lysed sample is mixed with a first ATPS. The mixture is vortexed vigorously, and then centrifuged such that it is separated into a top phase and bottom phase. In some embodiments, the top phase is a target-rich phase (also referred to as "first target-rich phase") containing the target analyte. In some embodiments, the bottom phase is a target-rich phase containing the target analyte.

In step 113, all target-rich phase from the step 112 where DNA partitions to is transferred into a second ATPS ($2^{nd}$ ATPS) and thoroughly mixed. The mixture is vortexed, and then centrifuged such that it is separated into a top phase and a bottom phase. In some embodiments, the top phase is a second target-rich phase containing the target analyte. In some embodiments, the bottom phase is a second target-rich phase containing the target analyte.

In step 114, the second target-rich phase from the step 113 where target DNA partitions to is extracted into an empty microcentrifuge tube. Binding buffer (such as those as described in Examples 2a-5c below) is added into the tube and mixed well with the top phase from the step 113 as well as a plurality of beads (such as those as described in Table 1.1) which are also added into the tube to form a solid phase extraction complex (i.e., beads-analyte complex in this example). The mixture containing the beads-analyte complex is incubated for a certain time and is then spun down and the beads-analyte complex are immobilized. Supernatant is discarded without disturbing the beads-analyte complex. In some embodiments, the beads-analyte complex are immobilized at tube wall by a magnetic rack.

In step 115, the beads-analyte complex is further purified by washing with an appropriate solvent and discarding the supernatant containing impurities. In some embodiments, the appropriate solvent is a binding buffer or a washing buffer. The step 115 is optionally repeated.

In step 116, the beads-analyte complex is then dried with the cap opened. The beads-analyte complex is then resuspended in suitable eluting solution (e.g., an elution buffer) and mixed sufficiently to release the beads from the beads-analyte complex. The beads are then immobilized, and the final solution comprising the purified target DNA is collected for further use.

TABLE 1.1

Examples of magnetic beads.

| Manufacturer | Bead Name | Specification |
|---|---|---|
| G-Biosciences | 786-915 | Silica ($SiO_2$) |
| Biochain | L5011001 | Silica ($SiO_2$) |
| MagQu | MF-SIL-5024 | Silica ($SiO_2$) |
| MagQu | MF-SIL-5010 | Silica ($SiO_2$) |
| G-Biosciences | 786-915 | Silica ($SiO_2$) |

TABLE 1.1-continued

Examples of magnetic beads.

| Manufacturer | Bead Name | Specification |
| --- | --- | --- |
| Biochain | L5011001 | Silica ($SiO_2$) |
| Luna nanotech | NMG-101 | Silica ($SiO_2$) |
| Cambrian bioworks | CBWD001 | Silica ($SiO_2$) |
| Bioclone | FF-103 | Silica ($SiO_2$) |
| Chemagen | M-PVA 011 | Unmodified |
| Chemagen | M-PVA 012 | Unmodified |
| Chemagen | M-PVA 021 | Highly carboxylated |
| Chemagen | M-PVA 022 | Highly carboxylated |
| Omega Biotek | Mag-Bind ® Particles CH | Silica ($SiO_2$) |
| Thermofisher | Dynabeads ™ MyOne ™ SILANE | Silica-liked coated |
| Ocean Nanotech | PureBind T Bead | Silica ($SiO_2$) |
| Ocean Nanotech | PureBind M Bead | Silica ($SiO_2$) |
| MagQu | MF-NHH-3000 | Amine ($-NH_2$) |
| MagQu | MF-Dex-3000 | Hydroxyl ($-OH$) |
| Avanbio | fe10002-cf | Carboxyl |
| Avanbio | fe03001 | Carboxyl |

Example 1b Column Purification

Figure 1B:
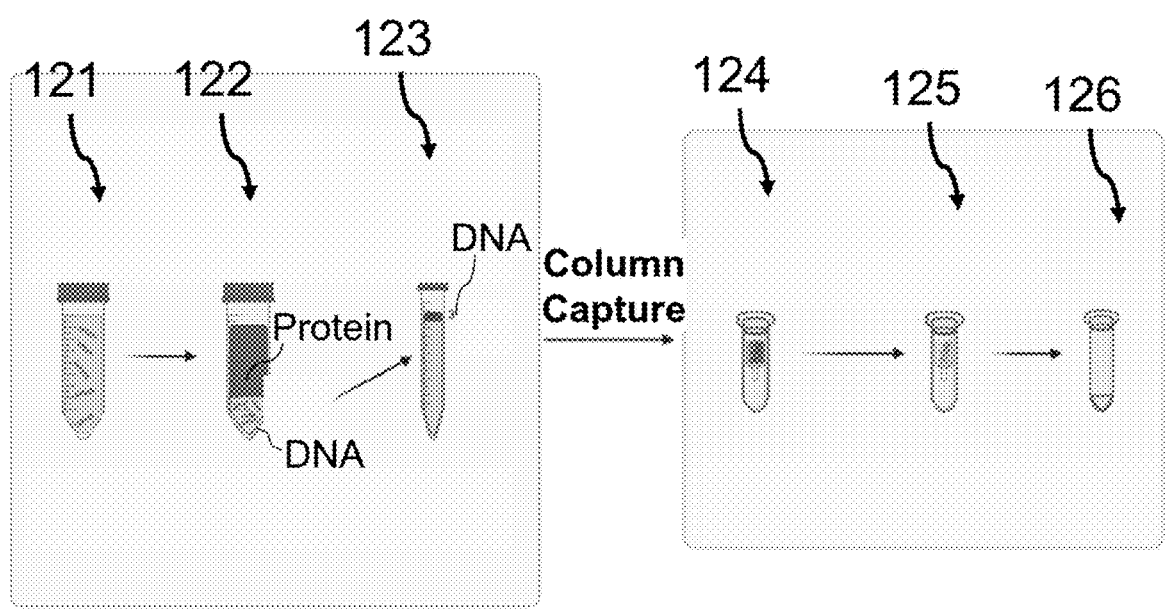
FIG. 1B shows an example workflow of column purification according to an example embodiment described in Example 1b.

Now referring to FIG. 1B, which shows an example workflow of column purification (also referred as "spin column purification" or "spin column workflow" in some embodiments) integrated with prior ATPS steps. In this embodiment, in the first optional lysis step 121, suitable lysis buffer is added into the sample (e.g. blood, plasma, serum, cerebrospinal fluid, urine, saliva, fecal matter, tear, sputum, nasopharyngeal mucus, vaginal discharge or penile discharge) for lysing the cells in the sample and releasing the biomolecules into the lysis buffer solution. The lysed sample undergoes two sequential aqueous two-phase systems (ATPSs) to isolate and concentrate DNA.

In step 122, the lysed sample is mixed with a first ATPS. The mixture is vortexed vigorously, and then centrifuged such that it is separated into a top phase and bottom phase. In some embodiments, the top phase is a target-rich phase (also referred to as "first target-rich phase") containing the target analyte. In some embodiments, the bottom phase is a target-rich phase containing the target analyte.

In step 123, all target-rich phase from the step 122 where DNA partitions to is transferred into a second ATPS (2nd ATPS) and thoroughly mixed. The mixture is vortexed, and then centrifuged such that it is separated into a top phase and a bottom phase. In some embodiments, the top phase is a second target-rich phase containing the target analyte. In some embodiments, the bottom phase is a second target-rich phase containing the target analyte.

In step 124, the second target-rich phase from the step 123 where target DNA partitions to (also referred to as "second target-rich phase") is extracted into an empty microcentrifuge tube. Binding buffer (such as those as described in Examples 2a-5c below) is added into the tube and mixed well with the top phase from the step 123 to form a mixed solution. The mixed solution is transferred to a spin column to form a solid phase extraction complex, which is then centrifuged. Flow-through (also referred as 'supernatant') from the spin column is discarded. The step 124 is repeated until all sample has been passed through the spin column.

In step 125, the solid phase extraction complex is further purified by washing with an appropriate solvent and discarding the supernatant containing impurities. In some embodiments, the appropriate solvent is a binding buffer or a washing buffer. The step 125 is optionally repeated.

In step 126, the solid phase extraction complex is then dried by centrifuging. A suitable elution buffer is added to the solid phase extraction complex, which is then incubated for a certain time to form a final solution. The final solution comprising the purified target DNA is collected to a collection tube by centrifuge for further use.

Example 2a: Comparing DNA Recovery Efficiency from Plasma Using Magnetic Beads with and without Prior Aqueous Two-Phase System (ATPS) Steps In this example, DNA recovery efficiencies from plasma using magnetic beads (also referred as 'magbeads') (i) with prior phase separations using ATPS systems (also referred to as "ATPS steps", "ATPS extraction", or "ATPS workflow") in accordance with methods of the present disclosure; and (ii) without prior ATPS steps are compared.

Materials

In this example, the mixed gender pooled human plasma, citrated (Cat #PR-100), was purchased from TCS Biosciences Ltd. Aqueous two-phase system (ATPS) included polymer-salt based ATPS components (also referred as 'polymer-salt system'). Binding buffer was composed of 1-5M guanidinium, Tris-HCl and EDTA. Unless otherwise noted, 145 bp DNA oligos and/or 2000 bp DNA oligos were used as spike-in's in DNA recovery tests. All other chemicals were of analytical grade.

TaqMan™ Fast Advanced Master Mix (2λ) and custom TaqMan™ Assay used in PCR was supplied by Thermofisher Scientific. The custom TaqMan™ Assay was composed as followings: Forward primer, Reverse primer and a FAM dye-labeled TaqMan MGB probe.

Plasma Cell Lysis

Each 2 mL of human pooled plasma was spiked with 100 fg 145 bp DNA+1.5 uL 2000 bp DNA (TATAA) stock. 160 uL of suitable lysis buffer and 60 uL of Proteinase K (28.5 mg/mL) was added into each 2 mL spiked plasma. The mixture was vortexed thoroughly then lysed for 15 minutes at a pre-heated 60° C. heat block.

Extraction Process

One set of lysed plasma samples (Sample #1) was treated with two sequential ATPS steps (also referred to as "dual ATPS", "two-step ATPS" or "first and second ATPS" in some embodiments) to isolate and concentrate DNA prior to magnetic bead purification, while the other sets of lysed plasma (Sample #2 and #3) did not go through prior ATPS steps and directly proceed into magnetic bead purification.

For Sample #1, ATPS 67 described in Table 1.0 was used as the first ATPS, and ATPS 94 described in Table 1.0 was used as the second ATPS. 2.22 mL of lysed Sample #1 was transferred to 1.170 mL first ATPS and vortex mixed. The mixture was centrifuged at 2,300 rcf for 6 minutes. All salt-rich bottom phase (~1 mL) (also referred to as "target-rich phase" in some embodiments) was transferred into 265 uL second ATPS and thoroughly mixed. The mixture was then centrifuged at 7,000 rcf for 1 minute. Polymer-rich top phase (~150 uL) (also referred to as "second target-rich phase" in some embodiments) was carefully extracted into an empty microcentrifuge tube for further purification.

Purification of DNA 800 uL of binding buffer was added respectively to the extracted top phase of Sample #1 and to the lysed Sample #2 which did not go through ATPS. For Sample #3, 11.43 mL of binding buffer was added to the lysed Sample #3 so that the lysed sample:binding buffer ratio is the same as the top phase:binding buffer ratio in Sample #1. The Samples #1, #2 and #3 are summarized in Table 1.2 below. 12 uL of magnetic bead was added into each tube. The mixture was then incubated on rotator for 5 minutes to prevent sediment of bead. The tube was then briefly spined down and placed on a magnetic rack for 2 minutes to immobilize bead at tube wall. Supernatant was discarded without disturbing the bead. 800 uL of binding buffer was added into each tube and tubes were rotated slowly on magnetic stand for 720° in total. The supernatant was again pipetted and discarded. 800 μL of washing buffer (70% ethanol, 0.001 M EDTA, 0.01 M Tris-HCl) was added to the sample, and the tube was rotated on the rack for 720° in total. The supernatant was discarded. The washing steps were performed twice. To enhance drying effectiveness the tubes were briefly spined down using bench-top microcentrifuge with the hinge facing outwards to collect any remaining washing buffer. The bead was then dried for 7 minutes on magnetic stand with cap opened. The bead complex was resuspended in 40 μL of Elution buffer (0.01 M Tris-HCl, 0.001 M EDTA) by continuous pipette mixing, followed by mild vortex. The tube was then placed on the magnetic rack for 1 minute. The supernatant was collected carefully into a DNA lo-bind tube (purchased from Eppendorf, catalogue #0030108035) without disturbing the magnetic beads for detection.

TABLE 1.2

Summary of test conditions for plasma extraction and purification.

| Sample | Extraction Condition |
|---|---|
| Sample #1 | Dual ATPS (ATPS 67 + ATPS 94, according to Table 1.0), followed by magnetic beads with 800 uL binding buffer |
| Sample #2 | Magnetic beads with 800 uL binding buffer |
| Sample #3 | Magnetic beads with 11430 uL binding buffer | consisted of 50° C. for 2 minutes, followed by 95° C. for 2 minutes and finally 40 cycles of 95° C. for 1 second and 60° C. for 20 seconds. Cycle threshold (CT) was determined, where the fluorescence signal of the amplification reaction was above the background fluorescence using QuantStudio™ Design & Analysis Software. Data analysis on raw CTs was performed in Excel and GraphPad Prism.

All results are presented as average CT values. A lower average CT value indicates a higher amount of the target DNA in the extracted samples, and a higher CT value indicates a lower amount of the target DNA in the extracted samples.

Results

Recovery of DNA

Figure 2A:
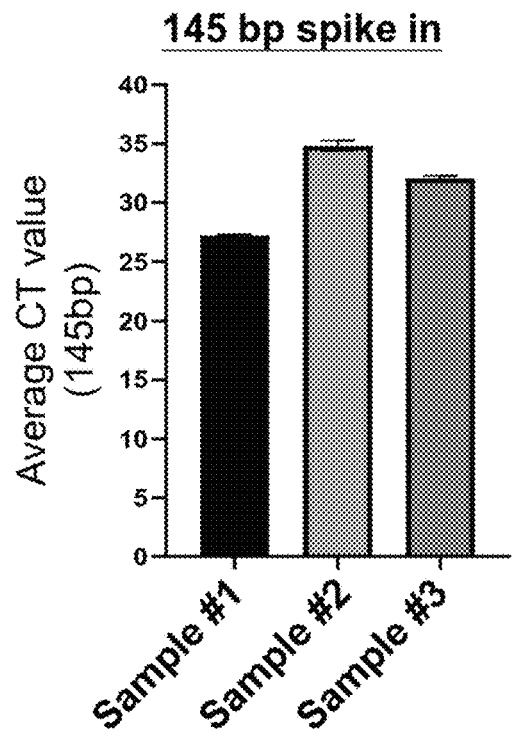
Figure 2B:
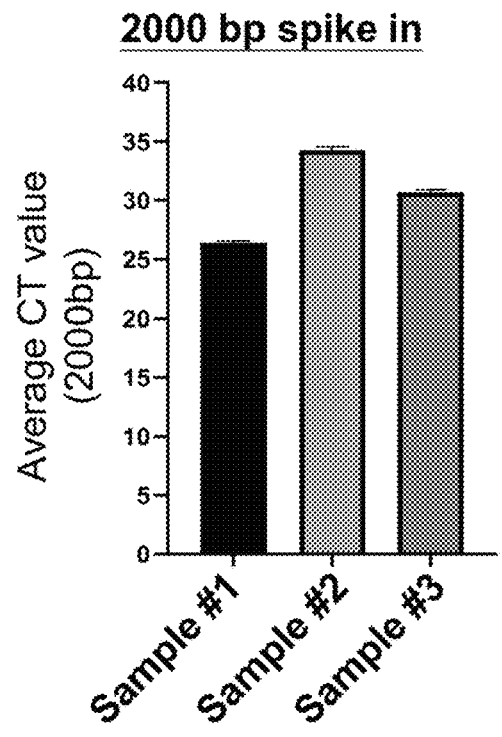

Now referring to FIG. 2A-B, the average CT values of 145 bp and 2000 bp DNA oligos recovered from plasma purified using magnetic beads are shown (Sample #1: with dual ATPS steps, Sample #2: without ATPS steps and non-scaled binding buffer volume, and Sample #3: without ATPS steps and scaled binding buffer volume, according to Table 1.2). The results are summarized in Table 1.3. For 145 bp DNA, plasma Sample #1 had high recovery (average CT value of 27.21), yet poor recovery (average CT value of 34.83) was observed from plasma Sample #2. For Sample #3, the volume of binding buffer was increased proportionally, yet the recovery (average CT value of 32.07) was only slightly improved compared to Sample #2 but still significantly poor compared to the recovery of Sample #1. Similar results were observed for 2000 bp DNA recovery. The results showed the 145 bp and 2000 bp DNA oligos recovery significantly improved when ATPS was incorporated in the extraction process prior to the magnetic bead binding step, and surprisingly, significant improvement in DNA recovery could still be seen compared to the sample without ATPS steps, even where the volume of the binding buffer was increased proportionally.

TABLE 1.3 qPCR results of 145 bp and 2000 bp DNA oligos recovery in plasma with or without two-step ATPS using magnetic beads.

| | 145 bp spike in | | | 2000 bp spike in | | |
|---|---|---|---|---|---|---|
| | | Plasma | | | | |
| | Sample #1 | Sample #2 | Sample #3 | Sample #1 | Sample #2 | Sample #3 |
| CT value | 27.130 | 34.342 | 31.840 | 26.259 | 33.944 | 30.477 |
| | 27.260 | 34.904 | 32.197 | 26.424 | 34.254 | 30.690 |
| | 27.251 | 35.234 | 32.163 | 26.499 | 34.549 | 30.882 |
| Average ± SD | 27.21 ± 0.07 | 34.83 ± 0.45 | 32.07 ± 0.2 | 26.39 ± 0.12 | 34.25 ± 0.3 | 30.68 ± 0.2 |

Detection of DNA

All recovery of DNA oligos discussed in the present disclosure was quantified by quantitative real-time polymerase chain reaction (qPCR) using the Quant Studio 5. qPCR reaction mix (per reaction) consisted of 5 μL of TaqMan Fast Advanced Master Mix (Applied Biosystems, Ref: 4444557), 0.5 μL of 20× custom pre-mixed custom oligo PSI-145 FAM Dental, 0.4 μL of Universal Spike II Primer (TATAA, DS25SII), 0.2 μL Universal Spike II Probe (TATAA, DSSII), 1.9 μL of Ultra-Pure water.

8 μL of the PCR reaction mix was distributed into each PCR well and 2 μL of purified DNA sample was added. qPCR was performed using a QuantStudio™ 3 Real-Time PCR System (Thermofisher Scientific). Thermal cycling Overall, the recovery results have demonstrated that surprisingly, better DNA recovery is achieved when ATPS is incorporated in the plasma extraction workflow prior to magnetic beads purification, even when additional steps of ATPS concentration and isolation are involved, which are potential sources for loss of target analyte during sample handling. By significantly improving the recovery of DNA using ATPS prior to magnetic beads purification, a smaller quantity of magnetic beads is needed to shift binding equilibrium for better yield, thereby reducing the amount of magnetic beads (which are expensive) and hazardous binding buffers that are needed to achieve effective purification.

Example 2b: Plasma Extraction Performance with Varying Polymers and Salts in the ATPS Compositions In this example, the ability to use ATPS with varying polymer molecular weights and component concentrations to integrate with magbeads for DNA recovery from plasma sample, as well as the ability to use ATPS with varying polymer and salt chemical species to integrate with magbeads for DNA recovery from plasma sample, are tested.

Reagents used in this example are similar or the same as those discussed in the preceding examples.

Plasma Cell Lysis

To digest unwanted protein and cells from plasma, 160 µL of a suitable lysis buffer and 60 µL of Proteinase K (28.57 mg/mL) were added into a 2 mL aliquot of citrate (TCS) plasma. 100 fg 145 bp DNA and 100 ng GR 1 kb+ ladder were spiked into the above sample. After vortex for 15 seconds, the sample was incubated at 60° C. for 15 minutes. The lysate was used in further extraction.

Two Phase System

The extraction procedure involves two sequential aqueous two-phase systems (ATPS), including a first ATPS and a second ATPS compositions used to isolate, purify and concentrate DNA from a plasma sample. In the first ATPS, DNA partitions to the bottom phase (also referred to as "target-rich phase") and proteins partition to the top phase (also referred to as "target-poor phase"). The bottom phase, which amount to around 1 mL, was extracted carefully and transferred to the second ATPS. DNA partitions to the top phase (also referred to as "second target-rich phase") of the second ATPS, and the top phase was then extracted carefully for further purification and detection.

In this example, the compositions of the second ATPS have been modified according to the respective first ATPS composition to achieve a small top phase volume of around 150 µL.

Extraction Process

In this example, a method for isolation and purification of cfDNA based on ATPS is introduced. 2.22 mL of lysate was added to the first ATPS. A dye was added to visualize the two phases, which resulted in a colored top phase. In this example, the vast majority of DNA partitioned to the bottom phase, while proteins partitioned to the top phase. The solution was forced to become turbid by vigorous vortex for 15 seconds. Phase separation was then facilitated by centrifuge at 2300 rcf for 6 minutes. After phase separation, the bottom phase had a volume of around 1 mL. The whole bottom phase was extracted carefully and transferred to the second ATPS. The second ATPS mixture was vortexed for 15 seconds to yield a turbid solution and was centrifuged at 7000 rcf for 1 minute to achieve phase separation. The top phase volume in the resulting solution was around 150 µL, which was then extracted carefully for further purification and detection of DNA.

Purification of DNA

The purification of DNA was done by magnetic beads extraction. The top phase from the second ATPS was transferred to a tube containing 800 µL of binding buffer (1-5M guanidinium). 12 µL of MagQu magnetic beads was added to the tube, and the sample was incubated with tilt rotation for 5 minutes. The tube was then briefly spined down and placed on a magnetic stand for 2 minutes to immobilize the beads at the tube wall. The supernatant was pipetted and discarded without disturbing the magnetic beads. To the sample was added 800 µL of binding buffer. The tubes were rotated on the rack for 720° in total. The supernatant was pipetted and discarded. 800 µL of washing buffer (70% ethanol, 0.001 M EDTA, 0.01 M Tris-HCl) was added to the sample, and the tube was rotated on the rack for 720° in total. The supernatant was pipetted and discarded. The washing was performed twice, and the tube was placed on the rack with cap opened to allow the bead to dry. 40 µL of elution buffer (0.01 M Tris-HCl, 0.001 M EDTA) was added to the sample. The beads complex was resuspended by continuous pipette mixing, followed by mild vortex. The sample was incubated at room temperature for 3 minutes and was briefly spined down. The tube was then placed on the magnetic rack for 1 minute. The supernatant was collected carefully without disturbing the magnetic beads for detection.

Extraction Efficiency

Having the second ATPS following the first ATPS, DNA can be further concentrated for detection. Both first and second ATPS comprise a mixture of polymer and salt, in which the resulting top phase is rich in polymer, and bottom phase is rich in salt.

In this example, the extraction efficiency of DNA in different ATPS compositions have been studied, while keeping the volume ratios of the target-rich phase and target-poor phase in the first and the second ATPS constant. To evaluate the DNA recovery performance, the samples were prepared containing 100 ng of DNA ladder in 2 mL human plasma, amounting to 2.5 ng per µL of eluant assuming 100% recovery.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Figure 2C:
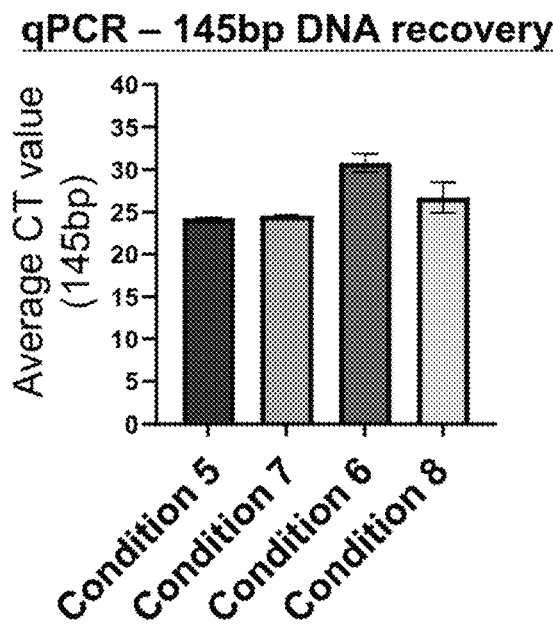
FIG. 2C is a graph showing the average CT values of 145 bp DNA recovered from plasma using the ATPS conditions according to Table 1.4 in Example 2b.

Now referring to FIG. 2C, the average CT values of 145 bp DNA recovery using the first and second ATPS compositions according to Conditions 5, 7, 6, and 8 in Table 1.4 are compared. Conditions 5, 7, 6, and 8 correspond to the same polymer and salt combination with different polymer molecular weights, and their respective 145 bp DNA recovery results are reported in Table 1.4. The results demonstrate that all systems with various polymer molecular weights in the first ATPS recover detectable levels of DNA from plasma when combined with the magnetic beads workflow.

TABLE 1.4

DNA recovery from plasma using ATPS with different polymers molecular weights and magnetic beads.

| Condition | First ATPS* | Second ATPS* | Average CT value (145 bp) ± SD |
|---|---|---|---|
| 5 | ATPS 69 | ATPS 95 | 24.28 ± 0.07 |
| 7 | ATPS 19 | ATPS 81 | 24.56 ± 0.08 |
| 6 | ATPS 107 | ATPS 72 | 30.81 ± 1.09 |
| 8 | ATPS 114 | ATPS 91 | 26.70 ± 1.8 |

*ATPS compositions according to Table 1.0

Figure 2D:
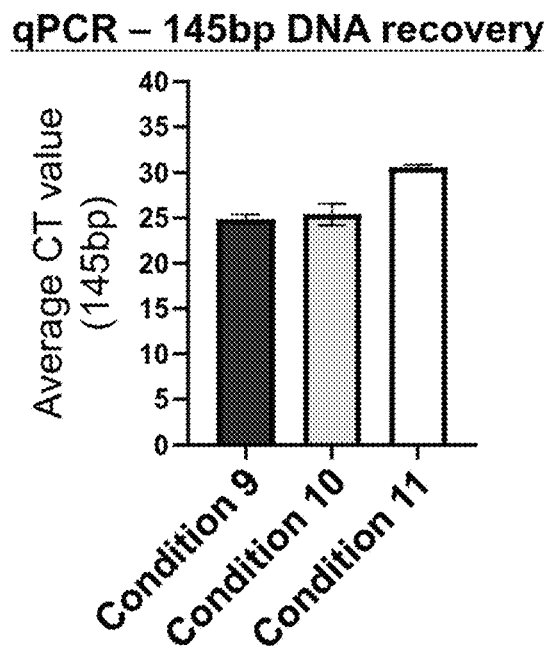
FIG. 2D is a graph showing the average CT values of 145 bp DNA recovered from plasma using the ATPS conditions according to Table 1.5 in Example 2b.

Now referring to FIG. 2D, the average CT values of 145 bp DNA recovery using the first and second ATPS compositions according to Conditions 9, 10 and 11 in Table 1.5, are compared. Conditions 9, 10, 11 correspond to three different polymer and salt combinations, and their respective 145 bp DNA recovery results are reported in Table 1.5. The results demonstrate that all systems with various polymer and salt combinations in the first or second ATPS recover satisfactory levels (e.g., sufficient for downstream uses, such as for detection purposes in diagnostic applications) of DNA.

TABLE 1.5

DNA recovery from plasma using ATPS with different polymers and salt combinations and magnetic beads.

| Condition | First ATPS* | Second ATPS* | Average CT value (145 bp) ± SD |
|---|---|---|---|
| 9 | ATPS 102 | ATPS 96 | 24.88 ± 0.54 |
| 10 | ATPS 76 | ATPS 74 | 25.41 ± 1.18 |
| 11 | ATPS 109 | ATPS 83 | 30.61 ± 0.28 |

*ATPS compositions according to Table 1.0

In summary, for systems with the same polymer and salt types but different polymer sizes (Conditions 5, 7, 6 and 8, Table 1.4), satisfactory amounts of DNA were recovered over a variety of polymer sizes in the first ATPS. For systems using different salts (such as various cations and anions) and polymers of different properties (Conditions 9, 10 and 11, Table 1.5), recovery of DNA was also satisfactory.

Example 2c: Plasma Extraction Performance with Varying ATPS Systems with Magnetic Beads In this example, the performance of extracting DNA from plasma using different classes of ATPS systems (polymer-salt, polymer-polymer, micellar) in combination with magnetic beads is demonstrated. The materials used in this example are the same of similar as those discussed in the preceding examples. For the sake of brevity and simplicity of the present disclosure, the discussion of the materials is not reproduced here.

Plasma Lysis

In this example, K2 EDTA plasma (TCS Biosciences, Lot #23014500) were lysed according to methods that are optimized for their respective downstream ATPS systems. Samples were spiked with 100 fg 145 bp DNA and 1.5 uL stock 2000 bp DNA.

For the polymer-polymer based ATPS system, 500 uL of suitable lysis buffer and 30 uL Proteinase K (28.57 mg/mL) were added to 1 mL of K2 EDTA plasma, vortexed thoroughly and incubated in a pre-heated 60° C. water bath for 15 minutes.

For the micellar based ATPS system, 300 uL of suitable lysis buffer was added to 1 mL K2 EDTA plasma, vortexed thoroughly and incubated at room temperature for 3 minutes. Then 112.5 uL of protein precipitation buffer A (PPt A) (20% ZnCl w/v, 1% acetic acid w/v) was added, vortexed thoroughly until homogenous and centrifuged at 12000 rcf for 3 minutes. Other suitable protein precipitation buffers can be used in the method above instead of protein precipitation buffer A. The supernatant is extracted for further downstream processing while the pellet is discarded.

For the polymer-salt based ATPS system, 80 uL of suitable lysis buffer and 30 uL Proteinase K (28.57 mg/mL) were added to 1 mL K2 EDTA plasma, vortexed thoroughly and incubated in a pre-heated 60° C. water bath for 15 minutes.

Extraction Process

Different varieties of aqueous two-phase systems (ATPS) were prepared to efficiently extract cfDNA from plasma samples. The 3 different varieties of ATPS and the subsequent binding steps are summarized in Table 1.6.

TABLE 1.6

Summary of experimental conditions with alternate ATPS classes.

| ATPS Class | ATPS Composition(s) | Binding Step | Second Binding Step |
|---|---|---|---|
| 1. Polymer-polymer (P-P) | ATPS 1 | 1500 uL binding buffer added to the extracted polymer rich bottom phase | 800 uL binding buffer added to the magnetic beads |
| 2. Micellar | ATPS 50 | 500 uL binding buffer added to the extracted surfactant rich top phase | — |
| 3. Polymer-salt (P-S) | First ATPS: ATPS 63 | — | — |
| | Second ATPS: ATPS 65 | 800 uL binding buffer added to the extracted polymer rich top phase of the second polymer-salt ATPS system | 800 uL binding buffer added to the magnetic beads |

Sample lysates were added to their respective ATPS systems: 1530 uL sample lysate into 500 uL of the polymer-polymer based system, and 1110 uL sample lysate into 1.17 mL the first polymer-salt based system. For the micellar system, 1200 uL of the extracted supernatant after protein precipitation was added into 500 mg of the micellar system. In some embodiments, the first ATPS system is a single ATPS system, which is not followed by a second ATPS.

All ATPS tubes were vortexed thoroughly post sample lysate addition and vortexed thoroughly.

The polymer-polymer ATPS system was centrifuged at 2300 rcf for 6 minutes. The target cfDNA partitioned strongly to the bottom polymer rich phase. All the bottom phase (~300 uL) was extracted and transferred to a new 2 mL centrifuge tube for further processing.

The micellar ATPS system was centrifuged at 12000 rcf for 5 minutes. The target cfDNA partitioned strongly to the surfactant rich top phase. All the top phase (~280 uL) was extracted and transferred to a new 2 mL centrifuge tube for further processing.

For the polymer-salt ATPS system, the extraction process is the same or similar to the method discussed in the preceding examples. The first polymer-salt ATPS system was centrifuged at 2300 rcf for 6 minutes. The target cfDNA partitioned strongly to the bottom salt rich phase. All the bottom phase (~1000 uL) was extracted and transferred to the second ATPS tube containing 265 uL second ATPS composition, where it was vortexed thoroughly before being centrifuged at 7000 rcf for 1 minute. The target cfDNA partitioned and was concentrated into a polymer-rich top phase of around 120 uL. It was then extracted and transferred to a new tube for further processing.

Purification of DNA

After extraction of the phases containing target cfDNA from their respective ATPS systems, downstream processing included addition of a solid phase medium and binding buffer for nucleic acid isolation from liquid medium, followed by washing of unwanted ions and molecules before the target nucleic acid was eluted by an elution buffer.

1500 uL of binding buffer (3-7M guanidinium, 50 mM pH 7 $Na_2HPO_4/NaH_2PO_4$) was added to the extracted polymer-rich bottom phase of the polymer-polymer system. 500 uL of binding buffer (3-7M guanidinium) was added to the extracted surfactant rich top phase of the micellar system. 800 uL of binding buffer (3-7M guanidinium) was added to the extracted polymer rich top phase of the second polymer-salt ATPS system. 6 uL of magnetic beads (MagQu) were then added to all centrifuge tubes containing the mixture of extracted phase and binding buffer, and put onto a rotator to incubate for 5 minutes. The target cfDNA was bound to the magnetic beads during the incubation. After incubation, all tubes were briefly centrifuged before placing on magnetic racks, where the applied magnetic field attracted the cfDNA bound magnetic bead. The supernatant was then taken and discarded, leaving the magnetic beads bound to the inner wall of the centrifuge tube. A second binding buffer wash step was performed for the polymer-polymer and polymer-salt systems. 800 uL of binding buffer (3-7M guanidinium, 50 mM pH 7 $Na_2HPO_4/NaH_2PO_4$) was added to the magnetic beads from the polymer-polymer system, and 800 uL of binding buffer (3-7M guanidinium) was added to the magnetic beads from the polymer-salt system. The centrifuge tubes were then vortexed thoroughly and briefly spun down before being placed back on the magnetic racks. The supernatant was discarded once all the magnetic beads were bound to the inner side of the centrifuge wall.

800 uL of original washing buffer (70% v/v EtOH, 1 mM EDTA, 10 mM Tris-HCl) was added to magnetic beads from the polymer-polymer and polymer-salt system, while 500 uL of RPE washing buffer (80% v/v EtOH, 0.1M NaCl, 10 mM Tris-HCl) was added to magnetic beads from the micellar system. The centrifuge tubes were turned 720° on the magnetic racks before washing buffer was discarded. The procedure was repeated for a second wash. The centrifuge tubes were then briefly centrifuged before being placed back on the magnetic rack, any excess washing buffer remaining in the centrifuge tube was then discarded. The magnetic beads were allowed to dry at room temperature for 7 minutes for polymer-polymer and polymer-salt systems, and 10 minutes for the micellar systems.

Figure 2E:
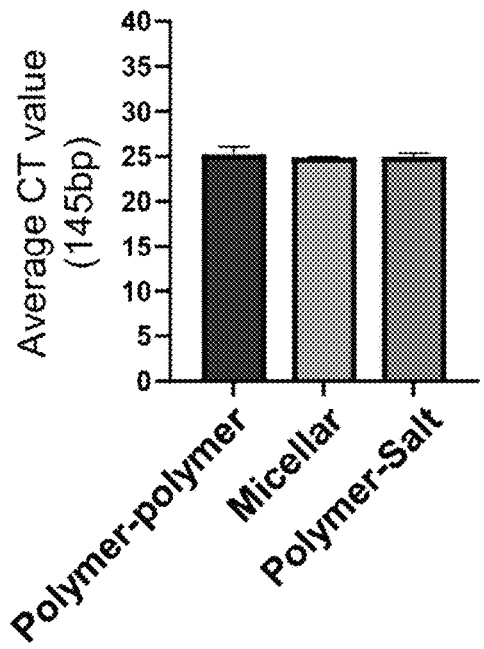
FIG. 2E is a graph showing the average CT values of 145 bp DNA recovered from plasma using 3 different types of ATPS and magnetic beads, according to Example 2c.
Figure 2F:
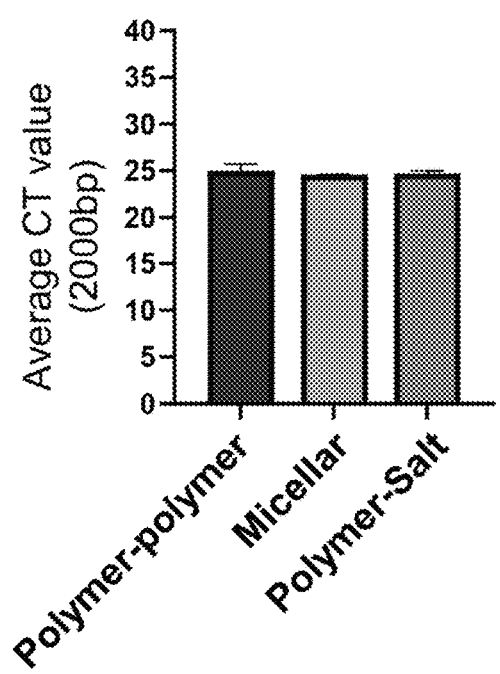
FIG. 2F is a graph showing the average CT values of 2000 bp DNA recovered from plasma using 3 different types of ATPS and magnetic beads, according to Example 2c.

After the magnetic beads were allowed to dry, 20 uL of elution buffer (10 mM Tris-HCl, 1 mM EDTA) were used to resuspend the magnetic beads, then left to incubate at room temperature for 3 minutes. The target cfDNA was eluted from the magnetic beads into the elution buffer. The tubes were then placed back onto the magnetic racks and the elution buffer was extracted once the magnetic beads were all bound.
Detection of DNA The steps to perform the detection of DNA for each sample are the same or similar to those as discussed with respect to Example 2a above. For the sake of brevity and simplicity of the present disclosure, the discussion of the detection steps is not reproduced here. The results were presented as average CT values.
Results
Partitioning The first ATPS from the polymer-polymer (P-P) and polymer-salt based (P-S) category were efficient at partitioning the target cell-free DNA (cfDNA) from the lysed sample into the bottom phase of the first ATPS, while unwanted excess protein partitioned to the top phase of the ATPS system. The opposite trend appeared in the micellar ATPS system where cfDNA partitioned to the top phase. The P-S second ATPS was used to concentrate the large bottom phase of the first ATPS into a more concentrated smaller top phase volume for more user-friendly downstream processing.
Recovery of DNA Now referring to FIGS. 2E-2F, the average CT values of 145 bp DNA and 2000 bp DNA recovered from plasma using the three different types of ATPS system, namely, the polymer-polymer system, the micellar system and the polymer-salt system, are shown. For 145 bp DNA recovery, the efficiency of these three systems are comparable as the difference in average CT values among the polymer-polymer system (average CT value=24.81), micellar system (average CT value=24.93) and polymer-salt system (average CT value=24.73) are all within 1 CT value (see Table 1.7). Similar results are observed in the recovery of 2000 bp DNA. The results demonstrate that recovery of 145 bp and 2000 bp DNA are comparable between various ATPS classes.

TABLE 1.7 qPCR results of 145 bp and 2000 bp DNA oligos recovery in plasma with different ATPS classes using magnetic beads.

|  | 145 bp DNA recovery | | | 2000 bp DNA recovery | | |
| --- | --- | --- | --- | --- | --- | --- |
|  | Polymer-polymer | Micellar | Polymer-salt | Polymer-polymer | Micellar | Polymer-salt |
| CT value | 24.637 | 24.892 | 24.743 | 24.386 | 24.564 | 24.440 |
|  | 24.973 | 24.967 | 25.452 | 24.812 | 24.589 | 25.027 |
|  | 26.185 | 24.938 | 24.720 | 25.775 | 24.582 | 24.562 |
| Average ± SD | 24.81 ± 0.24 | 24.93 ± 0.04 | 24.73 ± 0.02 | 24.6 ± 0.3 | 24.58 ± 0.01 | 24.5 ± 0.09 |

Example 3a: Comparing DNA Recovery Efficiency from Plasma Using Spin Column with and without Prior Aqueous Two-Phase System (ATPS) Steps In this example, DNA recovery efficiencies from plasma using spin column (i) with prior phase separations using ATPS systems in accordance with the method of the present disclosure; and (ii) without prior ATPS steps are compared. The materials used in this example are the same of similar as those discussed in the preceding examples. For the sake of brevity and simplicity of the present disclosure, the discussion of the materials is not reproduced here.
Materials The materials used in this example are the same or similar to the materials as discussed with respect to the preceding examples except spin column (EconoSpin) was used in the purification of DNA instead of magnetic beads. For the sake of brevity and simplicity of the present disclosure, the discussion of the materials is not reproduced here.

EconoSpin DNA/RNA minispin columns were purchased from Epoch Life Sciences. Universal DNA spike II template was purchased from TATAA Biocenter, GeneRuler 1 kb+ DNA ladder was purchased from ThermoFisher.
Plasma Cell Lysis Each 2 mL of human pooled plasma was spiked with 100 fg of 145 bp double stranded DNA (dsDNA) oligos, 1.5 uL of stock 2000 bp dsDNA oligo and 100 ng of 1 kb+ ladder.

160 uL of a suitable lysis buffer and 60 uL of Proteinase K (28.5 mg/mL) was added into each 2 mL spiked plasma. The mixture was vortexed thoroughly then lysed for 15 minutes at a pre-heated 60° C. heat block.

Extraction Process

One set of lysed plasma samples (Sample #4) was treated with two sequential ATPS to isolate and concentrate DNA prior to spin column purification, while the other sets of lysed plasma (Sample #5 and Sample #6) did not go through prior ATPS steps and directly proceed into spin column purification.

The steps to prepare Samples #4-6 in this example are the same or similar to the materials as discussed with respect to Example 2a. For the sake of brevity and simplicity of the present disclosure, the discussion of the two-phase system steps is not reproduced here.

Purification of DNA

In this example, binding buffer containing 1-5M Guanidinium was used.

800 uL of binding buffer was added respectively to the extracted top phase of Sample #4 and lysed Sample #5 which did not go through prior ATPS. For Sample #6, 11.43 mL of binding buffer was added to the lysed Sample #6 so that the lysed sample:binding buffer ratio is the same as the top phase:binding buffer ratio in Sample #4. The samples #4-6 are summarized in Table 2.0 below. All samples were vortexed thoroughly before being applied to EconoSpin columns and centrifuged at 12,000 rcf for 30 seconds, in 800 uL until all sample lysate had passed through the column. The flow-through (also referred as 'supernatant') was then discarded. 800 uL of washing buffer (70% ethanol, 0.001 M EDTA, 0.01 M Tris-HCl) was added to the spin column and centrifuged at 12,000 rcf for 30 seconds. The flow through was discarded and the spin columns were centrifuged at 16,000 rcf for 2 minutes to remove excess wash buffer. 40 uL of elution buffer (0.01 M Tris-HCl, 0.001 M EDTA) was added to the spin column and allowed to incubate for 3 minutes. The spin column was centrifuged at 12,000 rcf for 1 minute to elute the buffer containing target DNA into a DNase free centrifuge tube.

TABLE 2.0

Summary of test conditions for plasma extraction and purification.

| Sample | Condition |
|---|---|
| Sample #4 | Dual ATPS (ATPS 67 + ATPS 94, according to Table 1.0), followed by EconoSpin columns with 800 uL binding buffer |
| Sample #5 | EconoSpin columns with 800 uL binding buffer |
| Sample #6 | EconoSpin columns with 11430 uL binding buffer |

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Recovery of DNA

Figure 3A:
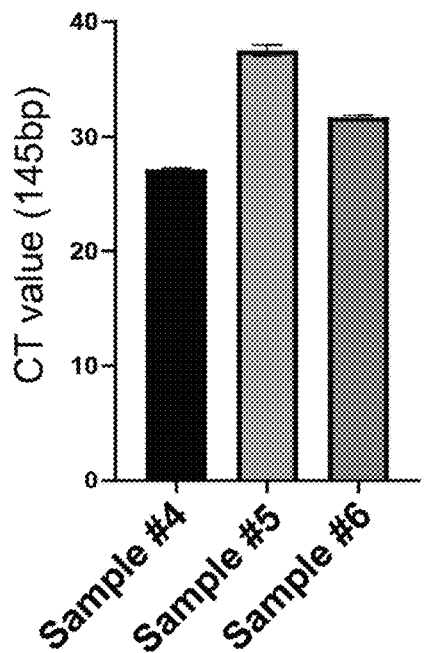
Figure 3B:
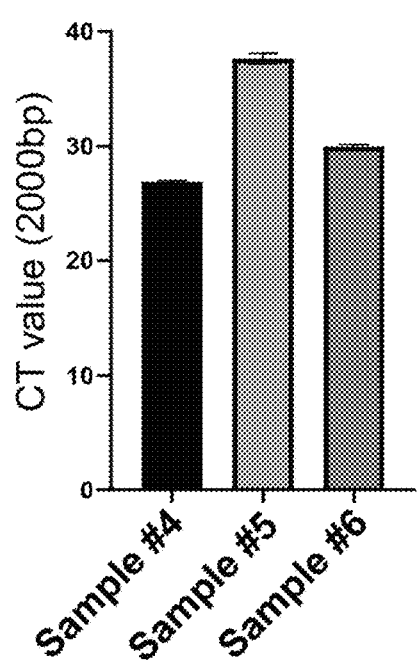

Now referring to FIGS. 3A-3B, the average CT values of 145 bp and 2000 bp DNA oligos recovered from plasma purified using spin columns are shown (Sample #4: with ATPS step, Sample #5: without ATPS step and non-scaled binding buffer volume, and Sample #6: without ATPS steps and scaled binding buffer volume, according to Table 2.0). For 145 bp DNA, plasma Sample #4 had high recovery (average CT value of 27.15), yet poor recovery (average CT value of 37.49) is observed from plasma Sample #5. For Sample #6, the volume of binding buffer was increased proportionally, and the recovery (average CT value of 31.71) was improved compared to Sample #5 but still significantly poor compared to the recovery of Sample #4. Similar results can be observed for 2000 bp DNA recovery. The data showed that by using the two-step ATPS steps to concentrate and purify plasma sample prior to binding to column binding step, DNA recovery is improved, and surprisingly, significant improvement in DNA recovery can still be seen compared to the sample without ATPS steps even where the volume of the binding buffer was increased proportionally.

TABLE 2.1 qPCR results of 145 bp and 2000 bp DNA oligos recovery in plasma with or without two-step ATPS using spin column.

| | 145 bp spike in Plasma | | | 2000 bp spike in Plasma | | |
|---|---|---|---|---|---|---|
| | Sample #4 | Sample #5 | Sample #6 | Sample #4 | Sample #5 | Sample #6 |
| CT value | 27.238 | 36.945 | 31.868 | 27.031 | 37.115 | 30.205 |
| | 27.052 | 37.819 | 31.552 | 26.837 | 37.793 | 29.802 |
| | 27.166 | 37.717 | 31.704 | 26.884 | 37.99 | 29.870 |
| Average ± SD | 27.15 ± 0.09 | 37.49 ± 0.48 | 31.71 ± 0.16 | 26.92 ± 0.1 | 37.63 ± 0.46 | 29.96 ± 0.22 |

Overall, the recovery results have demonstrated that surprisingly, better DNA recovery is achieved when ATPS is incorporated in the plasma extraction workflow prior to purification using spin columns, even when additional steps of ATPS concentration and isolation are involved, which are potential sources for loss of target analyte during sample handling.

Example 3b: Plasma Extraction Performance with Varying Polymers and Salts in the ATPS Compositions In this example, the ability to use ATPS with varying polymer molecular weights and component concentrations to integrate with spin column for DNA recovery from plasma sample, as well as the ability to use ATPS with varying polymer and salt chemical species to integrate with spin column for DNA recovery from plasma sample, are demonstrated. The materials used in this example are the same of similar as those discussed in the preceding examples. For the sake of brevity and simplicity of the present disclosure, the discussion of the materials is not reproduced here.

Plasma Cell Lysis

In this example, 160 µL of a suitable lysis buffer and 60 µL of Proteinase K (28.57 mg/mL) were added into a 2 mL aliquot of EDTA (K2 TCS) plasma. 100 fg 145 bp DNA and 100 ng GR 1 kb+ ladder were spiked into the above sample. After vortex for 15 seconds, the sample was incubated at 60° C. for 15 minutes. The lysate was used in further extraction.

Two Phase System

The extraction procedure involves two sequential aqueous two-phase systems (ATPS) to isolate, purify and concentrate DNA from a plasma sample. The steps to perform ATPS extraction in this example are the same or similar to those as discussed with respect to Example 2b.

Extraction Process

In this example, a method for isolation and purification of cfDNA based on ATPS is introduced. To the first ATPS was added 2.22 mL of lysate. A dye was added to visualize the two phases, which resulted in a colored top phase. In this example, the vast majority of DNA partitioned to the bottom phase, while proteins were partitioned to the top phase. The solution was forced to become turbid by vigorous vortex for 15 seconds. Phase separation was then facilitated by centrifuge at 2300 rcf for 6 minutes. After phase separation, the bottom phase had a volume of around 1 mL. The whole bottom phase was extracted carefully and transferred to the second ATPS. The second ATPS mixture was vortexed for 15 seconds to yield a turbid solution and was centrifuged at 7000 rcf for 1 minute to achieve phase separation. The top phase volume in the resulting solution was around 150 µL, which was then extracted carefully for further purification and detection of DNA.

Purification of DNA

The purification of DNA was done by spin column extraction. The top phase from the second ATPS was transferred to a tube containing 800 µL of binding buffer (1-5M guanidinium). Mixed thoroughly, 800 µL of the solution was transferred to a spin column (EconoSpin) and was centrifuged for 30 seconds at 12,000 rcf. The flow-through was discarded. The process was repeated until all sample had been passed through the spin column. To the spin column was added 800 µL of washing buffer (70% ethanol, 0.001 M EDTA, 0.01 M Tris-HCl), and was centrifuged for 30 seconds at 12,000 rcf. The washing was performed twice, and the tube was centrifuged for 2 minutes at 16,000 rcf to dry. 40 µL of elution buffer (0.01 M Tris-HCl, 0.001 M EDTA) was added to the sample. The sample was incubated at room temperature for 3 minutes. The elution was collected to a collection tube by centrifuge for 1 minute at 12,000 rcf for detection.

Extraction Efficiency

The extraction efficiency of DNA in different ATPS compositions have been studied, while keeping the volume ratios in the first and the second ATPS constant. To evaluate the DNA recovery performance, the samples were prepared containing 100 ng of DNA ladder in 2 mL human plasma, amounting to 2.5 ng per µL of eluant assuming 100% recovery.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Figure 3C:
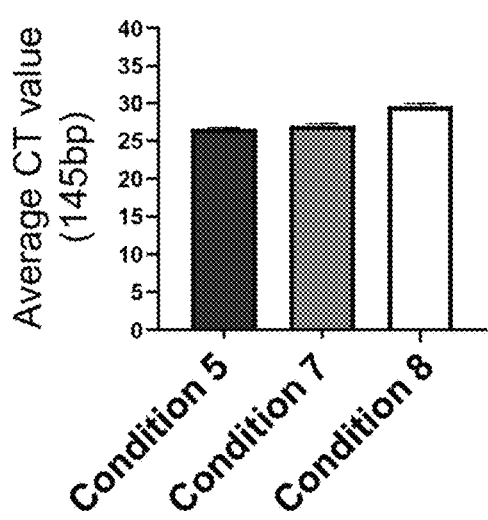
FIG. 3C is a graph showing the average CT values of 145 bp DNA recovered from plasma using the ATPS conditions according to Table 2.3 in Example 3b.

Now referring to FIG. 3C, the average CT values of 145 bp DNA recovery from plasma using the first and second ATPS compositions according to Conditions 5, 7 and 8 in Table 2.3, are compared. Conditions 5, 7 and 8 correspond to the same polymer and salt combination with different polymer molecular weights, and their respective 145 bp DNA recovery results are reported in Table 2.3. The results demonstrate that all systems with alternate polymer molecular weights recover detectable levels of DNA when combined with the spin column workflow.

TABLE 2.3

DNA recovery from plasma using ATPS with different polymers molecular weights and spin column.

| Condition | First ATPS* | Second ATPS* | Average CT value (145 bp) ± SD |
| --- | --- | --- | --- |
| 5 | ATPS 69 | ATPS 95 | 26.59 ± 0.15 |
| 7 | ATPS 19 | ATPS 81 | 27.02 ± 0.26 |
| 8 | ATPS 114 | ATPS 91 | 29.58 ± 0.35 |

*ATPS compositions according to Table 1.0

Figure 3D:
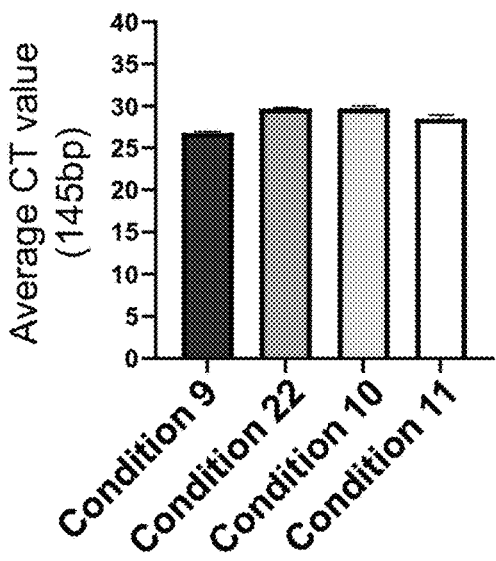
FIG. 3D is a graph showing the average CT values of 145 bp DNA recovered from plasma using the ATPS conditions according to Table 2.4 in Example 3b.

Now referring to FIG. 3D, the average CT values of 145 bp DNA recovery from plasma using the first ATPS and second ATPS compositions according to Conditions 9, 22, 10 and 11 in Table 2.4 are compared. Conditions 9, 10, 11 correspond to three different polymer and salt combinations, and their respective 145 bp DNA recovery results are reported in Table 2.4. The results demonstrate that all systems with alternate polymer and salt recover detectable DNA when combined with the spin column workflow.

TABLE 2.4

DNA recovery from plasma using ATPS with varying range of polymer and salts and spin column.

| Condition | First ATPS* | Second ATPS* | Average CT value (145 bp) ± SD |
| --- | --- | --- | --- |
| 9 | ATPS 102 | ATPS 96 | 26.74 ± 0.17 |
| 22 | ATPS 115 | ATPS 84 | 29.71 ± 0.09 |
| 10 | ATPS 76 | ATPS 74 | 29.74 ± 0.28 |
| 11 | ATPS 109 | ATPS 83 | 28.47 ± 0.48 |

*ATPS compositions according to Table 1.0

Example 3c: Plasma Extraction Performance with Varying ATPS Systems Using Spin Column In this example, the performance of different classes of ATPS systems (polymer-salt, polymer-polymer, micellar) being used with spin column is demonstrated. The materials used in this example are the same of similar as those discussed in the preceding examples. For the sake of brevity and simplicity of the present disclosure, the discussion of the materials is not reproduced here.

Plasma Lysis

In this example, K2 EDTA plasma (TCS Biosciences, Lot #23014500) were lysed in 3 separate ways to that are optimized for their respective downstream ATPS systems. The lysed samples used in this example are the same or similar to those as discussed with respect to Example 2c. For the sake of brevity and simplicity of the present disclosure, the discussion of the lysed samples is not reproduced here.

Extraction Process

The extraction process and the 3 different classes of ATPS systems prepared were the same as those as discussed in Example 2c and Table 1.6:1. Polymer-polymer based (P-P); 2. Micellar; and 3. Dual ATPS-Polymer-salt based (P-S). For the sake of brevity and simplicity of the present disclosure, the discussion of the preparation of the above ATPS composition and the extraction process is not reproduced here. The 3 different varieties of ATPS and the subsequent binding steps are summarized in Table 2.5.

TABLE 2.5

Summary of experimental conditions with alternate ATPS classes.

| ATPS Class | ATPS Composition | Binding Step |
|---|---|---|
| 1. Polymer-polymer (P-P) | ATPS 1 | 1500 uL binding buffer added to the extracted polymer-rich bottom phase |
| 2. Micellar | ATPS 50 | 500 uL binding buffer added to the extracted surfactant rich top phase |
| 3. Polymer-salt (P-S) | First ATPS: ATPS 63 | — |
| | Second ATPS: ATPS 65 | 800 uL binding buffer added to the extracted polymer rich top phase of the second polymer-salt ATPS system |

Purification of DNA

After extraction of phases containing target cfDNA from their respective ATPS systems, downstream processing includes addition of a binding buffer to spin columns containing porous membranes for nucleic acid isolation from liquid medium, followed by washing of unwanted ions and molecules before the target nucleic acid is eluted by an elution buffer. The respective binding buffer used for each sample is summarized in Table 2.5.

1500 uL of binding buffer (3-7M guanidine, 50 mM pH 7 $Na_2HPO_4/NaH_2PO_4$) is added extracted polymer-rich bottom phase of the polymer-polymer system. 500 uL of binding buffer (3-7M guanidine) is added to the extracted surfactant rich top phase of the micellar system. 800 uL of binding buffer (1-5M guanidine) is added to the extracted polymer rich top phase of the second polymer-salt ATPS system. 800 uL of each sample is then added to individual EconoSpin column for DNA and is centrifuged for 30 seconds at 12,000 rcf. The target cfDNA will bind to the spin column and be retained while the sample lysate flow through is discarded by the vacuum manifold. The flow-through was discarded and the process was repeated until all sample has flowed through the spin column. 800 uL of washing buffer (70% EtOH v/v, 1 mM EDTA, 10 mM Tris-HCl) was added to spin columns of the polymer-polymer and polymer-salt systems, while 400 uL of RPE washing buffer (80% EtOH, 100 mM NaCl, 10 mM Tris-HCl) was added to the spin column of the micellar system. All spin columns are then centrifuged at 12000 rcf for 30 seconds. This washing step removes impurities like protein and other ions that are bound to the silica spin column membrane. The flow through is discarded and the spin column is further centrifuged at 16000 rcf for 2 minutes to remove any excess RPE wash buffer. The spin columns were then placed in new 1.5 mL centrifuge tubes where 80 uL of elution buffer (0.01M Tris-HCl, 1 mM EDTA) were pipetted directly onto the silica membrane and allowed to incubate at room temperature for 3 minutes. The spin columns were centrifuged at 12000 rcf for 1 minute to elute the target cfDNA into 1.5 mL centrifuge tube.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Recovery of DNA

Figure 3E:
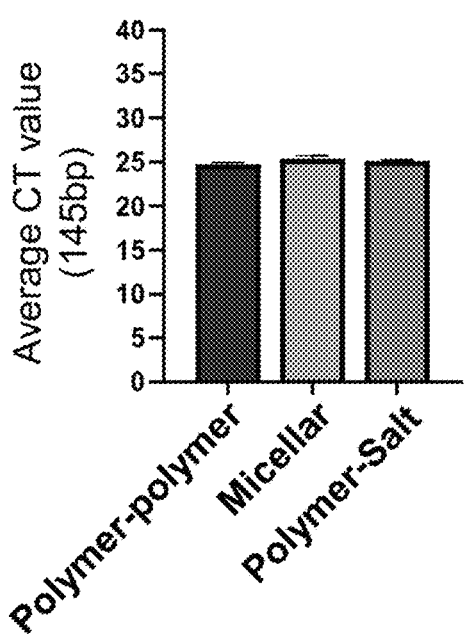
FIG. 3E is a graph showing the average CT values of 145 bp DNA recovered from plasma using 3 different types of ATPS and spin column, according to Example 3c.
Figure 3F:
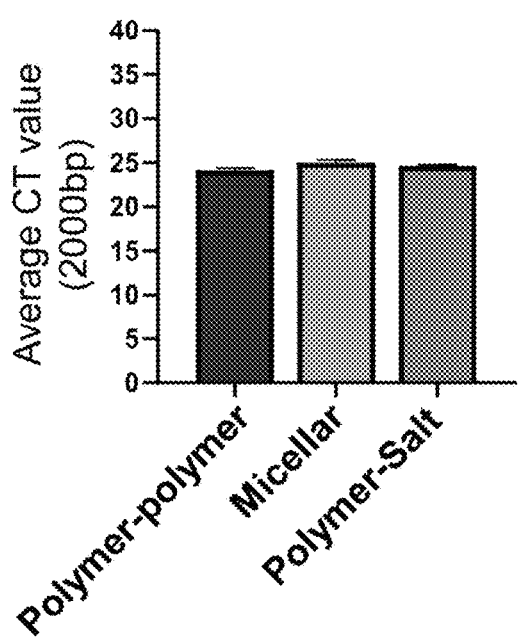
FIG. 3F is a graph showing the average CT values of 2000 bp DNA recovered from plasma using 3 different types of ATPS and spin column, according to Example 3c.

Now referring to FIGS. 3E-3F, the average CT values of 145 bp DNA and 2000 bp DNA recovered from plasma are all comparable between the 3 different types of ATPS system, with acceptable recovery that are all within ~1 CT value difference as shown in Table 2.6. This demonstrates that a different variety of ATPS classes can recover DNA in a similar degree when optimized.

TABLE 2.6 qPCR results of 145 bp and 2000 bp DNA oligos recovery in plasma with different ATPS classes using spin column.

| | 145 bp DNA recovery | | | 2000 bp DNA recovery | | |
|---|---|---|---|---|---|---|
| | Polymer-polymer | Micellar | Polymer-salt | Polymer-polymer | Micellar | Polymer-salt |
| CT value | 24.488 | 25.766 | 25.057 | 23.919 | 25.371 | 24.608 |
| | 24.751 | 25.017 | 25.223 | 24.148 | 24.774 | 24.789 |
| | 24.940 | 25.236 | 25.026 | 24.365 | 24.875 | 24.602 |
| Average ± SD | 24.73 ± 0.23 | 25.13 ± 0.15 | 25.1 ± 0.11 | 24.14 ± 0.22 | 24.82 ± 0.07 | 24.67 ± 0.11 |

Example 4a: Comparing DNA Recovery Efficiency from Urine Using Magnetic Beads with and without Prior Aqueous Two-Phase System (ATPS) Steps In this example, DNA recovery efficiencies from urine using magnetic beads (i) with prior phase separation using ATPS systems (also referred to as "ATPS steps", "ATPS extraction", or "ATPS workflow") in accordance with the method of the present disclosure; and (ii) without prior ATPS steps are compared. The materials used in this example are the same of similar as those discussed in the preceding examples. For the sake of brevity and simplicity of the present disclosure, the discussion of the materials is not reproduced here.

Urine Lysis

Urine samples were collected from 3 different donors. The samples from each donor were aliquoted into tubes of 40 mL per tube and divided into 2 sets, with each set containing 1 sample from each donor.

All 2 sets of urine samples were pre-treated with 200 uL of 0.1M EDTA per 10 mL urine sample, vortexed thoroughly and centrifuged at 3000 rcf for 10 minutes. The supernatant was transferred to a new tube while the pellet was discarded.

Unwanted protein and cells present in pre-treated urine samples are lysed by adding 1200 μL of (28.57 mg/mL) Proteinase K and 4 mL of a suitable lysis buffer to 40 mL of sample per donor. The samples were then vortexed thoroughly till homogenous then left in a pre-heated 37° C. water bath to incubate for 15 minutes.

Extraction Process

Two different aqueous two-phase systems (ATPS) were prepared to efficiently extract cfDNA from urine samples. The first ATPS is used for initial extraction of urine sample where the intended cfDNA partitions strongly to the bottom salt-rich phase. The bottom phase from the first ATPS is then extracted and added to the second ATPS, which is used to concentrate the target cfDNA into a small volume (400 uL-600 uL) to allow for user-friendly downstream processing.

In this example, the first ATPS consists of the composition of ATPS 38, according to Table 1.0, with 22600 uL of a lysed urine sample.

The second ATPS consists of the composition of ATPS 71, according to Table 1.0, with 3.5 mL-5 mL of first ATPS bottom phase.

For urine sample set 1 (Sample #1), urine samples from each donor were split in half then added to the 2 first ATPS tubes. The first ATPS were vortexed thoroughly then centrifuged at 2300 rcf for 6 minutes. The salt-rich bottom phase from two first ATPS (same donor) were then extracted, recombined, and added to one tube of second ATPS, which was vortexed thoroughly and centrifuged to allow to phase separate. The polymer rich top phase of the second ATPS system was extracted and put into a new tube.

Urine sample set 2 (Sample #2) was pre-treated and processed but did not go through the dual ATPS system for concentration and purification. The urine sample sets are summarized in Table 3.0 below.

TABLE 3.0

Summary of test conditions for urine extraction and purification.

| Sample | Condition |
|---|---|
| Sample #1 | Dual ATPS (ATPS 97 + ATPS 71, according to Table 1.0) (split into two first ATPS and recombined into one second ATPS), followed by magnetic beads with 2 mL binding buffer |
| Sample #2 | Magnetic beads with 2 mL binding buffer |

Purification of DNA

The target cfDNA in the urine sample partitioned to the polymer-rich top phase in the second ATPS and was concentrated down to 400 uL-600 uL. Binding buffer containing 3-7M guanidine was used.

2 mL of binding buffer was added respectively to the extracted top phase of Sample #1 and lysed Sample #2 which did not go through ATPS. 24 uL of magnetic bead was added into each tube. The mixture was then incubated on rotator for 5 minutes to prevent sediment of bead. The tube was then briefly spined down and placed on a magnetic rack for 2 minutes to immobilize bead at tube wall. Supernatant was discarded without disturbing the bead. 2 mL of binding buffer was added into each tube and tubes were rotated slowly on magnetic stand for 720° in total. The supernatant was again pipetted and discarded. 800 μL of washing buffer (70% ethanol, 0.001 M EDTA, 0.01 M Tris-HCl) was added to the sample, and the tube was rotated on the rack for 720° in total. The supernatant was discarded. The washing steps were performed twice. To enhance drying effectiveness the tubes were briefly spined down using bench-top microcentrifuge with the hinge facing outwards to collect any remaining washing buffer. The bead was then dried for 7 minutes on magnetic stand with cap opened. The beads-analyte complex was resuspended in 80 μL of Elution buffer (0.01 M Tris-HCl, 0.001 M EDTA) by continuous pipette mixing, followed by mild vortex. The tube was then placed on the magnetic rack for 1 minute. The supernatant was collected carefully into a DNA lo-bind tube without disturbing the magnetic beads for detection.

Detection of DNA

The steps to perform the detection of DNA for each sample are the same or similar to those as discussed with respect to Example 2a above. For the sake of brevity and simplicity of the present disclosure, the discussion of the detection steps is not reproduced here. The results were presented as average CT values.

Results

Recovery of DNA

Figure 4A:
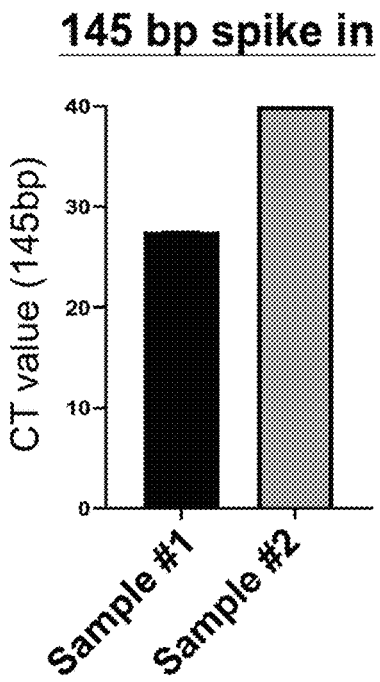
Figure 4B:
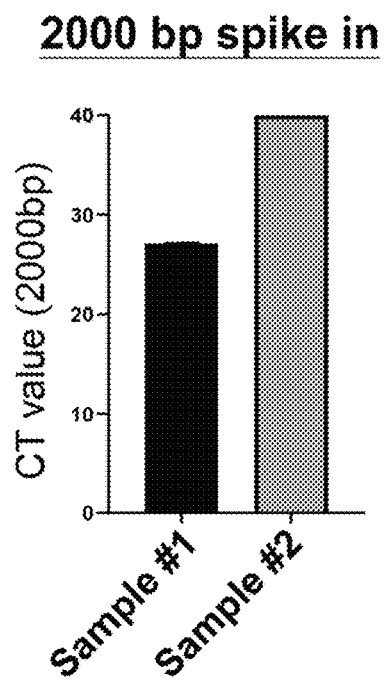

Now referring to FIGS. 4A-4B, both the average CT values of 145 bp DNA (FIG. 3A) and 2000 bp DNA (FIG. 4B) recovered from urine using magnetic beads with prior ATPS steps (Sample #1) and without prior ATPS steps (Sample #2) are shown. A high recovery of both the 145 bp DNA (average CT value of 27.47) and 2000 bp DNA (average CT value of 27.09) from urine Sample #1 are shown, while no detectable target DNA recovery is observed from urine Sample #2 (shown in Table 3.1). The results show that under the same condition, the recovery of DNA from large volume samples such as urine was significantly improved by incorporating parallel ATPS steps prior to magnetic beads purification.

TABLE 3.1 qPCR results of 145 bp and 2000 bp DNA oligos recovery in urine with or without two-step ATPS using magnetic beads.

| | 145 bp spike in | | 2000 bp spike in | |
|---|---|---|---|---|
| Urine | Sample #1 | Sample #2 | Sample #1 | Sample #2 |
| CT value | 27.384 | 40.000 | 27.007 | 40.000 |
| | 27.530 | 40.000 | 27.137 | 40.000 |
| | 27.497 | 40.000 | 27.120 | 40.000 |
| Average ± SD | 27.47 ± 0.08 | 40 ± 0 | 27.09 ± 0.07 | 40 ± 0 |

Overall, the recovery results have demonstrated that surprisingly, better DNA recovery is achieved when ATPS is incorporated in the plasma extraction workflow prior to purification using spin columns, even when additional steps of ATPS concentration and isolation are involved, which are potential sources for loss of target analyte during sample handling.

Example 4b: Urine Extraction Performance with Varying Polymers and Salts in the ATPS Compositions In this example, the ability to use ATPS with varying polymer molecular weight and component concentrations to integrate with magnetic beads for DNA recovery from urine sample is demonstrated. The materials used in this example are the same of similar as those discussed in the preceding examples. For the sake of brevity and simplicity of the present disclosure, the discussion of the materials is not reproduced here.

Urine Lysis

Urine samples were pre-treated with 200 uL of 0.1 M EDTA per 10 mL urine sample, vortexed thoroughly and centrifuged at 3000 rcf for 10 minutes. The supernatant was transferred to a new tube while the pellet was discarded. To digest unwanted protein and cells, 60 μL of Proteinase K (28.57 mg/mL) and 200 uL of a suitable lysis buffer were added to 2 mL of sample. 100 fg 145 bp oligo 100 ng of 1 kb+ DNA ladder was spiked into the above samples. The samples were then vortexed thoroughly till homogenous then left in a pre-heated 37° C. water bath to incubate for 15 minutes.

Two Phase System

The extraction procedure involves two sequential aqueous two-phase systems (ATPS) to isolate, purify and concentrate DNA from a urine sample. To evaluate the compatibility of such system, various polymers and salts have been investigated in the first ATPS for their phase separation properties and DNA extraction efficiencies. In the first ATPS, DNA partitions to the bottom phase and proteins partition to the top phase. The bottom phase, which amount to around 1 mL, was extracted carefully, and transferred to the second ATPS. As the composition of the bottom phase of ATPS strongly dependence on the constituents of ATPS, the bottom phase composition of the first ATPS differs from one another with various polymers and salts used. The composition of the second ATPS therefore have been modified accordingly to achieve a small top phase volume of around 150 µL. DNA partitions to the top phase of the second ATPS, and the top phase was extracted carefully for further purification and detection.

Extraction Process

To the first ATPS was added 2.26 mL of lysate. A dye was added to visualize the two phases, which resulted in a colored top phase. Due to the optimized combination of interactions with the components of the ATPS, the vast majority of DNA partitions to the bottom phase, while proteins were partitioned to the top phase. The solution was forced to become turbid by vigorous vortex for 15 seconds. Phase separation was then facilitated by centrifuge at 2300 ref for 6 minutes. After phase separation, the bottom phase had a volume of around 1 mL. The whole bottom phase was extracted carefully and transferred to the second ATPS. The composition of the second ATPS was formulated so that DNA partitions to the top phase. The mixture was vortexed for 15 seconds to yield a turbid solution and was centrifuged at 7000 rcf for 1 minute to achieve phase separation. The top phase volume in the resulting solution was around 150 µL. The small top-to-bottom phase volume ratio is beneficial for the concentration of DNA in the top phase. The top phase was then extracted carefully for further purification and detection of DNA.

Purification of DNA

The purification of DNA was done by magnetic beads extraction (also referred as "magnetic beads workflow"). The top phase from the second ATPS was transferred to a tube containing 600 µL of binding buffer (3-7M guanidinium). 6 µL of magnetic beads was added to the tube, and the sample was incubated with tilt rotation for 5 minutes. The tube was then briefly spined down and placed on a magnetic stand for 2 minutes to immobilize the beads at the tube wall. The supernatant was pipetted and discarded without disturbing the magnetic beads. To the sample was added 800 µL of binding buffer. The tubes were rotated on the rack for 720° in total. The supernatant was pipetted and discarded. 800 µL of washing buffer (70% ethanol, 0.001 M EDTA, 0.01 M Tris-HCl) was added to the sample, and the tube was rotated on the rack for 720° in total. The supernatant was pipetted and discarded. Washing step was performed twice, and the tube was placed on the rack with cap opened to allow the bead to dry. 40 µL of elution buffer (0.01 M Tris-HCl, 0.001 M EDTA) was added to the sample. The beads complex was resuspended by continuous pipette mixing, followed by mild vortex. The sample was incubated at room temperature for 3 minutes and was briefly spun down. The tube was then placed on the magnetic rack for 1 minute. The supernatant was collected carefully without disturbing the magnetic beads for detection.

Extraction Efficiency

Both first and second ATPS comprise a mixture of polymer and salt, in which the resulting top phase is rich in polymer, and bottom phase is rich in salt. To investigate the compatibility of the current system with different reagents, the extraction efficiency of DNA in different ATPS compositions have been studied, while keeping the volume ratios in the first and the second ATPS constant. To evaluate the DNA recovery performance, the samples were prepared containing 100 fg of 145 bp dsDNA to 2.5 ng per µL of eluant assuming 100% recovery.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The recovery was quantified by qPCR, and the results were summarized in FIGS. 3C-3D. The results were presented as average CT values.

Results

Figure 4C:
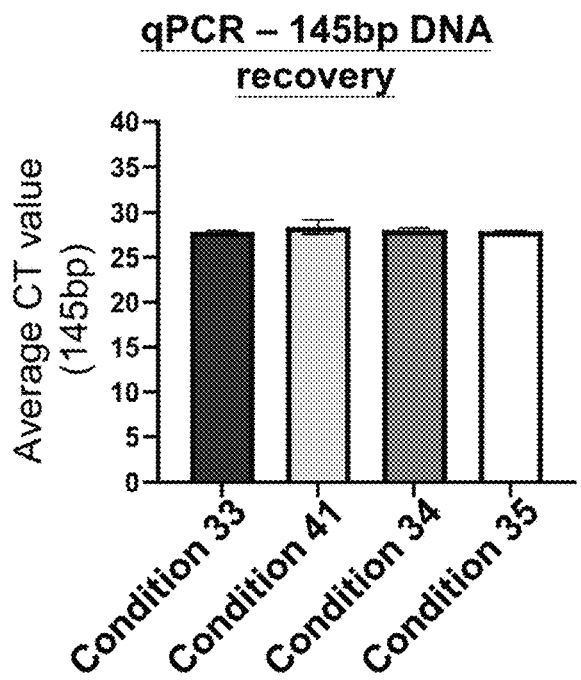
FIG. 4C is a graph showing the average CT values of 145 bp DNA recovered from urine using the ATPS conditions according to Table 3.3 in Example 4b.

Now referring to FIG. 4C, the average CT values of 145 bp DNA recovery using the first and second ATPS compositions according to Conditions 33, 41, 34, and 35 in Table 3.3 are compared. Conditions 33, 41, 34, and 35 correspond to the same polymer and salt combination with different polymer molecular weights, and their respective 145 bp DNA recovery results are reported in Table 3.3. The results demonstrate that all systems with alternate polymer molecular weights recover detectable levels of DNA from urine when combined with the magnetic beads workflow.

TABLE 3.3

DNA recovery from urine using ATPS with different polymers molecular weights and magnetic beads.

| Condition | First ATPS* | Second ATPS* | Average CT value (145 bp) + SD |
|---|---|---|---|
| 33 | ATPS 69 | ATPS 95 | 27.85 ± 0.12 |
| 41 | ATPS 107 | ATPS 72 | 27.9 ± 0.02 |
| 34 | ATPS 101 | ATPS 81 | 28.01 ± 0.24 |
| 35 | ATPS 113 | ATPS 89 | 27.89 ± 0.03 |

*ATPS compositions according to Table 1.0

Figure 4D:
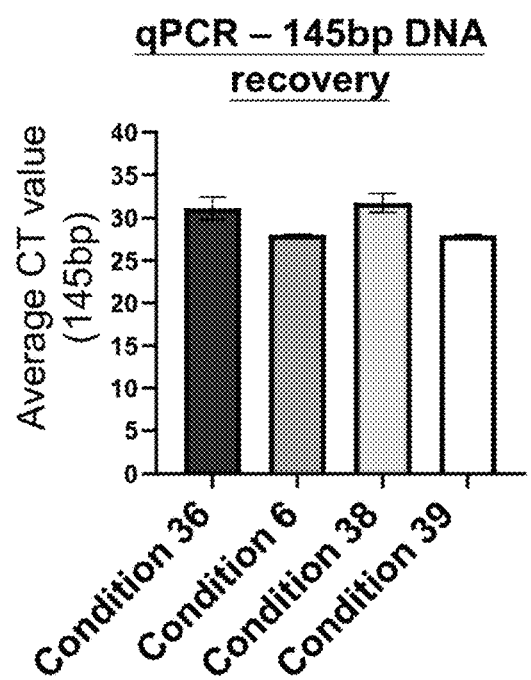
FIG. 4D is a graph showing the average CT values of 145 bp DNA recovered from urine using the ATPS conditions according to Table 3.4 in Example 4b.

Now referring to FIG. 4D, the average CT values of 145 bp DNA recovered from urine using the first and second ATPS compositions according to Conditions 36, 6, 38 and 39 in Table 3.4 are compared. Conditions 36, 6, 38 and 39 correspond to four different polymer and salt combinations, and their respective 145 bp DNA recovery results are reported in Table 3.4. The results demonstrate that all systems with alternate polymer and salt recover detectable DNA from urine using magnetic beads. All the samples showed acceptable DNA recovery, indicating the successful extraction of DNA with a wide range of reagents.

TABLE 3.4

DNA recovery from urine using ATPS with varying range of polymer and salts and magnetic beads.

| Condition | First ATPS* | Second ATPS* | Average CT value (145 bp) ± SD |
|---|---|---|---|
| 36 | ATPS 102 | ATPS 96 | 31.16 ± 1.3 |
| 6 | ATPS 107 | ATPS 72 | 28.02 ± 0.07 |
| 38 | ATPS 78 | ATPS 92 | 31.78 ± 1.1 |
| 39 | ATPS 108 | ATPS 83 | 27.95 ± 0.07 |

*ATPS compositions according to Table 1.0

Example 4c: Urine Extraction Performance with Varying ATPS Systems Using Magnetic Beads In this example, the ability to use different classes of ATPS systems (polymer-salt, polymer-polymer, micellar) to integrate with magnetic beads for DNA recovery from urine sample is demonstrated. The materials used in this example are the same of similar as those discussed in the preceding examples. For the sake of brevity and simplicity of the present disclosure, the discussion of the materials is not reproduced here.

Urine Lysis

Urine samples to be extracted with the polymer-polymer and polymer-salt ATPS systems were pre-treated with 200 µL of 0.1M EDTA per 10 mL urine sample, vortexed thoroughly and centrifuged at 3000 rcf for 10 minutes. The supernatant was transferred to a new tube while the pellet was discarded. Unwanted protein and cells present in pre-treated urine samples are lysed by adding 60 µL of Proteinase K (28.57 mg/mL) and 200 µL of a suitable lysis buffer to 2 mL of sample. The samples were then vortexed thoroughly till homogenous then left in a pre-heated 37° C. water bath to incubate for 15 minutes.

For the samples to be extracted with the micellar based ATPS system, urine samples were pre-treated with 200 uL of 0.1M EDTA per 10 mL urine sample and centrifuged at 3000 rcf for 10 minutes to collect the supernatant. 300 uL of a suitable lysis buffer was added to 1 mL pre-treated urine sample, vortexed thoroughly and incubated at room temperature for 3 minutes. Then to the sample was added 60 uL of protein precipitation buffer A (PPt A) (20% ZnCl w/v, 1% acetic acid w/v), and vortexed thoroughly until homogenous and centrifuged at 12000 rcf for 3 minutes. Other suitable protein precipitation buffers can be used in the method above instead of protein precipitation buffer A. The supernatant is extracted for further downstream processing while the pellet is discarded.

Extraction Process

Different varieties of aqueous two-phase systems (ATPS) similar to those discussed in Example 2c were prepared to efficiently extract cfDNA from urine samples. The 3 different varieties of ATPS systems prepared were summarized in Table 3.5. In the polymer-polymer and polymer-salt based ATPS systems, target cfDNA partitioned from the lysed sample into the bottom phase, while unwanted excess protein partitioned to the top phase. The opposite trend appeared in the micellar based ATPS system.

TABLE 3.5

Summary of experimental conditions with alternate ATPS classes.

| ATPS Class | ATPS Composition | Binding Step | Second Binding Step |
|---|---|---|---|
| 1. Polymer-polymer (P-P) | ATPS 1 | 1500 uL binding buffer added to the extracted polymer rich bottom phase | 800 uL binding buffer added to the magnetic beads |
| 2. Micellar | ATPS 50 | 500 uL binding buffer added to the extracted surfactant rich top phase | — |
| 3. Polymer-salt (P-S) | First ATPS: ATPS 63 | — | — |
|  | Second ATPS: ATPS 65 | 800 uL binding buffer added to the extracted polymer rich top phase of the second polymer-salt ATPS system | 800 uL binding buffer added to the magnetic beads |

The sample lysate was added to their respective ATPS systems: 1130 uL sample lysate into the polymer-polymer based system, 1360 uL extracted supernatant into the micellar based system. All ATPS tubes are vortexed thoroughly post sample lysate addition and vortexed thoroughly.

The polymer-polymer ATPS system is centrifuged at 2300 rcf for 6 minutes. The target cfDNA partitioned strongly to the bottom polymer rich phase. All the bottom phase (~300 uL) is extracted and transferred to a new 2 mL centrifuge tube for further processing.

The micellar ATPS system is centrifuged at 12000 rcf for 5 minutes. The target cfDNA partitioned strongly to the surfactant rich top phase. All the top phase (~280 uL) is extracted and transferred to a new 2 mL centrifuge tube for further processing.

The first polymer-salt ATPS system was centrifuged at 2300 rcf for 6 minutes. The target cfDNA partitioned strongly to the bottom salt rich phase. All the bottom phase (~1000 uL) was extracted and transferred to the second ATPS, where it was vortexed thoroughly before being centrifuged at 7000 rcf for 1 minute. The target cfDNA partitioned and was concentrated into a polymer-rich top phase of around 120 uL. It was then extracted and transferred to a new tube for further processing.

Purification of DNA

After extraction of phases containing target cfDNA from their respective ATPS systems, downstream processing includes addition of a solid phase medium and binding buffer for nucleic acid isolation from liquid medium, followed by washing of unwanted ions and molecules before the target nucleic acid is eluted by an elution buffer.

1500 uL of binding buffer (3-7M guanidine, 50 mM pH 7 $Na_2HPO_4/NaH_2PO_4$) is added to the extracted polymer-rich bottom phase of the polymer-polymer system. 500 uL of binding buffer (3-7M guanidine) is added to the extracted surfactant rich top phase of the micellar system. 800 uL of binding buffer (1-5M guanidine) is added to the extracted polymer rich top phase of the second polymer-salt ATPS system. 6 uL of magnetic bead are then added to all centrifuge tubes containing the mixture of extracted phase and binding buffer, and put onto a rotator to incubate for 5 minutes. The target cfDNA will bind to the magnetic beads to form a beads-analyte complex. After incubation, all tubes are briefly centrifuged before placing on magnetic racks, where the applied magnetic field would attract the cfDNA bound magnetic bead. The supernatant is then taken and discarded, leaving the magnetic beads bound to the inner wall of the centrifuge tube. A second binding buffer wash step is performed for the polymer-polymer and polymer-salt systems. 800 uL of binding buffer (3-7M guanidine, 50 mM pH 7 $Na_2HPO_4/NaH_2PO_4$) is added to the magnetic beads from the polymer-polymer system, and 800 uL of binding buffer (1-5M guanidine) is added to the magnetic beads from the polymer-salt system. The centrifuge tubes are then vortexed thoroughly and briefly spun down before being placed back on the magnetic racks. The supernatant is discarded once all the magnetic beads have been bound to the inner side of the centrifuge wall.

800 uL of original washing buffer (70% v/v EtOH, 1 mM EDTA, 10 mM Tris-HCl) are added to magnetic beads from the polymer-polymer and polymer-salt system, while 500 uL of RPE washing buffer (80% v/v EtOH, 0.1M NaCl, 10 mM Tris-HCl) is added to magnetic beads from the micellar system. The centrifuge tubes are turned 720° on the magnetic racks before washing buffer is discarded. The procedure is repeated for a second wash. The centrifuge tubes are then briefly centrifuged before being placed back on the magnetic rack, any excess washing buffer remaining in the centrifuge tube is then discarded. The magnetic beads are allowed to dry at room temperature for 7 minutes for polymer-polymer and polymer-salt systems, and 10 minutes for micellar systems.

After the magnetic beads are allowed to dry, 20 uL of elution buffer (10 mM Tris-HCl, 1 mM EDTA) are used to resuspend the magnetic beads, then left to incubate at room temperature for 3 minutes. The target cfDNA will be eluted from the magnetic beads into the elution buffer. The tubes are then placed back onto the magnetic racks and the elution buffer is extracted once the magnetic beads are all bound.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Figure 4E:
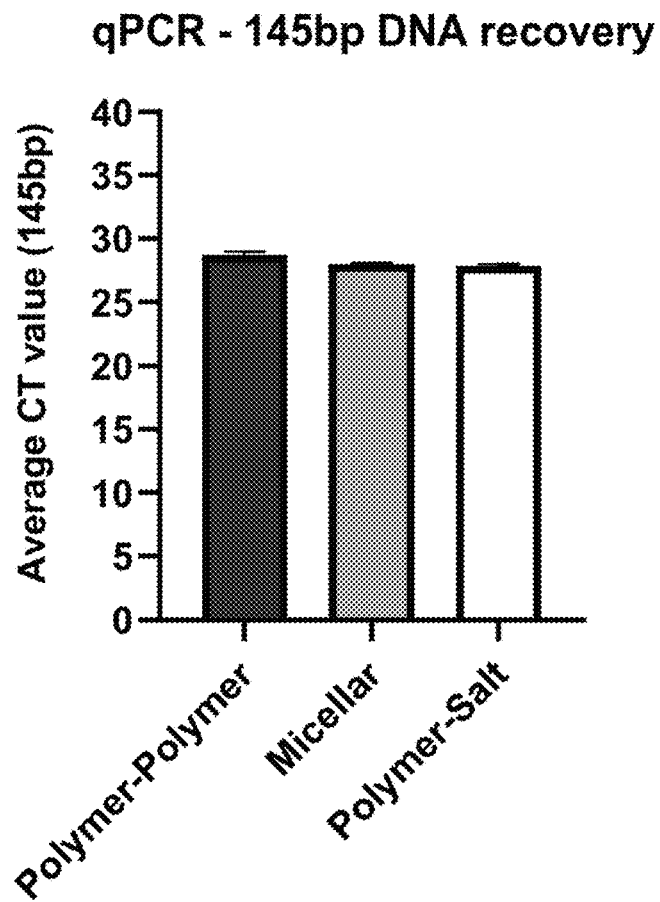
FIG. 4E is a graph showing the average CT values of 145 bp DNA recovery from urine using 3 different types of ATPS and magnetic beads, according to Example 4c.

Now referring to FIG. 4E, the average CT values of 145 bp DNA recovered from urine when extracted using the different types of ATPS system, according to Table 3.6, are shown. The results show that the DNA recovery efficiency of these three systems are comparable as the difference in average CT values among the polymer-polymer system (average CT value=28.73), micellar system (average CT value=27.99) and polymer-salt system (average CT value=27.85) are all within 1 CT value. This demonstrates that a different variety of ATPS classes can recover DNA in a similar degree when optimized.

TABLE 3.6 qPCR results of 145 bp DNA recovery in urine with different ATPS classes using magnetic beads.

| | Polymer-polymer | Micellar | Polymer-salt |
|---|---|---|---|
| CT value | 28.46 | 27.87 | 27.75 |
| | 28.72 | 28.01 | 27.99 |
| | 28.99 | 28.08 | 27.82 |
| Average ± SD | 28.73 ± 0.27 | 27.99 ± 0.11 | 27.85 ± 0.12 |

Example 5a: Comparing DNA Recovery Efficiency from Urine Using Spin Column with and without Prior Aqueous Two-Phase System (ATPS) Steps In this example, DNA recovery efficiencies from urine using spin column (i) with prior phase separation using ATPS systems in accordance with the method of the present disclosure; and (ii) without prior ATPS steps are compared. The materials used in this example are the same of similar as those discussed in the preceding examples. For the sake of brevity and simplicity of the present disclosure, the discussion of the materials is not reproduced here.

Urine Lysis

Urine samples were collected from 4 different donors. The samples from each donor were aliquoted into tubes of 40 mL per tube and divided into 2 sets, with each set containing 1 sample from each donor.

All 2 sets of urine samples were pre-treated with 200 uL of 0.1M EDTA per 10 mL urine sample, vortexed thoroughly and centrifuged at 3000 rcf for 10 minutes. The supernatant was transferred to a new tube while the pellet was discarded.

Unwanted protein and cells present in pre-treated urine samples are lysed by adding 1200 uL of (28.57 mg/mL) Proteinase K and 4 mL of a suitable lysis buffer to 40 mL of sample per donor. The samples were then vortexed thoroughly till homogenous then left in a pre-heated 37° C. water bath to incubate for 15 minutes.

Extraction Process

Two different aqueous two-phase systems (ATPS) were prepared to efficiently extract cfDNA from urine samples. The steps to perform ATPS extraction for the preparation of urine Sample #3 and urine Sample #4 in this example are the same or similar to those as discussed with respect to Example 4a. For the sake of brevity and simplicity of the present disclosure, the discussion of the ATPS steps is not reproduced here. The urine sample sets are summarized in Table 4.0 below.

TABLE 4.0

Summary of test conditions for urine extraction and purification.

| Sample | Condition |
|---|---|
| Sample #3 | Dual ATPS (ATPS 97 + ATPS 71, according to Table 1.0) (split into two first ATPS and recombined into one second ATPS), followed by EconoSpin column with 2 mL binding buffer containing 3-7M guanidine |
| Sample #4 | EconoSpin column with 2 mL binding buffer containing 3-7M guanidine |

Purification of DNA

The target cfDNA in the urine sample partitioned to the polymer-rich top phase in the second ATPS and been concentrated down to 400 uL-600 uL. The top phase was isolated for further processing.

3-7M solution of guanidine was used as a binding buffer. 2 mL of 3-7M guanidine was added to (~400 uL-600 uL) extracted second ATPS polymer-rich top phase from urine set 3 (Sample #3) and vortexed thoroughly. Urine sample set 4 (Sample #4), which did not go through the ATPS purification and concentration, was mixed with 2 mL 3-7M guanidine and vortexed thoroughly. Each urine sample was then added to EconoSpin column for DNA attached to the QIAvac 24 Plus vacuum manifold with the appropriate extenders (3 mL and 20 mL). A pressure of 900 mbar was applied to the vacuum manifold and sample lysate was allowed to flow through the spin column. The target cfDNA will bind to the spin column and be retained while the sample lysate flow through (also referred as 'supernatant') is discarded by the vacuum manifold. After all possible sample lysate has flowed through the spin column, the extenders are removed and discarded. The spin columns are removed from the manifold and inserted into 2 mL waste tubes. 500 uL of RPE wash buffer (80% v/v EtOH, 0.1M NaCl, 0.01M Tris-HCl) were added to the spin columns and centrifuged at 12000 rcf for 30 seconds. The flow through is discarded and the spin column is further centrifuged at 16000 rcf for 2 minutes to remove any excess RPE wash buffer. The spin columns were then placed in new 1.5 mL centrifuge tubes where 80 uL of elution buffer (0.01M Tris-HCl, 1 mM EDTA) were pipetted directly onto the silica membrane and allowed to incubate at room temperature for 3 minutes. The spin columns were centrifuged at 12000 rcf for 1 minute to elute the target cfDNA into 1.5 mL centrifuge tube.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Recovery of DNA

In urine Sample #3, all lysate sample flowed through the spin column within 1 minute. In urine Sample #4, only 25% of the sample lysate had passed through the spin column in the first 60 minutes. Without parallel ATPS, increased flow time (1 hour) was needed in order for unprocessed lysates to pass through the column completely.

Figure 5A:
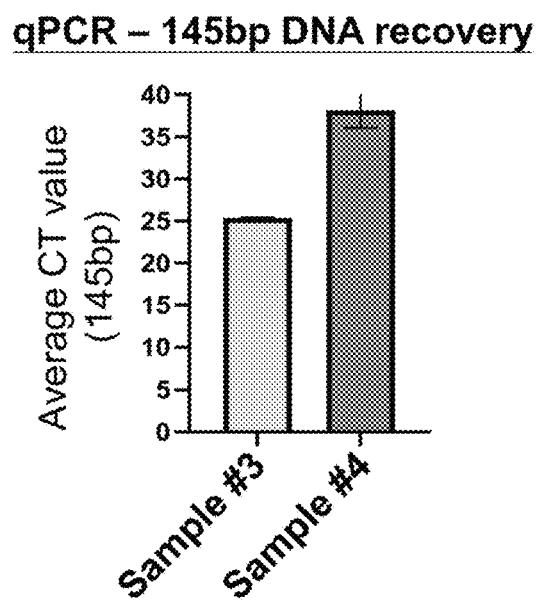
Figure 5B:
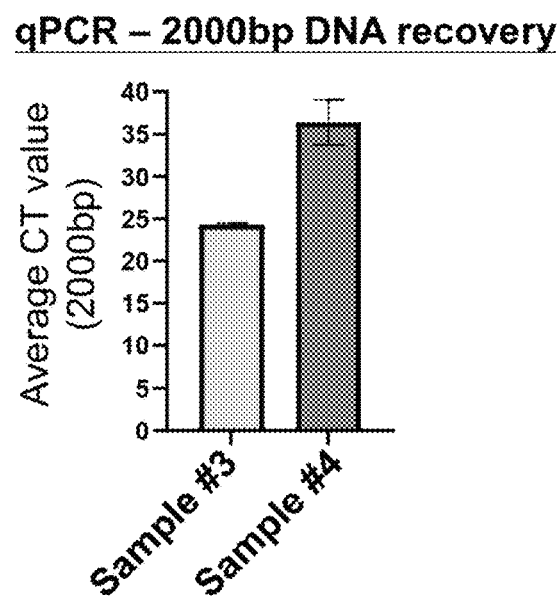

Now referring to FIGS. 5A-5B, the average CT values of 145 bp and 2000 bp DNA recovered from urine using spin column with prior ATPS steps (Sample #3) and without prior ATPS steps (Sample #4) are shown. For 145 bp DNA, Urine Sample #3 had high recovery (average CT value of 25.36±0.08), yet poor recovery (average CT value of 38.15±2.10) is observed from urine Sample #4, according to Table 4.1, and similar results is observed in the 2000 bp DNA recovery. As shown by the results, concentrating the urine lysates by parallel ATPS prior to spin column extraction has enhanced the efficiency of the downstream processing and significantly improved the recovery of 145 bp and 2000 bp DNA.

TABLE 4.1 qPCR results of 145 bp and 2000 bp DNA oligos recovery in urine with or without two-step ATPS using spin column.

| | 145 bp spike in | | 2000 bp spike in | |
| --- | --- | --- | --- | --- |
| Urine | Sample #3 | Sample #4 | Sample #3 | Sample #4 |
| CT value | 25.282 | 35.341 | 24.099 | 33.675 |
| | 25.419 | 40.000 | 24.427 | 40.000 |
| | 25.299 | 39.481 | 24.246 | 36.619 |
| | 25.427 | 37.780 | 24.479 | 35.390 |
| Average ± SD | 25.36 ± 0.08 | 38.15 ± 2.10 | 24.31 ± 0.17 | 36.42 ± 2.67 |

Overall, the recovery results have demonstrated that surprisingly, better DNA recovery is achieved when ATPS is incorporated in the plasma extraction workflow prior to purification using spin columns, even when additional steps of ATPS concentration and isolation are involved, which are potential sources for loss of target analyte during sample handling.

Example 5b: Urine Extraction Performance with Varying Polymers and Salts in the ATPS Compositions In this example, the ability to use ATPS with varying polymer MW and component concentrations to integrate with spin column for DNA recovery from urine sample is demonstrated. The materials used in this example are the same of similar as those discussed in the preceding examples. For the sake of brevity and simplicity of the present disclosure, the discussion of the materials is not reproduced here.

Urine Lysis

In this example, urine samples were pre-treated with 200 uL of 0.1 M EDTA per 10 mL urine sample, vortexed thoroughly and centrifuged at 3000 rcf for 10 minutes. The supernatant was transferred to a new tube while the pellet was discarded. To digest unwanted protein and cells present in pre-treated urine samples, 1200 μL of Proteinase K (28.57 mg/mL) and 4 mL of a suitable lysis buffer were added to 40 mL of sample. 100 fg 145 bp DNA and 100 ng GR 1 kb+ ladder were spiked into the above sample. The samples were then vortexed thoroughly till homogenous then left in a pre-heated 37° C. water bath to incubate for 15 minutes.

Two Phase System

The extraction procedure involves two sequential aqueous two-phase systems (ATPS) to isolate, purify and concentrate DNA from urine samples, similar to the ones described in preceding examples. In the first ATPS, DNA partitions to the bottom phase and proteins partition to the top phase. The bottom phase, which amount to around 1 mL, was extracted carefully and transferred to the second ATPS. As the composition of the bottom phase of ATPS strongly dependence on the constituents of ATPS, the bottom phase composition of the first ATPS differs from one another with various polymers and salts used. The composition of the second ATPS therefore have been modified accordingly to achieve a small top phase volume of around 150 μL. DNA partitions to the top phase of the second ATPS, and the top phase was extracted carefully for further purification and detection.

Extraction Process

To the first ATPS was added 2.22 mL of lysate. A dye was added to visualize the two phases, which resulted in a colored top phase. In this example, the vast majority of DNA partitioned to the bottom phase, while proteins partitioned to the top phase. The solution was forced to become turbid by vigorous vortex for 15 seconds. Phase separation was then facilitated by centrifuge at 2300 ref for 6 minutes. After phase separation, the bottom phase had a volume of around 1 mL. The whole bottom phase was extracted carefully and transferred to the second ATPS. The second ATPS mixture was vortexed for 15 seconds to yield a turbid solution and was centrifuged at 7000 ref for 1 minute to achieve phase separation. The top phase volume in the resulting solution was around 150 μL, which was then extracted carefully for further purification and detection of DNA.

Purification of DNA

The purification of DNA was done by spin column extraction similar to the steps discussed in Example 5a. The top phase from the second ATPS was transferred to a tube containing 800 μL of binding buffer (1-5M guanidinium). Mixed thoroughly, 800 μL of the solution was transferred to a spin column (EconoSpin) and was centrifuged for 30 seconds at 12,000 rcf. The flow-through was discarded. The process was repeated until all sample had been passed through the spin column. To the spin column was added 800 μL of washing buffer (70% ethanol, 0.001 M EDTA, 0.01 M Tris-HCl), and was centrifuged for 30 seconds at 12,000 rcf. The washing was performed twice, and the tube was centrifuged for 2 minutes at 16,000 rcf to dry. 40 μL of elution buffer (0.01 M Tris-HCl, 0.001 M EDTA) was added to the sample. The sample was incubated at room temperature for 3 minutes. The elution was collected to a collection tube by centrifuge for 1 minute at 12,000 rcf for detection.

Extraction Efficiency

Both first and second ATPS comprise a mixture of polymer and salt, in which the resulting top phase is rich in polymer, and bottom phase is rich in salt. In this example, the extraction efficiency of DNA in different ATPS compositions have been studied, while keeping the volume ratios in the first and the second ATPS constant. To evaluate the DNA recovery performance, the samples were prepared containing 100 ng of DNA ladder in 2 mL urine, amounting to 2.5 ng per μL of eluant assuming 100% recovery.

Detection of DNA

The steps to perform the detection of DNA for each sample are the same or similar to those as discussed with respect to Example 1a above. For the sake of brevity and simplicity of the present disclosure, the discussion of the detection steps is not reproduced here. The results were presented as average CT values.

Results

Figure 5C:
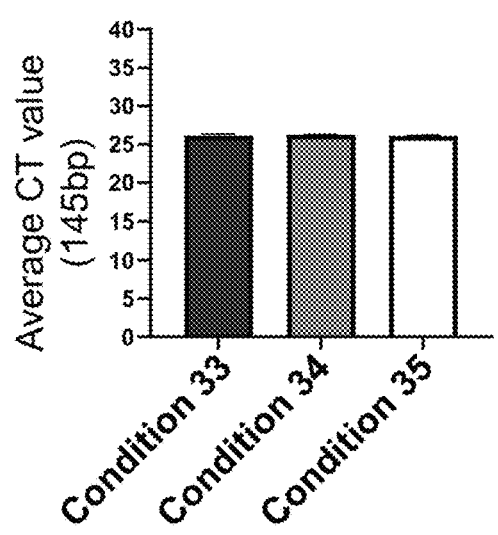
FIG. 5C is a graph showing the average CT values of 145 bp DNA recovered from urine using the ATPS conditions according to Table 4.3 in Example 5b.

Now referring to FIG. 5C, the average CT values of 145 bp DNA recovered from urine the first and second ATPS compositions according to Conditions 33, 34 and 35 in Table 4.3 are compared. Conditions 33, 34, and 35 correspond to the same polymer and salt combination with three different polymer molecular weights, and their respective 145 bp DNA recovery results are reported in Table 4.3. The results demonstrate that all systems with alternate polymer molecular weights recover detectable DNA from urine when combined with the spin column workflow.

TABLE 4.3

DNA recovery from urine using ATPS with different polymers molecular weights and spin column.

| Condition | First ATPS* | Second ATPS* | Average CT value (145 bp) ± SD |
|---|---|---|---|
| 33 | ATPS 69 | ATPS 95 | 26.15 ± 0.19 |
| 34 | ATPS 101 | ATPS 81 | 26.22 ± 0.07 |
| 35 | ATPS 113 | ATPS 89 | 26.06 ± 0.10 |

*ATPS compositions according to Table 1.0

Figure 5D:
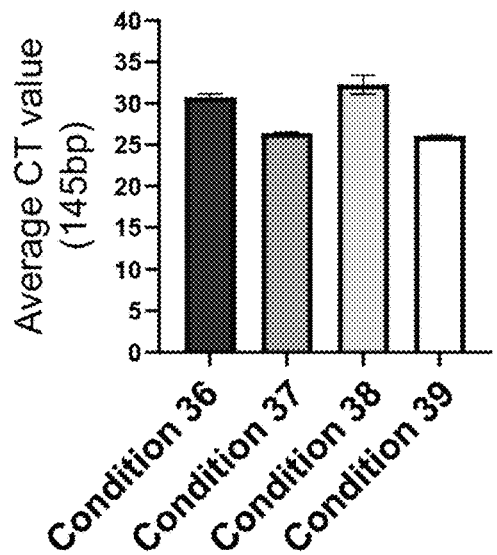
FIG. 5D is a graph showing the average CT values of 145 bp DNA recovered from urine using the ATPS conditions according to Table 4.4 in Example 5b.

Now referring to FIG. 5D, the average CT values of 145 bp DNA recovered from urine using the first and second ATPS compositions according to Conditions 36-39 in Table 4.4 are compared. Conditions 36, 37, 38 and 39 correspond to four different polymer and salt combinations, and their respective 145 bp DNA recovery results are reported in Table 4.4. The results demonstrate that all systems with alternate polymer and salt recover detectable DNA from urine using spin column.

TABLE 4.4

DNA recovery from urine using ATPS with varying range of polymer and salts and spin column.

| Condition | First ATPS* | Second ATPS* | Average CT value (145 bp) ± SD |
|---|---|---|---|
| 36 | ATPS 102 | ATPS 96 | 30.76 ± 0.39 |
| 37 | ATPS 116 | ATPS 90 | 26.41 ± 0.07 |
| 38 | ATPS 78 | ATPS 92 | 32.27 ± 1.16 |
| 39 | ATPS 108 | ATPS 83 | 26.06 ± 0.06 |

*ATPS compositions according to Table 1.0

Example 5c: Urine Extraction Performance with Varying ATPS Systems Using Spin Column In this example, the ability to use different classes of ATPS systems (polymer-salt, polymer-polymer, micellar) to integrate with spin column for DNA recovery from urine sample is demonstrated. The materials used in this example are the same of similar as those discussed in the preceding examples. For the sake of brevity and simplicity of the present disclosure, the discussion of the materials is not reproduced here.

Urine Lysis

In this example, urine samples to be extracted with the polymer-polymer and polymer-salt ATPS systems were pre-treated with 200 uL of 0.1M EDTA per 10 mL urine sample, vortexed thoroughly and centrifuged at 3000 rcf for 10 minutes. The supernatant was transferred to a new tube while the pellet was discarded. Unwanted protein and cells present in pre-treated urine samples are lysed by adding 1200 μL of Proteinase K (28.57 mg/mL) and 4 mL of a suitable lysis buffer to 40 mL of sample. The samples were then vortexed thoroughly till homogenous then left in a pre-heated 37° C. water bath to incubate for 15 minutes.

For the samples to be extracted with the micellar based ATPS system, urine samples were pre-treated with 200 uL of 0.1M EDTA per 10 mL urine sample and centrifuged at 3000 rcf for 10 minutes to collect the supernatant. 300 uL of suitable lysis was added to 1 mL pre-treated urine sample, vortexed thoroughly and incubated at room temperature for 3 minutes. Then to the sample was added 112.5 uL of protein precipitation buffer A (PPt A) (20% ZnCl w/v, 1% acetic acid w/v), and vortexed thoroughly until homogenous and centrifuged at 12000 rcf for 3 minutes. Other suitable protein precipitation buffers can be used in the method above instead of protein precipitation buffer A. The supernatant is extracted for further downstream processing while the pellet is discarded.

Extraction Process

The extraction process and the 3 different classes of ATPS systems prepared were the same as those as discussed in Example 4c: 1. Polymer-polymer based (P-P); 2. Micellar; and 3. Dual ATPS—Polymer-salt based (P-S). For the sake of brevity and simplicity of the present disclosure, the discussion of the preparation of the above ATPS composition and the extraction process is not reproduced here.

The three different varieties of ATPS and the subsequent binding steps for this example are summarized in Table 4.5.

TABLE 4.5

Summary of experimental conditions with alternate ATPS classes.

| ATPS Class | ATPS Composition | Binding Step |
|---|---|---|
| 1. Polymer-polymer (P-P) | ATPS 1 | 1500 uL binding buffer added to the extracted polymer rich bottom phase |
| 2. Micellar | ATPS 50 | 500 uL binding buffer added to the extracted surfactant rich top phase |
| 3. Polymer-salt (P-S) | First ATPS: ATPS 63 | — |
| | Second ATPS: ATPS 65 | 800 uL binding buffer added to the extracted polymer rich top phase of the second polymer-salt ATPS system |

The sample lysate was added to their respective ATPS systems: 1130 uL sample lysate into the polymer-polymer based system, 1360 uL extracted supernatant into the micellar system. All ATPS tubes were vortexed thoroughly post sample lysate addition and vortexed thoroughly.

The polymer-polymer ATPS system was centrifuged at 2300 rcf for 6 minutes. The target cfDNA partitioned strongly to the bottom polymer rich phase. All the bottom phase (~300 uL) was extracted and transferred to a new 2 mL centrifuge tube for further processing.

The micellar ATPS system was centrifuged at 12000 rcf for 5 minutes. The target cfDNA partitioned strongly to the surfactant rich top phase. All the top phase (~280 uL) was extracted and transferred to a new 2 mL centrifuge tube for further processing.

The first polymer-salt ATPS system was centrifuged at 2300 rcf for 6 minutes. The target cfDNA partitioned strongly to the bottom salt rich phase. All the bottom phase (~1000 uL) was extracted and transferred to the second ATPS, where it was vortexed thoroughly before being centrifuged at 7000 rcf for 1 minute. The target cfDNA partitioned and was concentrated into a polymer-rich top phase of around 120 uL. It was then extracted and transferred to a new tube for further processing.

Purification of DNA

After extraction of phases containing target cfDNA from their respective ATPS systems, downstream processing includes addition of a solid phase medium and binding buffer for nucleic acid isolation from liquid medium, followed by washing of unwanted ions and molecules before the target nucleic acid was eluted by an elution buffer.

1500 uL of binding buffer (3-7M guanidinium, 50 mM pH 7 $Na_2HPO_4/NaH_2PO_4$) was added to extracted polymer rich bottom phase of the polymer-polymer system. 500 uL of binding buffer (3-7M guanidinium) was added to the extracted surfactant rich top phase of the micellar system. 800 uL of each sample was then added to individual Econo-Spin column for DNA and centrifuged for 30 seconds at 12,000 rcf. The target cfDNA was bound to the spin column and retained while the sample lysate flowed through was discarded by the vacuum manifold. The flow-through was discarded and the process was repeated until all sample had flowed through the spin column. 500 uL of RPE wash buffer (80% v/v EtOH, 0.1M NaCl, 0.01M Tris-HCl) were added to the spin columns and centrifuged at 12000 rcf for 30 seconds. The flow through was discarded and the spin column was further centrifuged at 16000 rcf for 2 minutes to remove any excess RPE wash buffer. The spin columns were then placed in new 1.5 mL centrifuge tubes where 80 uL of elution buffer (0.01M Tris-HCl, 1 mM EDTA) were pipetted directly onto the silica membrane and allowed to incubate at room temperature for 3 minutes. The spin columns were centrifuged at 12000 rcf for 1 minute to elute the target cfDNA into 1.5 mL centrifuge tube.

Detection of DNA

The steps to perform the detection of DNA for each sample are the same or similar to those as discussed with respect to Example 2a above. For the sake of brevity and simplicity of the present disclosure, the discussion of the detection steps is not reproduced here. The results were presented as average CT values.

Recovery of DNA

Results

Figure 5E:
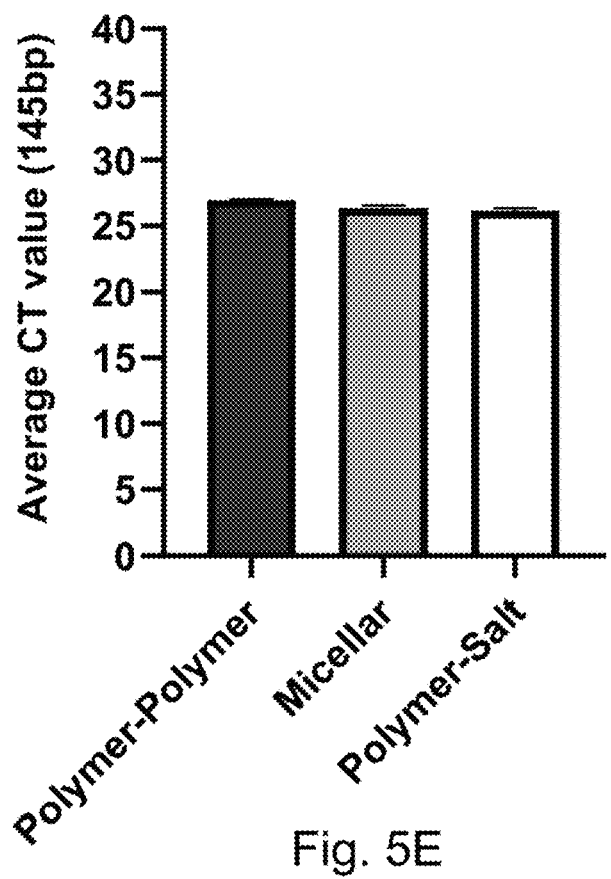
FIG. 5E is a graph showing the average CT values of 145 bp DNA recovery from urine using 3 different types of ATPS and spin column, according to Example 5c.

Now referring to FIG. 5E, the average CT values of 145 bp DNA recovered from urine using the different types of ATPS system (polymer-polymer, micellar, polymer-salt), according to Table 4.6, are shown. The results show that all three systems are effective at providing satisfactory DNA recovery from urine.

TABLE 4.6 qPCR results of 145 bp DNA recovery in urine with different ATPS classes using spin column.

| | Polymer-polymer | Micellar | Polymer-salt |
|---|---|---|---|
| CT value | 26.86 | 26.23 | 25.94 |
| | 27.01 | 26.27 | 26.20 |
| | 26.96 | 26.56 | 26.31 |
| Average ± SD | 26.94 ± 0.08 | 26.35 ± 0.18 | 26.15 ± 0.0.19 |

Example 6: Consolidated Results

Magnetic Beads as Solid Phase

Figure 6A:
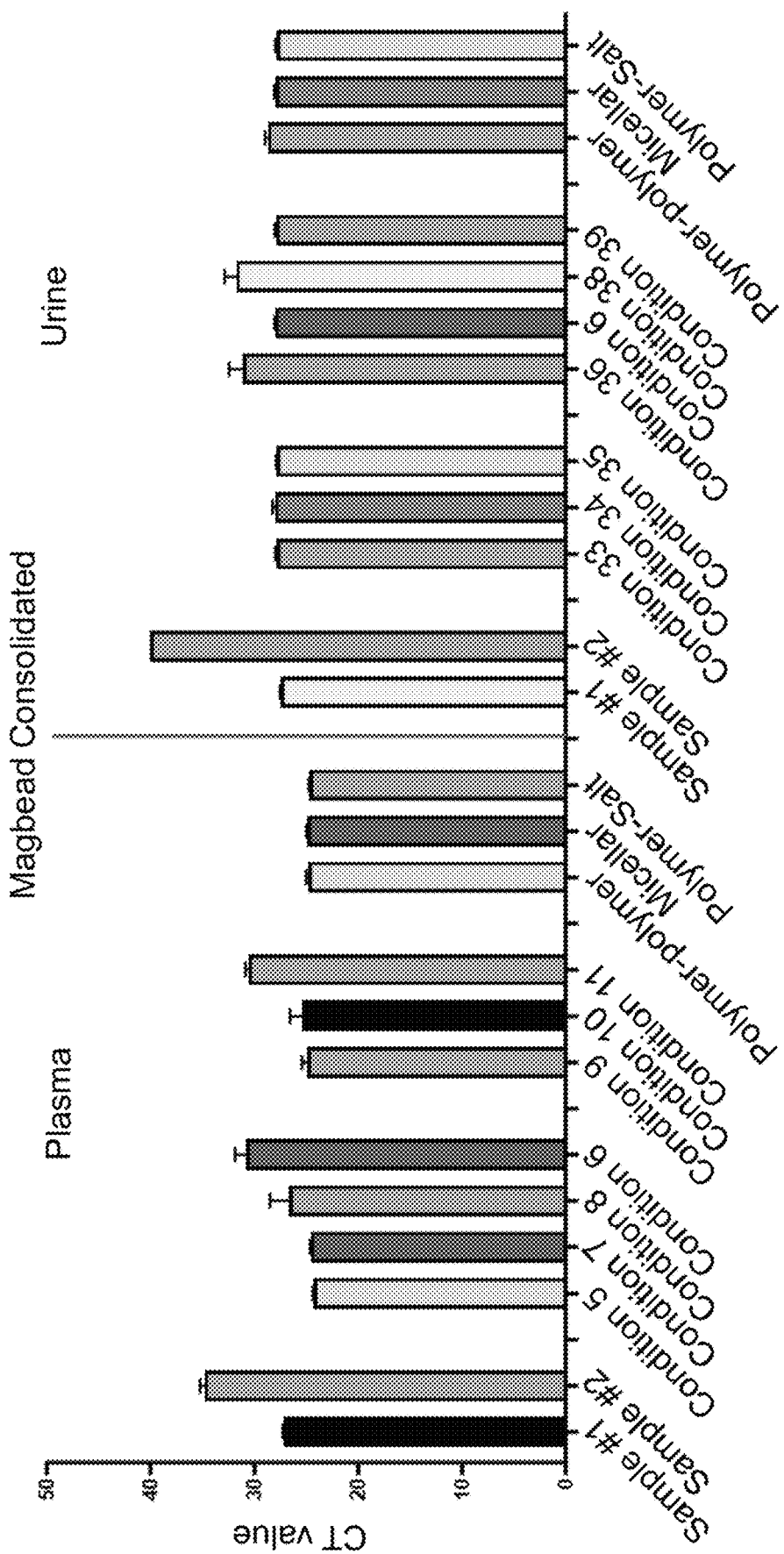
FIG. 6A is a consolidated data representation showing the average CT values of 145 bp DNA recovered from plasma and urine using magnetic beads, according to Examples 2a-c and Examples 4a-c.

Now referring to FIG. 6A, a consolidated data representation showing the CT values of 145 bp DNA recovered from plasma and urine using magnetic beads (combining Examples 2a-c and Examples 4a-c). As shown in FIG. 6A, all conditions with prior ATPS steps achieved higher DNA recovery compared to the conditions without prior ATPS steps, i.e., plasma Sample #2 and urine Sample #2 in FIG. 6A, which both resulted in Ct values close to 40 (also see Sample #2 in Example 2a and Sample #2 in Example 4a). This highlights the significance of incorporating ATPS steps in the extraction of urine prior to magnetic beads purification in order to achieve satisfactory DNA recovery.

Spin Column as Solid Phase

Figure 6B:
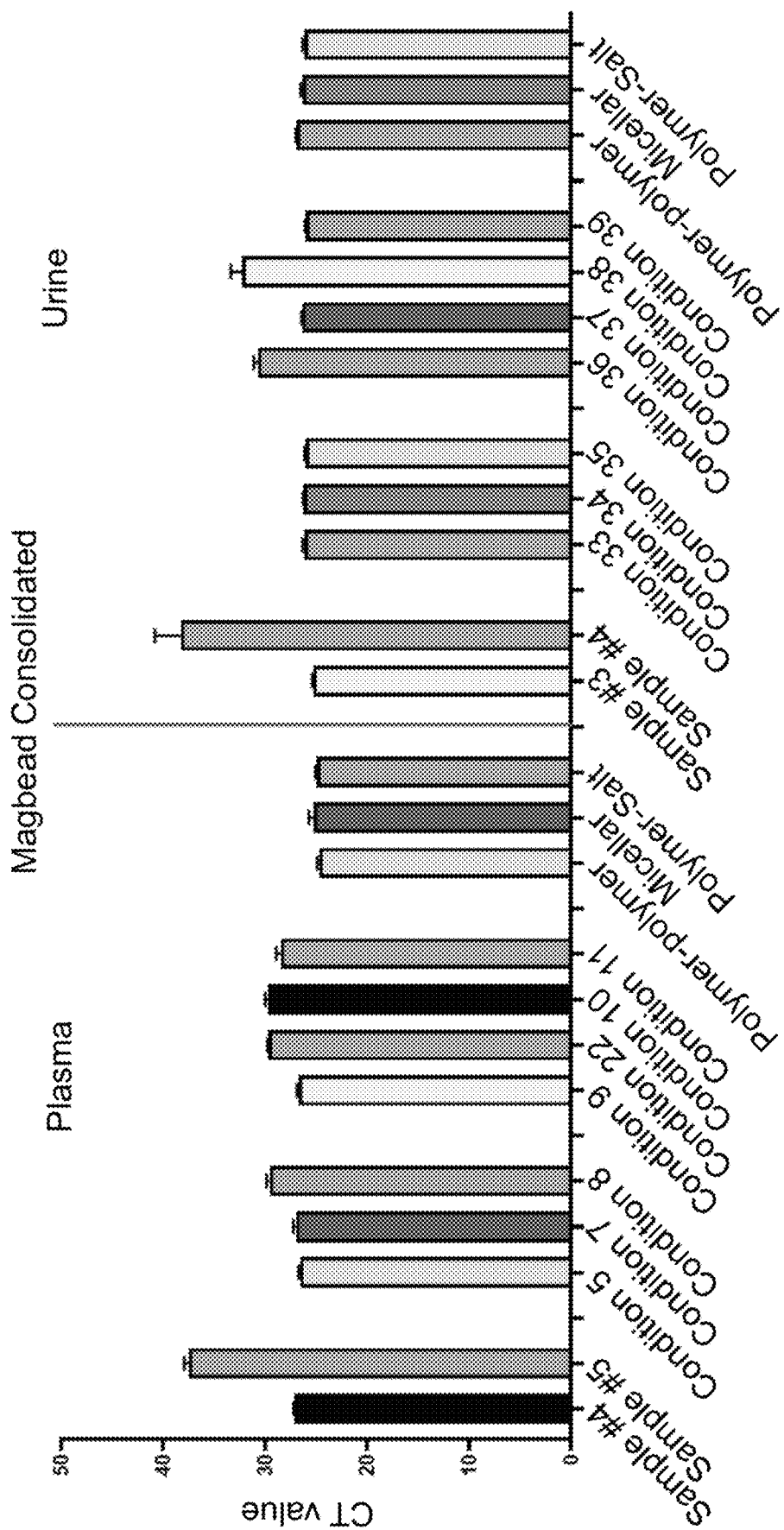
FIG. 6B is consolidated data representation showing the average CT values of 145 bp DNA recovered from plasma and urine using spin column, according to Examples 3a-c and Examples 5a-c.

Now referring to FIG. 6B, a consolidated data representation showing the CT values of 145 bp DNA recovered from plasma and urine using spin columns (combining Examples 3a-c and Examples 5a-c). Similarly, as shown in FIG. 6B, all conditions with prior ATPS steps have achieved higher DNA recovery compared to the conditions without prior ATPS steps, i.e., plasma Sample #5 and urine Sample #4 in FIG. 6B, which both resulted in Ct values close to 40 (see Sample #5 in Example 3a and Sample #4 in Example 5a). This highlights the benefits of incorporating ATPS steps in the extraction of plasma prior to spin column purification in order to achieve satisfactory DNA recovery.

In summary, adding an ATPS step prior to the solid phase extraction workflow provides the following benefits when compared with non-ATPS processed samples:

Significant Reduction in Reagent Consumption

As can be seen from the examples shown herein, adding one or more ATPS steps significantly reduced the binding buffer amount needed for unprocessed lysates in some examples. For example, adding a 2-step ATPS system before solid phase extraction reduced the binding buffer needed for a 40 mL bulk fluid sample to only 2 mL. This is due to the small target-rich phase produced by the first or second ATPS. The magnitude of reduced reagent consumption becomes even more apparent when sample input volume is increased, as a larger input volume exponentially requires more binding buffer, while ATPS processing can be modified to keep the top phase volume constant.

In some examples, high DNA recovery was achieved without requiring higher quantity of magnetic beads to shift the binding equilibrium for better yield, thereby reducing expensive magnetic bead and hazardous binding buffer utilization.

Significant Decrease in Column Flow Through Time

In some examples, adding a parallel ATPS step significantly and surprisingly reduced the column flow through time from 1 hour to 1 minute.

Simplified Laboratory Setup

In some examples, with the much smaller sample lysate volume, custom large volume extenders would not be required when ATPS sample lysate concentration is applied. A special vacuum manifold would not be needed, and usage of centrifuges for sample lysate pass through can be achieved.

Overall, the results demonstrate the surprising efficiencies of a system that combines one or more ATPS extraction workflows with different solid phase media for purification in the extractions of analytes from different clinical biological samples.

Example 7: Comparison of Total DNA Recovery Using the Presently Disclosed Method to Commercially Available Extraction Kits Example 7a DNA extraction from urine using an exemplary method and kit (referred as 'present extraction method' or 'Phase' herein) as described in Example 5a was compared to that of the Zymo Quick-DNA Urine kit ('Zymo'), NextPrep-Mag Urine cfDNA Isolation Kit ('NextPrep kit'), Norgen Urine DNA Isolation kit-spin column ('Norgen'), and Wizard Plus miniprep DNA purification system ('Wizard'), which are all commercially available. For each competitor's kit, the maximum input volume of urine sample as specified by the manufacturer was used, and the extraction was performed by following the manufacturer's instruction. The comparison was performed using cell-free urine for the commercially available kits (Conditions A-D in Table 6) as well as the present extraction method (Condition E in Table 6). Additionally, as a comparison, we performed one batch of 40 mL extraction using crude urine (unspun urine with cells) with the present extraction method (Condition F in Table 6) to assess if the present extraction method can perform equally well with the cells. Urine samples were provided by 4 males and 4 females (n=8 for each kit). The input and elution volume of each kit were normalized to a 100:1 ratio, and the extraction time is compared in Table 6.

TABLE 6

Comparisons of yield and efficiency with normalized input: elution volume ratio.

| Cond. | Extraction system | Input volume | Elution volume | Extraction time | Average 145 bp DNA recovery (copies/uL) ± SD |
|---|---|---|---|---|---|
| A | NextPrep kit | 20 mL | 200 µL | 120 min | 360.9 ± 27.2 |
| B | Zymo | 40 mL | 400 µL | 160 min | 196.1 ± 207.4 |
| C | Norgen | 30 mL | 300 µL | 175 min | 230.1 ± 25.5 |
| D | Wizard | 10 mL | 100 µL | 178 min | 321.6 ± 135.7 |
| E | 40 mL Phase | 40 mL | 400 µL | 143 min | 396.8 ± 48.0 |
| F | 40 mL Phase [Crude urine] | 40 mL | 400 µL | 133 min | 476.1 ± 32.2 |

Figure 7A:
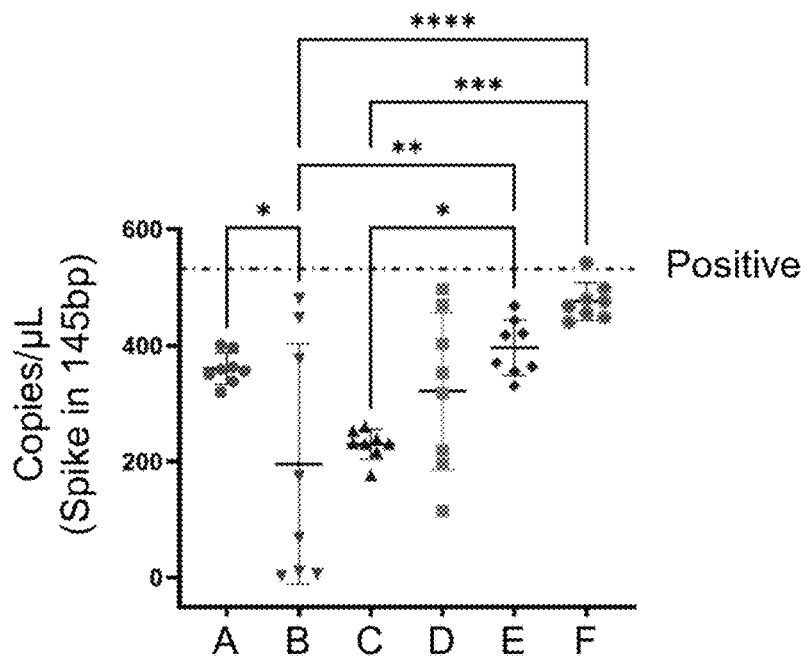
FIG. 7A is a graph showing the recovery of 145 bp DNA spike-in (copies/uL) using the conditions A-F according to Table 6.

Now referring to FIG. 7A, which shows the recovery of 145 bp DNA spike-in (copies/uL) using the conditions A-F according to Table 6. Detection of 145 bp spike-in was performed by Droplet Digital PCR ddPCR. As shown in FIG. 7A, The 140 bp spike-in DNA recovery efficiency using the present extraction method (conditions E) was comparable if not greater than that of the NextPrep (condition A) and Wizard (condition D) extraction kits and significantly higher than that of the Zymo (condition B) and Norgen (condition C) extraction kits. Compared to the NextPrep (condition A), Norgen (condition C) and Wizard (condition D) extraction kits, the present extraction method can process a larger input volume but with a comparable if not shorter extraction time. Compared to Zymo (Condition B) with the same input volume, the present extraction method have a shorter extraction time with a significantly higher yield as well as a much more consistent sample-to-sample performance. Whilst using Urine with cells (condition F), the average DNA recovery by the present extraction method was significantly better than all of the competitors with satisfactory precision (476.1±32.2 copies/uL) even with the presence of cells. This shows that the present extraction method performed well in recovering target DNA with crude urine as well as processed spun down urine. In summary, the overall target DNA extraction performance (in terms of yield, input volume and extraction time) using the method of the present disclosure is surprisingly better compared to the industry standard, commercially available extraction kits.

Example 7b

Further comparison of DNA recovery from urine between the present extraction method and the commercially available extraction kits (Zymo Quick-DNA Urine kit ('Zymo'), Qiagen QIAamp Circulating Nucleic Acid Kit ('Qiagen' or 'QCNA'), Norgen Urine DNA Isolation kit—spin column ('Norgen'), and Wizard Plus miniprep DNA purification system ('Wizard')) was performed by using the present extraction method (also referred as "Phase" herein) with a maximum urine sample input volume of 160 mL, while the commercially available extraction kits utilized the maximum sample input volume and optimal output volume recommended by the manufacturer, and the extraction was performed by following the manufacturer's instruction. Urine samples were provided by 4 males and 4 females (n=8 for each kit). The conditions are summarized in Table 7.

TABLE 7

Comparisons of yield and efficiency using the recommended input and output volume.

| Extraction Kit | Input Volume | Output Volume | Average 145 bp DNA recovery (copies/uL) |
|---|---|---|---|
| Present extraction method ('Phase) | 160 mL | 20 µL | 1304.3 |
| Zymo | 40 mL | 10 µL | 142.7 |
| QCNA (Qiagen) | 4 mL | 20 µL | 69.7 |
| Wizard | 10 mL | 50 µL | 56.0 |
| Norgen | 30 mL | 50 µL | 37.5 |

Figure 7B:
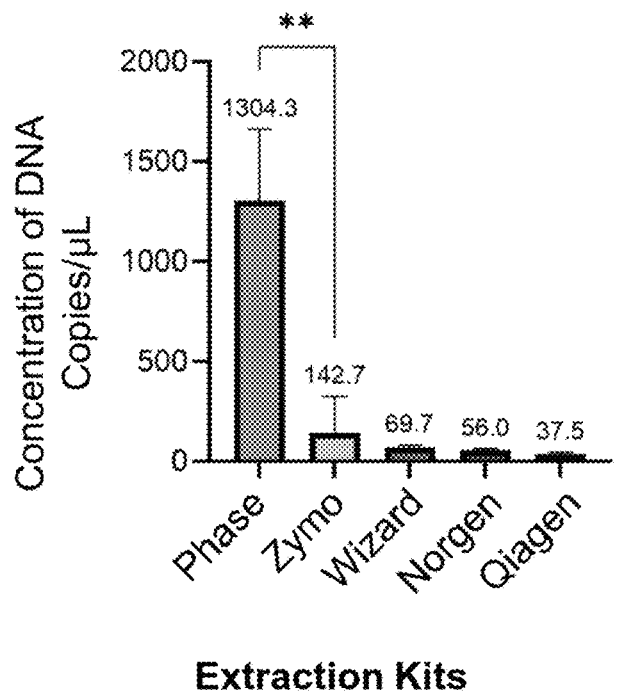
FIG. 7B is a graph showing the average concentration of recovered DNA (copies/uL) using the kits and conditions according to Table 7.

Now referring to FIG. 7B, which shows the average concentration of recovered DNA (copies/uL) using the kits and conditions according to Table 7. Detection of 140 bp spike-in was performed by Droplet Digital PCR ddPCR. The results demonstrated that the present extraction method was able to significantly out-perform all the competitor kits due to the ability to process high input volume and concentrate it to a low output volume.

In summary, the experiments in Examples 7a and 7b demonstrate that the total DNA recovery of the present extraction method is significantly greater than all the other commercially available kits, due to the both the increased allowable sample input volume of the present extraction method and the low output/elution volume as well as the greater recovery efficiency of target DNA.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

Numbered Embodiments 1

Embodiment 1. A method for concentrating and purifying one or more target analytes from a bulk fluid sample, comprising the steps of: (a) preparing a first aqueous two-phase system (ATPS) composition, wherein the first ATPS composition comprises polymers, salts, surfactants, or combinations thereof dissolved in an aqueous solution to form a first phase solution and a second phase solution; (b) adding a sample solution prepared from the bulk fluid sample containing the target analyte(s) to the first ATPS composition, such that the target analyte(s) partition to the first phase solution; (c) collecting the first phase solution and mixing the first phase solution with a second ATPS composition, wherein the second ATPS composition comprises polymers, salts, surfactants, or combinations thereof dissolved in an aqueous solution to form a third phase solution and a fourth phase solution, such that the target analyte(s) partition to and concentrate in the third phase solution; (d) collecting the third phase solution and mixing the third phase solution with a binding buffer to form a mixed solution, wherein the binding buffer comprises at least one chaotropic agent; (e) loading the mixed solution onto an extraction column configured to selectively extract and purify the target analyte(s); (f) eluting and collecting the target analyte(s) from the extraction column, resulting in a final solution containing the concentrated and purified target analyte(s).

Embodiment 2. The method of any one of the preceding embodiments, wherein the sample solution is prepared by dividing the bulk fluid sample containing the target analyte(s) into at least two aliquots of the sample solution, and the first ATPS composition is divided into at least two aliquots, wherein step (b) further includes the following steps: (i) adding each aliquot of said sample solution prepared from the bulk fluid sample containing the target analyte(s) to each aliquot of the first ATPS composition, such that the target analyte(s) partition to the first phase solution; (ii) collecting and combining the first phase solutions of the at least two aliquots of the first ATPS composition to form the first phase solution for step (c).

Embodiment 3. The method of any of the preceding embodiments, wherein the extraction column is a spin column, and wherein step (c) further comprises the following steps: (i) loading a portion of the mixed solution onto the extraction column; (ii) centrifuging the extraction column and discarding the flow-through; and (iii) repeating steps (i) and (ii) above until all of the mixed solution has been passed through the extraction column.

Embodiment 4. The method of any of the preceding embodiments, further comprising the step of: (g) subjecting said final solution to a diagnostic assay for detection and quantification of said target analyte(s).

Embodiment 5. A method for concentrating and purifying one or more target analytes from a bulk fluid sample, comprising the steps of: (a) dividing the bulk fluid sample containing the target analyte(s) into at least two aliquots of a sample solution; (b) preparing at least two aliquots of a first aqueous two-phase system (ATPS) composition, wherein the first ATPS composition comprises polymers, salts, surfactants, or combinations thereof dissolved in an aqueous solution to form a first phase solution and a second phase solution; (c) adding each aliquot of said sample solution containing the target analyte(s) to each aliquot of the first ATPS composition, such that the target analyte(s) partition to the first phase solution; (d) collecting the first phase solutions of the at least two aliquots of the first ATPS composition, and mixing the first phase solutions with a second ATPS composition, wherein the second ATPS composition comprises polymers, salts, surfactants, or combinations thereof dissolved in an aqueous solution to form a third phase solution and a fourth phase solution, such that the target analyte(s) partition to and concentrate in the third phase solution; (e) collecting the third phase solution and mixing the third phase solution with a binding buffer to form a mixed solution, wherein the binding buffer comprises at least one chaotropic agent; (f) loading the mixed solution onto an extraction column configured to selectively extract and purify the target analyte(s); (g) eluting and collecting the target analyte(s) from the extraction column.

Embodiment 6. The method of any one of the preceding embodiments, wherein the bulk fluid sample is selected from the group consisting of blood, plasma, serum, cerebrospinal fluid, urine, saliva, fecal matter, tear, sputum, nasopharyngeal mucus, vaginal discharge and penile discharge.

Embodiment 7. The method of any one of the preceding embodiments, wherein the bulk fluid sample is urine.

Embodiment 8. The method of any one of the preceding embodiments, wherein the bulk fluid sample has a volume of 40 mL or more.

Embodiment 9. The method of any one of the preceding embodiments, wherein each aliquot of said sample solution has a volume of up to 40 ml.

Embodiment 10. The method of any one of the preceding embodiments, wherein the target analytes are selected from the group consisting of nucleic acids, a protein, an antigen, a biomolecule, a sugar moiety, a lipid, a sterol, and combinations thereof.

Embodiment 11. The method of any one of the preceding embodiments, wherein the target analytes are DNA.

Embodiment 12. The method of any one of the preceding embodiments, wherein the target analytes are cell-free DNA or circulating tumor DNA.

Embodiment 13. The method of any one of the preceding embodiments, wherein said polymers are dissolve in the aqueous solution at a concentration of 4%-84% (w/w).

Embodiment 14. The method of any one of the preceding embodiments, wherein said polymers are selected from the group consisting of polyalkylene glycols, such as hydrophobically modified polyalkylene glycols, poly(oxyalkylene) polymers, poly(oxyalkylene) copolymers, such as hydrophobically modified poly(oxyalkylene) copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. The method of any one of the preceding embodiments, wherein the polymer is selected from the group consisting of polyether, polyimine, polyalkylene glycol, vinyl polymer, alkoxylated surfactant, polysaccharides, alkoxylated starch, alkoxylated cellulose, alkyl hydroxyalkyl cellulose, polyether-modified silicones, polyacrylamide, polyacrylic acid and copolymer thereof. The method of any one of the preceding embodiments, wherein the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether, dextran, carboxymethyl dextran, dextran sulfate, hydroxypropyl dextran, starch, carboxymethyl cellulose, polyacrylic acid, hydroxypropyl cellulose, methyl cellulose, ethylhydroxyethylcellulose, maltodextrin, polyethyleneimine, poly N-isopropylacrylamide and copolymers thereof. The method of any one of the preceding embodiments, wherein the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether and poly N-isopropylacrylamide. The method of any one of the preceding embodiments, wherein the polymer is selected from the group consisting of polyacrylamide, polyacrylic acid and copolymers thereof. The method of any one of the preceding embodiments, wherein the polymer is selected from the group consisting of dextran, carboxymethyl dextran, dextran sulfate, hydroxypropyl dextran and starch. The method of any one of the preceding embodiments, wherein the polymer has an average molecular weight in the range of 200-1,000 Da, 200-35,000 Da, 425-2,000 Da, 400-35,000 Da, 980-12,000 Da, or 3,400-5,000,000 Da. The method of any one of the preceding embodiments, wherein the polymer comprises ethylene oxide and propylene oxide units, and the polymer has an EO:PO ratio of 90:10 to 10:90.

Embodiment 15.

Embodiment 16. The method of any one of the preceding embodiments, wherein said salts are dissolved in the aqueous solution at a concentration of 1%-55% (w/w).

Embodiment 17. The method of any one of the preceding embodiments, wherein said salts are dissolved in the aqueous solution at a concentration of 8%-55% (w/w).

Embodiment 18. The method of any one of the preceding embodiments, wherein said salts are selected from the group consisting of kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, a magnesium salt, a lithium salt, a sodium salt, a potassium salt, a cesium salt, a zinc salt, an aluminum salt, a bromide salt, an iodide salt, a fluoride salt, a carbonate salt, a sulfate salt, a citrate salt, a carboxylate salt, a borate salt, a phosphate salt, potassium phosphate and ammonium sulfate.

Embodiment 19. The method of any one of the preceding embodiments, wherein said surfactants are dissolved in the aqueous solution at a concentration of 0.05%-10% (w/w).

Embodiment 20. The method of any one of the preceding embodiments, wherein said surfactants are dissolved in the aqueous solution at a concentration of 0.05%-9.8% (w/w).

Embodiment 21. The method of any one of the preceding embodiments, wherein said surfactants are selected from the group consisting of Triton-X, Triton-114, Igepal CA-630 and Nonidet P-40, anionic surfactants, such as carboxylates, sulphonates, petroleum sulphonates, alkylbenzenesulphonates, naphthalenesulphonates, olefin sulphonates, alkyl sulphates, sulphates, sulphated natural oils & fats, sulphated esters, sulphated alkanolamides, alkylphenols, ethoxylated and sulphated, nonionic surfactants, such as ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, polyoxyethylene fatty acid amides, cationic surfactants, such as quaternary ammonium salts, amines with amide linkages, polyoxyethylene alkyl & alicyclic amines, n,n,n',n' tetrakis substituted ethylenediamines, 2-alkyl 1-hydroxethyl 2-imidazolines, and amphoteric surfactants, such as n-coco 3-aminopropionic acid/sodium salt, n-tallow 3-iminodipropionate, disodium salt, n-carboxymethyl n dimethyl n-9 octadecenyl ammonium hydroxide, n-cocoamidethyl n hydroxyethylglycine, and sodium salt.

Embodiment 22. An ATPS composition selected from the group consisting of A1, A2, A3, A4, AA1, AA2, AA3, and AA4.

Embodiment 23. A kit comprising a first ATPS composition selected from the group consisting of A1, A2, A3, and A4; a second ATPS composition selected from the group consisting of AA1, AA2, AA3, and AA4; and a binding buffer selected from the group consisting of B1, B2, and B3.

Embodiment 24. The kit of any one of the preceding embodiments, further comprises an extraction column.

Numbered Embodiments 2

Embodiment 1. A method for concentrating and purifying one or more target analytes from a sample solution, comprising the steps of: (a) adding a sample solution containing the target analyte(s) to a first aqueous two-phase system (ATPS) to form a mixture that partitions into a first phase and a second phase, wherein the target analyte(s) are concentrated in the first phase; (b) isolating the first phase containing the concentrated target analyte(s), thereby resulting in a concentrated solution; (c) applying magnetic beads to the concentrated solution, such that the magnetic beads bind the target analyte(s) to form a beads-analyte complex; and (d) recovering the target analyte(s) from the beads-analyte complex, resulting in a final solution containing the target analyte(s) that is concentrated and purified.

Embodiment 2. The method of any one of the preceding embodiments, wherein the step (b) further comprises the following steps: (i) adding the isolated first phase that is concentrated with the target analyte(s) to a second ATPS to form a second mixture that partitions into a third phase and a fourth phase, wherein the target analyte(s) are concentrated in the third phase; and (ii) isolating the third phase containing the concentrated target analyte(s) to form the concentrated solution in step (b) for step (c).

Embodiment 3. The method of any of the preceding embodiments, wherein the concentrated solution of step (b) is mixed with a binding buffer, wherein the binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea, thereby resulting in the concentration solution for step (c).

Embodiment 4. The method of any one of the preceding embodiments, wherein the step (d) further comprises the steps of: (i) mixing the beads-analyte complex with a fractionation buffer comprising a polymer, a salt, a surfactant, a chaotropic agent or combinations thereof to form a fractionation solution, such that the target analyte(s) below a target size are released from the beads-analyte complex into the fractionation solution; (ii) immobilizing the beads-analyte complex using a magnetic stand; and (iii) isolating the target analyte(s) below the target size in the fractionation solution from the immobilized beads-analyte complex.

Embodiment 5. The method of any one of the preceding embodiments, wherein the step (d) further comprises the steps of: (iv) adding the isolated target analyte(s) below the target size to a second binding buffer, wherein the second binding buffer comprises at least one chaotropic agent selected from n-butanol, ethanol, guanidinium chloride, guanidinium thiocyanate, lithium perchlorate, lithium acetate, magnesium chloride, phenol, 2-propanol, sodium dodecyl sulfate, thiourea, and urea; (v) applying magnetic beads to a mixture of the isolated target analyte(s) below the target size and the second binding buffer, wherein the magnetic beads bind the target analyte(s) below the target size to form a second beads-analyte complex; and (vi) recovering the target analyte(s) from the second beads-analyte complex.

Embodiment 6. The method of any one of the preceding embodiments, further comprising the step of: (e) subjecting said final solution to a diagnostic assay for detection and quantification of said target analyte(s).

Embodiment 7. The method of any one of the preceding embodiments, wherein the target analyte(s) is selected from the group consisting of nucleic acids, a protein, an antigen, a biomolecule, a sugar moiety, a lipid, a sterol, and combinations thereof.

Embodiment 8. The method of any one of the preceding embodiments, wherein the target analyte(s) is DNA.

Embodiment 9. The method of any preceding embodiments, wherein the target analyte(s) is cell-free DNA or circulating tumor DNA.

Embodiment 10. The method of any of the preceding embodiments, wherein the first ATPS comprises first ATPS components capable of forming the first phase and the second phase when the first ATPS components are dissolved in an aqueous solution, wherein the first ATPS components are selected from the group consisting of polymers, salts, surfactants, and combinations thereof.

Embodiment 11. The method of any one of embodiments 2-10, wherein the second ATPS comprises second ATPS components capable of forming the third phase and the fourth phase when the second ATPS components are dissolved in an aqueous solution, wherein the second ATPS components are selected from the group consisting of polymers, salts, surfactants, and combinations thereof.

Embodiment 12. The method of embodiment 10 or 11, wherein said polymers dissolve in the aqueous solution at a concentration of 4%-84% (w/w).

Embodiment 13. The method of any one of embodiments 10-12, wherein said polymers are selected from the group consisting of polyalkylene glycols, such as hydrophobically modified polyalkylene glycols, poly(oxyalkylene) polymers, poly(oxyalkylene) copolymers, such as hydrophobically modified poly(oxyalkylene) copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. The method of any one of the preceding embodiments, wherein the polymer is selected from the group consisting of polyether, polyimine, polyalkylene glycol, vinyl polymer, alkoxylated surfactant, polysaccharides, alkoxylated starch, alkoxylated cellulose, alkyl hydroxyalkyl cellulose, polyether-modified silicones, polyacrylamide, polyacrylic acid and copolymer thereof. The method of any one of the preceding embodiments, wherein the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether, dextran, carboxymethyl dextran, dextran sulfate, hydroxypropyl dextran, starch, carboxymethyl cellulose, polyacrylic acid, hydroxypropyl cellulose, methyl cellulose, ethylhydroxyethylcellulose, maltodextrin, polyethyleneimine, poly N-isopropylacrylamide and copolymers thereof. The method of any one of the preceding embodiments, wherein the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether and poly N-isopropylacrylamide. The method of any one of the preceding embodiments, wherein the polymer is selected from the group consisting of polyacrylamide, polyacrylic acid and copolymers thereof. The method of any one of the preceding embodiments, wherein the polymer is selected from the group consisting of dextran, carboxymethyl dextran, dextran sulfate, hydroxypropyl dextran and starch. The method of any one of the preceding embodiments, wherein the polymer has an average molecular weight in the range of 200-1,000 Da, 200-35,000 Da, 425-2,000 Da, 400-35,000 Da, 980-12,000 Da, or 3,400-5,000,000 Da. The method of any one of the preceding embodiments, wherein the polymer comprises ethylene oxide and propylene oxide units, and the polymer has an EO:PO ratio of 90:10 to 10:90.

Embodiment 14.

Embodiment 15. The method of any one of embodiments 10-14, wherein said salts dissolve in the aqueous solution at a concentration of 1%-80% (w/w).

Embodiment 16. The method of any one of embodiments 10-15, wherein said salts dissolve in the aqueous solution at a concentration of 8%-80% (w/w).

Embodiment 17. The method of any one of embodiments 10-16, wherein said salts are selected from the group consisting of kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, a magnesium salt, a lithium salt, a sodium salt, a potassium salt, a cesium salt, a zinc salt, an aluminum salt, a bromide salt, an iodide salt, a fluoride salt, a carbonate salt, a sulfate salt, a citrate salt, a carboxylate salt, a borate salt, a phosphate salt, potassium phosphate and ammonium sulfate.

Embodiment 18. The method of any one of embodiments 10-17, wherein said surfactants dissolve in the aqueous solution at a concentration of 0.05%-10% (w/w).

Embodiment 19. The method of any one of embodiments 10-18, wherein said surfactants dissolve in the aqueous solution at a concentration of 0.05%-9.8% (w/w).

Embodiment 20. The method of any one of embodiments 10-19, wherein said surfactants are selected from the group consisting of Triton-X, Triton-114, Igepal CA-630 and Nonidet P-40, anionic surfactants, such as carboxylates, sulphonates, petroleum sulphonates, alkylbenzenesulphonates, naphthalenesulphonates, olefin sulphonates, alkyl sulphates, sulphates, sulphated natural oils & fats, sulphated esters, sulphated alkanolamides, alkylphenols, ethoxylated and sulphated, nonionic surfactants, such as ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, polyoxyethylene fatty acid amides, cationic surfactants, such as quaternary ammonium salts, amines with amide linkages, polyoxyethylene alkyl & alicyclic amines, n,n,n',n' tetrakis substituted ethylenediamines, 2-alkyl 1-hydroxethyl 2-imidazolines, and amphoteric surfactants, such as n-coco 3-aminopropionic acid/sodium salt, n-tallow 3-iminodipropionate, disodium salt, n-carboxymethyl n dimethyl n-9 octadecenyl ammonium hydroxide, n-cocoamidethyl n hydroxyethylglycine, and sodium salt.

Embodiment 21. The method of any of the preceding embodiments, wherein the step (a) further comprises the steps of: (i) embedding a porous material with components capable of forming the first ATPS; and (ii) contacting the sample solution with the porous material embedded with the components, wherein said components form the first phase and the second phase when the sample solution travels through said porous material.

Numbered Embodiments 3

Embodiment 1. A method for concentrating and purifying at least one target analyte from a clinical biological sample, comprising the steps of (a) combining the clinical biological sample with a first aqueous two-phase system (ATPS) composition comprising a polymer, a salt component comprising at least one salt, a surfactant, or any combination thereof dissolved in an aqueous solution to form a target-rich phase solution and a target-poor phase solution; (b) collecting the target-rich phase; (c) optionally adding the target-rich phase to a second ATPS composition comprising a polymer, a salt component comprising at least one salt, a surfactant, or any combination thereof dissolved in an aqueous solution to form a second target-rich phase solution and a second target-poor phase solution, and collecting the second target-rich phase; (d) optionally mixing the target-rich phase from step (b) or the second target-rich phase from step (c) with a binding buffer to form a mixed solution; (e) contacting the target rich phase from step (b), the second target-rich phase from step (c) or the mixed solution from step (d) with a solid phase medium configured to selectively bind the target analyte such that the solid phase medium binds to the target analyte; and (f) eluting and collecting the target analyte from the solid phase medium with an eluting solution, resulting in a final solution containing the concentrated and purified target analyte.

Embodiment 2. The method of any one of the preceding embodiments, further comprising the step of washing the solid phase medium with one or more appropriate solvents to remove impurities after step (e) and before step (f).

Embodiment 3. The method of any one of the preceding embodiments, wherein the appropriate solvent is the binding buffer.

Embodiment 4. The method of any one of the preceding embodiments, further comprising the step of treating the clinical biological sample with a lysing composition before step (a).

Embodiment 5. The method of any one of the preceding embodiments, wherein the binding buffer comprises a chaotropic agent comprising an anion selected from the group consisting of thiocyanate, isothiocyanate, perchlorate, acetate, trichloroacetate, trifluoroacetate, chloride, and iodide.

Embodiment 6. The method of any one of the preceding embodiments, wherein the binding buffer comprises a chaotropic agent selected from the group consisting of guanidinium hydrochloride (GHCl), guanidinium thiocyanate, guanidinium isothiocyanate (GITC)), sodium thiocyanate, sodium iodide, sodium perchlorate, sodium trichloroacetate, sodium trifluoroacetate, lithium perchlorate, lithium acetate, magnesium chloride, phenol, 2-propanol, thiourea, and urea.

Embodiment 7. The method of any one of the preceding embodiments, wherein the binding buffer comprises a 2M to 7M solution of the chaotropic agent.

Embodiment 8. The method of any one of the preceding embodiments, wherein the binding buffer further comprises a polymer at a concentration of 5-20% (w/v).

Embodiment 9. The method of any one of the preceding embodiments, wherein the clinical biological sample is blood, plasma, urine, saliva, stool, cerebrospinal fluid (CSF), lymph, serum, sputum, peritoneal fluid, sweat, tears, nasal swab, vaginal swab, endocervical swab, semen, or breast milk.

Embodiment 10. The method of any one of the preceding embodiments, wherein the clinical biological sample is <500 mL.

Embodiment 11. The method of any one of the preceding embodiments, wherein the target analyte is selected from the group consisting of a nucleic acid, a protein, an antigen, a biomolecule, a sugar moiety, a lipid, a sterol, exosomes, and any combination thereof.

Embodiment 12. The method of any one of the preceding embodiments, wherein the target analyte is a nucleic acid, and the nucleic acid is gDNA, cDNA, plasmid DNA, mitochondrial DNA, cell-free DNA (cfDNA), circulating tumor DNA (ctDNA), circulating fetal DNA, cell-free microbial DNA, micro RNA (miRNA), messenger RNA (mRNA), transfer RNA (tRNA), ribosomal RNA (rRNA), circular RNA, long non-coding RNA (lncRNA) or combinations thereof.

Embodiment 13. The method of any one of the preceding embodiments, wherein the nucleic acid is cfDNA, cell-free fetal DNA, mitochondrial DNA, cell-free microbial DNA, or ctDNA.

Embodiment 14. The method of any one of the preceding embodiments, wherein step (e) comprises the following steps: (i) contacting a portion of the mixed solution with the solid phase medium such that the target analyte binds to the solid phase medium to form a solid phase extraction complex; (ii) perturbing the solid phase extraction complex and discarding the flow-through; and (iii) optionally repeating steps (i) and (ii).

Embodiment 15. The method of any one of the preceding embodiments, wherein the solid phase medium is a plurality of beads.

Embodiment 16. The method of any one of the preceding embodiments, wherein the beads are selected from the group consisting of magnetic beads, silica-based beads, carboxyl beads, hydroxyl beads, and amine-coated beads.

Embodiment 17. The method of any one of the preceding embodiments, wherein the solid phase extraction complex is a beads-analyte complex; perturbing is spinning; and the flowthrough is the supernatant.

Embodiment 18. The method of any one of the preceding embodiments, wherein the target analyte is a nucleic acid less than a target size; the plurality of beads binds to the target analyte and to other nucleic acids; the eluting solution is a fractionation buffer that, when contacted with the beads during the elution step (f), causes the target analyte to be released while not releasing the other nucleic acids, resulting in a final solution containing the concentrated and purified target analyte(s).

Embodiment 19. The method of any one of the preceding embodiments, wherein the fractionation buffer comprises a polymer, a chaotropic agent, or any combination thereof.

Embodiment 20. The method of any one of the preceding embodiments, wherein the solid phase medium is an extraction column.

Embodiment 21. The method of any one of the preceding embodiments, wherein the extraction column is a spin column.

Embodiment 22. The method of any one of the preceding embodiments, wherein step (e) comprises the following steps: (i) loading a portion of the mixed solution from step (d) onto the extraction column; (ii) centrifuging the extraction column and discarding the flow-through; and (iii) optionally repeating steps (i) and (ii) above one or more times, until all of the mixed solution has been passed through the extraction column.

Embodiment 23. The method of any one of the preceding embodiments, wherein the salt comprises a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium.

Embodiment 24. The method of any one of the preceding embodiments, wherein the salt comprises an anion selected from the group consisting of phosphate, hydrogen phosphate, dihydrogen phosphate, sulfate, sulfide, sulfite, hydrogen sulfate, carbonate, hydrogen carbonate, acetate, nitrate, nitrite, sulfite, chloride, fluoride, chlorate, perchlorate, chlorite, hypochlorite, bromide, bromate, hypobromite, iodide, iodate, cyanate, thiocyanate, isothiocyanate, oxalate, formate, chromate, dichromate, permanganate, polyacrylate, hydroxide, hydride, citrate, borate, and tris.

Embodiment 25. The method of any one of the preceding embodiments, wherein the polymer is selected from the group consisting of polyethers, polyimines, polyacrylates, polyalkylene glycol, vinyl polymer, alkoxylated surfactant, polysaccharides, alkoxylated starch, alkoxylated cellulose, alkyl hydroxyalkyl cellulose, polyether-modified silicones, polyacrylamide, polyacrylic acid and one or more copolymers thereof.

Embodiment 26. The method of any one of the preceding embodiments, wherein the polymer is selected from the group consisting of dipropylene glycol, tripropylene glycol, polyethylene glycol, polypropylene glycol, poly(ethylene glycol-propylene glycol), poly(ethylene glycol-ran-propylene glycol), polyvinyl pyrrolidone, polyvinyl alcohol, polyvinyl caprolactam, polyvinyl methylether, dextran, carboxymethyl dextran, dextran sulfate, hydroxypropyl dextran, starch, carboxymethyl cellulose, polyacrylic acid, hydroxypropyl cellulose, methyl cellulose, ethylhydroxyethylcellulose, maltodextrin, polyethyleneimine, poly N-isopropylacrylamide and copolymers thereof.

Embodiment 27. The method of any one of the preceding embodiments, wherein the surfactant is selected from the group consisting of an anionic surfactant, a nonionic surfactant, a cationic surfactant, and an amphoteric surfactant; wherein the anionic surfactant is carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, or sodium N-lauroyl sarcosinate (NLS); the nonionic surfactant is ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, or polyoxyethylene fatty acid amides; the cationic surfactant is quaternary ammonium salts, amines with amide linkages, polyoxyethylene alkyl amines, polyoxyethylene alicyclic amines, n,n,n',n' tetrakis substituted ethylenediamines, or 2-alkyl 1-hydroxethyl 2-imidazolines; and the amphoteric surfactant is n-coco 3-aminopropionic acid or a sodium salt thereof, n-tallow 3-iminodipropionate or a disodium salt thereof, n-carboxymethyl n dimethyl n-9 octadecenyl ammonium hydroxide, or n-cocoamidethyl n hydroxyethylglycine or a sodium salt thereof.

Embodiment 28. The method of any one of the preceding embodiments, wherein the surfactant is Triton X-100, Triton X-114, Triton X-45, Tween 20, Igepal CA630, Brij 58, Brij O10, Brij L23, Pluronic L-61, Pluronic F-127, sodium dodecyl sulfate, sodium cholate, sodium deoxycholate, sodium N-lauroyl sarcosinate (NLS), Hexadecyltrimethlammonium bromide, or span 80.

Embodiment 29. The method of any one of the preceding embodiments, wherein the polymer has an average molecular weight in the range of 200-1,000 Da, 200-35,000 Da, 300-35,000 Da, 400-2,000 Da, 400-35,000 Da, 2,500-2,500,000 Da, 1,250-4,000,000 Da, or 6,000-5,000,000 Da.

Embodiment 30. The method of any one of the preceding embodiments, wherein the polymer of the first ATPS composition or the second ATPS composition is dissolved in an aqueous solution at a concentration of 0.5-80% (w/v).

Embodiment 31. The method of any one of the preceding embodiments, wherein the polymer of the first ATPS composition or the second ATPS composition is dissolved in an aqueous solution at a concentration of 0.2-50% (w/v).

Embodiment 32. The method of any one of the preceding embodiments, wherein the salt component of the first ATPS composition or the second ATPS composition is dissolved in an aqueous solution at a concentration of 0.1% to 80% (w/v).

Embodiment 33. The method of any one of the preceding embodiments, wherein the surfactant of the first ATPS composition or the second ATPS compositions is dissolved in an aqueous solution at a concentration of 0.1%-90% (w/v).

Embodiment 34. The method of any one of the preceding embodiments, wherein the first ATPS composition or the second ATPS composition is a polymer-salt system, polymer-polymer system, or a micellar system.

Embodiment 35. The method of any one of the preceding embodiments, wherein the first ATPS composition or the second ATPS composition is a polymer-salt system; the polymer is dissolved in an aqueous solution at a concentration of 0.5-80% (w/v); and the salt component is dissolved in an aqueous solution at a concentration of 0.1%-80% (w/v).

Embodiment 36. The method of any one of the preceding embodiments, wherein the polymer of the first ATPS composition is dissolved in an aqueous solution at a concentration of 5-80% (w/v) and the salt component of the first ATPS composition is dissolved in an aqueous solution at a concentration of 0.1%-80% (w/v); and the polymer of the second ATPS composition is dissolved in an aqueous solution at a concentration of 0.5-30% (w/v) and the salt component of the second ATPS composition is dissolved in an aqueous solution at a concentration of 5%-60% (w/v).

Embodiment 37. The method of any one of the preceding embodiments, wherein the first ATPS composition or the second ATPS composition further comprises at least one salt at a concentration of 0.01%-10% (w/v), or at least one surfactant at a concentration of 0.01%-10% (w/v).

Embodiment 38. The method of any one of the preceding embodiments, wherein the first ATPS composition or the second ATPS composition is a polymer-polymer system comprising at least two polymers, and each polymer is dissolved in an aqueous solution at a concentration of 0.2-50% (w/v).

Embodiment 39. The method of any one of the preceding embodiments, wherein the first ATPS composition or the second ATPS composition further comprises at least one salt at a concentration of 0.01%-10% (w/v), or at least one surfactant at a concentration of 0.01%-10% (w/v).

Embodiment 40. The method of any one of the preceding embodiments, wherein the at least one salt comprises a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium and the at least one surfactant selected from the group consisting of an anionic surfactant, a nonionic surfactant, a cationic surfactant, and an amphoteric surfactant; wherein the anionic surfactant is carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, or sodium N-lauroyl sarcosinate (NLS); the nonionic surfactant is ethoxylated aliphatic alcohol, ester, glycol esters of fatty acids, carboxylic amides, monoalkanolamine condensates, or polyoxyethylene fatty acid amides; the cationic surfactant is quaternary ammonium salts, amines with amide linkages, polyoxyethylene alkyl amines, polyoxyethylene alicyclic amines, n,n,n',n' tetrakis substituted ethylenediamines, or 2-alkyl 1-hydroxethyl 2-imidazolines; and the amphoteric surfactant is n-coco 3-aminopropionic acid or a sodium salt thereof, n-tallow 3-iminodipropionate or a disodium salt thereof, n-carboxymethyl n dimethyl n-9 octadecenyl ammonium hydroxide, or n-cocoamidethyl n hydroxyethylglycine or a sodium salt thereof.

Embodiment 41. The method of any one of the preceding embodiments, wherein the first ATPS composition or the second ATPS composition is a micellar system comprising at least one surfactant, and each surfactant is dissolved in an aqueous solution at a concentration of 0.1%-90% (w/v).

Embodiment 42. The method of any one of the preceding embodiments, wherein the first ATPS composition or the second ATPS composition further comprises at least one salt at a concentration of 0.01%-30% (w/v).

Embodiment 43. The method of any one of the preceding embodiments, wherein the at least one salt comprises a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium.

Embodiment 44. The method of any one of the preceding embodiments, wherein the first ATPS composition and the second ATPS composition are selected from Table 1.0.

Embodiment 45. The method of any one of the preceding embodiments, wherein the first ATPS composition or the second ATPS composition further comprises 0.5-2 mM ethylenediaminetetraacetic acid (EDTA).

Embodiment 46. The method of any one of the preceding embodiments, further comprising the step of analyzing the final solution from step (f) using a method selected from the group consisting of qPCR, ddPCR, qubit, ELISA, NGS sequencer, bisulfide, RT-PCR, sanger sequencing, nanodrop, nanopore sequencing, nucleic acid sequencing, and PCR-based assays.

Embodiment 47. The method of any one of the preceding embodiments, wherein the target analyte is a biomarker indicating the presence or risk of a medical condition or disease in a patient, wherein the medical condition or disease is an infectious disease, cancer, or a genetic disease.

Embodiment 48. The method of any one of the preceding embodiments, wherein the clinical biological sample is a bulk fluid sample having a volume >10 mL, further comprising the following step before step (a): dividing the bulk fluid sample into at least two aliquots of a sample solution; wherein each aliquot is separately combined with the first ATPS in steps (a) and optionally the collected target rich phase from step (b) is separately combined with the second ATPS in step (c) to form each aliquot's target rich phase.

Embodiment 49. The method of any one of the preceding embodiments, wherein each aliquot's target-rich phase from step (b) or each aliquot's second target-rich phase from step (c) is combined together to form a final target rich phase for step (d).

Embodiment 50. The method of any one of the preceding embodiments, wherein the bulk fluid sample is urine.

Embodiment 51. A method of treating cancer or infectious disease in a patient in need thereof, comprising (i) obtaining a clinical biological sample from the patient; (ii) concentrating and purifying at least one target analyte from the clinical biological sample according to the method of any one of the preceding embodiments; (iii) analyzing the final solution; and (iv) treating the patient if the information obtained from the target analyte indicates that the patient has cancer or is at risk of developing cancer.

Embodiment 52. The method of any one of the preceding embodiments, wherein the cancer is CNS cancer, breast cancer, bladder cancer, pancreatic cancer, lung cancer, melanomas, colon cancer, hematopoietic cancer or ovarian cancer and wherein the infectious disease is HPV.

Embodiment 53. The method of any one of the preceding embodiments, wherein the target analyte is transrenal cFDNA or ctDNA, and wherein the cancer is systemic cancer.

Embodiment 54. The method of any one of the preceding embodiments, wherein the target analyte is urogenital cFDNA or ctDNA, and wherein the cancer is urogenital cancer.

Embodiment 55. The method of any one of the preceding embodiments, wherein the target analyte is bladder cancer DNA and the medical condition or disease is bladder cancer.

Embodiment 56. The method of any one of the preceding embodiments, wherein the target analyte is HPV viral RNA or HPV viral DNA, and the medical condition or disease is HPV.

Embodiment 57. A kit comprising a first ATPS composition; a second ATPS composition; a binding buffer; and a solid phase medium; wherein the first ATPS composition, the second ATPS composition, the binding buffer, and the solid phase medium are selected from any one of the preceding embodiments.

What is claimed is:

1. A method for concentrating and purifying at least one target analyte from a clinical biological sample, comprising the steps of
    (a) combining the clinical biological sample with a first aqueous two-phase system (ATPS) composition comprising a polymer, a salt component comprising at least one salt, a surfactant, or any combination thereof dissolved in an aqueous solution to form a target-rich phase solution and a target-poor phase solution, such that the target analyte is concentrated in the target-rich phase;
    (b) collecting the target-rich phase;
    (c) optionally adding the target-rich phase to a second ATPS composition comprising a polymer, a salt component comprising at least one salt, a surfactant, or any combination thereof dissolved in an aqueous solution to form a second target-rich phase solution and a second target-poor phase solution, such that the target analyte is concentrated in the second target-rich phase, and collecting the second target-rich phase;
    (d) optionally mixing the target-rich phase from step (b) or the second target-rich phase from step (c) with a binding buffer to form a mixed solution;
    (e) contacting the target rich phase from step (b), the second target-rich phase from step (c) or the mixed solution from step (d) with a solid phase medium configured to selectively bind the target analyte such that the solid phase medium binds to the target analyte; and
    (f) eluting and collecting the target analyte from the solid phase medium with an eluting solution, resulting in a final solution containing the concentrated and purified target analyte; and
    (g) subjecting said final solution to a diagnostic assay for detection and quantification of the target analyte;
    wherein the target analyte is a biomarker indicating the presence or risk of a medical condition or disease in a patient, wherein the medical condition or disease is HPV.

2. The method of claim 1, wherein the clinical biological sample is blood, plasma, urine, saliva, stool, cerebrospinal fluid (CSF), lymph, serum, sputum, peritoneal fluid, sweat, tears, nasal swab, vaginal swab, endocervical swab, semen, or breast milk.

3. The method of claim 2, wherein the clinical biological sample is urine.

4. The method of claim 1, further comprising the step of washing the solid phase medium with one or more appropriate solvents to remove impurities after step (e) and before step (f).

5. The method of claim 1, further comprising the step of treating the clinical biological sample with a lysing composition before step (a).

6. The method of claim 1, wherein the binding buffer comprises a chaotropic agent comprising an anion selected from the group consisting of thiocyanate, isothiocyanate, perchlorate, acetate, trichloroacetate, trifluoroacetate, chloride, and iodide.

7. The method of claim 1, wherein the target analyte is a nucleic acid, wherein the nucleic acid is HPV viral RNA or HPV viral DNA.

8. The method of claim 1, wherein step (e) comprises the following steps:
    (i) contacting a portion of the mixed solution with the solid phase medium such that the target analyte binds to the solid phase medium to form a solid phase extraction complex;
    (ii) perturbing the solid phase extraction complex and discarding the flow-through; and
    (iii) optionally repeating steps (i) and (ii).

9. The method of claim 8, wherein the solid phase medium is a plurality of beads, wherein the beads are selected from the group consisting of magnetic beads, silica-based beads, carboxyl beads, hydroxyl beads, and amine-coated beads; the solid phase extraction complex is a beads-analyte complex; perturbing is spinning; and the flowthrough is the supernatant;
    wherein
    the target analyte is a nucleic acid less than a target size;
    the plurality of beads binds to the target analyte and to other nucleic acids;
    the eluting solution is a fractionation buffer that, when contacted with the beads during the elution step (f), causes the target analyte to be released while not releasing the other nucleic acids, resulting in a final solution containing the concentrated and purified target analyte(s); wherein the fractionation buffer comprises a polymer, a chaotropic agent, or any combination thereof.

10. The method of claim 1,
    wherein the solid phase medium is an extraction column, wherein the extraction column is a spin column; and
    wherein step (e) comprises the following steps:
    (i) loading a portion of the mixed solution from step (d) onto the extraction column;
    (ii) centrifuging the extraction column and discarding the flow-through; and
    (iii) optionally repeating steps (i) and (ii) above one or more times, until all of the mixed solution has been passed through the extraction column.

11. The method of claim 1, wherein the salt comprises a cation selected from the group consisting of sodium, potassium, calcium, ammonium, lithium, magnesium, aluminium, cesium, barium, straight or branched trimethyl ammonium, triethyl ammonium, tripropyl ammonium, tributyl ammonium, tetramethyl ammonium, tetraethyl ammonium, tetrapropyl ammonium and tetrabutyl ammonium; and an anion selected from the group consisting of phosphate, hydrogen phosphate, dihydrogen phosphate, sulfate, sulfide, sulfite, hydrogen sulfate, carbonate, hydrogen carbonate, acetate, nitrate, nitrite, sulfite, chloride, fluoride, chlorate, perchlorate, chlorite, hypochlorite, bromide, bromate, hypobromite, iodide, iodate, cyanate, thiocyanate, isothiocyanate, oxalate, formate, chromate, dichromate, permanganate, polyacrylate, hydroxide, hydride, citrate, borate, and tris; and wherein the polymer is selected from the group consisting of polyethers, polyimines, polyacrylates, polyalkylene glycol, vinyl polymer, alkoxylated surfactant, polysaccharides, alkoxylated starch, alkoxylated cellulose, alkyl hydroxyalkyl cellulose, polyether-modified silicones, polyacrylamide, polyacrylic acid and one or more copolymers thereof; and/or wherein the surfactant is selected from the group consisting of an anionic surfactant, a nonionic surfactant, a cationic surfactant, and an amphoteric surfactant; wherein the anionic surfactant is carboxylates, sulphonates, petroleum sulphonates, alkylbenzenesulphonates, naphthalenesulphonates, olefin sulphonates, alkyl sulphates, sulphates, sulphated natural oils, sulphated natural fats, sulphated esters, sulphated alkanolamides, sulphated alkylphenols, ethoxylated alkylphenols, or sodium N-lauroyl sarcosinate (NLS);

the nonionic surfactant is ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, or polyoxyethylene fatty acid amides;

the cationic surfactant is quaternary ammonium salts, amines with amide linkages, polyoxyethylene alkyl amines, polyoxyethylene alicyclic amines, n,n,n',n' tetrakis substituted ethylenediamines, or 2-alkyl 1-hydroxyethyl 2-imidazolines; and the amphoteric surfactant is n-coco 3-aminopropionic acid or a sodium salt thereof, n-tallow 3-iminodipropionate or a disodium salt thereof, n-carboxymethyl n dimethyl n-9 octadecenyl ammonium hydroxide, or n-cocoamidethyl n hydroxyethylglycine or a sodium salt thereof.

12. The method of claim 1, wherein the polymer of the first ATPS composition or the second ATPS composition is dissolved in an aqueous solution at a concentration of 0.5-80% (w/v);

the salt component of the first ATPS composition or the second ATPS composition is dissolved in an aqueous solution at a concentration of 0.1% to 80% (w/v); and/or the surfactant of the first ATPS composition or the second ATPS compositions is dissolved in an aqueous solution at a concentration of 0.1%-90% (w/v).

13. The method of claim 1, wherein the first ATPS composition or the second ATPS composition is a polymer-salt system;
the polymer is dissolved in an aqueous solution at a concentration of 0.5-80% (w/v); and
the salt component is dissolved in an aqueous solution at a concentration of 0.1%-80% (w/v).

14. The method of claim 1, wherein the first ATPS composition or the second ATPS composition is a polymer-polymer system comprising at least two polymers, and each polymer is dissolved in an aqueous solution at a concentration of 0.2-50% (w/v).

15. The method of claim 1, wherein the first ATPS composition or the second ATPS composition is a micellar system comprising at least two surfactants, and each surfactant is dissolved in an aqueous solution at a concentration of 0.1%-90% (w/v).

16. The method of claim 1, wherein the clinical biological sample is a bulk fluid sample having a volume >10 mL, further comprising the following step before step (a): dividing the bulk fluid sample into at least two aliquots of a sample solution;
wherein each aliquot is separately combined with the first ATPS in steps (a) and optionally the collected target rich phase from step (b) is separately combined with the second ATPS in step (c) to form each aliquot's target rich phase; wherein each aliquot's target-rich phase from step (b) or each aliquot's second target-rich phase from step (c) is combined together to form a final target rich phase for step (d).

17. A method of diagnosing or treating HPV in a patient in need thereof, comprising
(i) obtaining a clinical biological sample from the patient;
(ii) concentrating and purifying at least one target analyte from the clinical biological sample according to the method of claim 1;
(iii) analyzing the final solution; and
(iv) determining if the information obtained from the target analyte indicates that the patient has HPV or is at risk of developing HPV; and
(v) optionally treating the patient.

18. The method of claim 17, wherein the target analyte is HPV viral RNA or HPV viral DNA.

19. The method of claim 17, wherein the clinical biological sample is blood, plasma, urine, saliva, stool, cerebrospinal fluid (CSF), lymph, serum, sputum, peritoneal fluid, sweat, tears, nasal swab, vaginal swab, endocervical swab, semen, or breast milk.

* * * * *